US009227967B2

(12) United States Patent
Evans et al.

(10) Patent No.: US 9,227,967 B2
(45) Date of Patent: *Jan. 5, 2016

(54) INHIBITOR COMPOUNDS OF SEMICARBAZIDE-SENSITIVE AMINE OXIDASES

(75) Inventors: David Evans, London (GB); Allison Carley, London (GB); Alison Stewart, London (GB); Michael Higginbottom, London (GB); Edward Savory, London (GB); Iain Simpson, London (GB); Marianne Nilsson, Stockholm (SE); Martin Haraldsson, Stockholm (SE); Erik Nordling, Stockholm (SE); Tobias Koolmeister, Stockholm (SE)

(73) Assignee: Proximagen Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/634,732

(22) PCT Filed: Mar. 14, 2011

(86) PCT No.: PCT/EP2011/053818
§ 371 (c)(1),
(2), (4) Date: Oct. 30, 2012

(87) PCT Pub. No.: WO2011/113798
PCT Pub. Date: Sep. 22, 2011

(65) Prior Publication Data
US 2013/0102587 A1 Apr. 25, 2013

(30) Foreign Application Priority Data
Mar. 15, 2010 (GB) .................................. 1004311.5

(51) Int. Cl.
C07D 471/04 (2006.01)
C07D 487/04 (2006.01)
C07D 498/08 (2006.01)
C07D 519/00 (2006.01)
C07D 491/08 (2006.01)

(52) U.S. Cl.
CPC ............ *C07D 471/04* (2013.01); *C07D 487/04* (2013.01); *C07D 491/08* (2013.01); *C07D 498/08* (2013.01); *C07D 519/00* (2013.01)

(58) Field of Classification Search
None
See application file for complete search history.

(56) References Cited

U.S. PATENT DOCUMENTS

| 8,633,318 B2 * | 1/2014 | Savory et al. ................. 546/119 |
| 2007/0254867 A1 | 11/2007 | Hasvold et al. |

FOREIGN PATENT DOCUMENTS

| DE | 19649460 A1 | 5/1998 |
| WO | 9640686 A1 | 12/1996 |
| WO | 0119821 A1 | 3/2001 |
| WO | 2002038153 | 5/2002 |
| WO | 2003006003 | 1/2003 |
| WO | 03029209 A2 | 4/2003 |
| WO | 2005014530 | 2/2005 |
| WO | 2005040169 A2 | 5/2005 |
| WO | 2005074603 A2 | 8/2005 |
| WO | 2005116028 A2 | 12/2005 |
| WO | 2006114180 | 11/2006 |
| WO | 2007002667 A2 | 1/2007 |
| WO | 2007115315 A2 | 10/2007 |
| WO | 2007120528 | 10/2007 |
| WO | 2007134828 A1 | 11/2007 |
| WO | 2008088744 A1 | 7/2008 |
| WO | 2008135442 A1 | 11/2008 |
| WO | 2009080682 A1 | 7/2009 |
| WO | 2009095162 A1 | 8/2009 |
| WO | 2009108551 | 9/2009 |
| WO | 2010031789 | 3/2010 |
| WO | 2010031791 | 3/2010 |
| WO | 2010064020 A1 | 6/2010 |
| WO | 2011019060 | 2/2011 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Jordan, V. C. Nature Reviews: Drug Discovery, 2, 2003, 205-213.*
Boomsma et al. ("Semicarbazide-sensitive amine oxidase (SSAO): from cell to circulation", Med Sci Monitor, 2005; 11(4) RA122-126).*
International Search Report, PCT International Application No. PCT/EP2011/053818, mailed Sep. 12, 2011.
Dunkel, Petra et al. "Semicarbazide-sensitive amine oxidase/vascular adhesion protein-1: a patent survey," Expert Opin. Ther. Patents, 21(9): 1453-1471 (2011).
Search Report dated Oct. 17, 2014 from corresponding Singapore Application No. 2012206602-3.

* cited by examiner

*Primary Examiner* — Jeffrey S Lundgren
*Assistant Examiner* — William Lee
(74) *Attorney, Agent, or Firm* — Sean B. Mahoney

(57) ABSTRACT

Disclosed are compounds which inhibit SSAO enzyme activity. Also disclosed are pharmaceutical compositions comprising these compounds and the use of these compounds in the treatment or prevention of medical conditions wherein inhibition of SSAO activity is beneficial, such as inflammatory diseases, immune disorders and the inhibition of tumor growth.

37 Claims, No Drawings

INHIBITOR COMPOUNDS OF SEMICARBAZIDE-SENSITIVE AMINE OXIDASES

CROSS REFERENCE TO RELATED APPLICATION

The present application is the U.S. national stage application of International Application PCT/EP2011/053818, filed Mar. 14, 2011, which international application was published on Sep. 22, 2011 as International Publication WO 2011/113798. The International Application claims priority of British Patent Application 1004311.5, filed Mar. 15, 2010.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

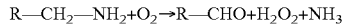

$R-CH_2-NH_2+O_2 \rightarrow R-CHO+H_2O_2+NH_3$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88; Irjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-Ichihara F, Castermans K, Auvinen K, Oude Egbrink M G, Jalkanen S, Griffioen A W, Salmi M. (2010), J. Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in PCT/EP2009/062011 and PCT/EP2009/062018.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

DETAILED DESCRIPTION OF THE INVENTION

It has surprisingly been found that the compounds of formula (I) below are inhibitors of SSAO. They are therefore useful for the treatment or prevention of diseases in which inhibition of SSAO activity is beneficial, such as inflammation, inflammatory diseases, immune or autoimmune disorders, and inhibition of tumour growth.

According to the invention there is provided a compound of formula (I) or a pharmaceutically acceptable salt, or N-oxide thereof:

(I)

wherein $R^1$ is phenyl or 6-membered heteroaryl, optionally substituted with one or more substituents selected from halogen, cyano, $C_{1-4}$-alkyl, halo-$C_{1-4}$-alkyl, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, $NR^6C(O)NR^{4A}R^{4B}$, —$C(O)NR^{4A}R^{4B}$, —$C(O)R^5$, —$C(O)OR^5$, and —$NR^6S(O)_2R^5$;

A is a bond;

$R^2$ is —B-Q-$[R^3]_n$ or —B—$R^3$;

wherein n=1, 2, 3, or 4

B is a bond, O, $NR^4$, —C(O)— or $C_{1-3}$-alkylene;

Q is saturated or partially unsaturated monocyclic 3-7 membered heterocyclic or $C_{3-7}$-cycloalkyl ring;

when $R^2$ is —B-Q-$[R^3]_n$, $R^3$ is selected from hydrogen, halogen, cyano, amino, hydroxyl, oxo, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, $NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$NR^6S(O)_2R^5$, —$S(O)_2R^5$, phenyl-$C_{1-4}$-alkyl and heteroaryl-$C_{1-4}$-alkyl, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, $NR^6C(O)R^5$, —$NR^6C(O)NR^{4A}R^{4B}$, —$C(O)NR^{4A}R^{4B}$, —$C(O)R^5$, —$C(O)OR^5$, —$NR^6S(O)_2R^5$;

when $R^2$ is —B—$R^3$, $R^3$ is selected from amino, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$NR^6S(O)_2R^5$, phenyl-$C_{1-4}$-alkyl and heteroaryl-$C_{1-4}$-alkyl, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^D$, —$NR^6S(O)_2R^5$, provided that when $R^2$ is —B—$R^3$, and B is a bond and $R^3$ is —$C(O)R^5$, then $R^5$ is not hydrogen;

$R^{4A}$, $R^{4B}$ and $R^5$ are each independently selected from hydrogen, $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl or $C_{1-4}$alkoxy-$C_{1-4}$alkyl; or $R^{4A}$ and $R^{4B}$ together with the nitrogen to which they are attached form a cyclic amino group such as a piperidinyl, piperazinyl, N-substituted piperazinyl, morpholinyl or homopiperidinyl group;

$R^{4.A1}$ is selected from $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl or $C_{1-4}$alkoxy-$C_{1-4}$alkyl; or $R^{4.A1}$ and $R^{4B}$ together with the nitrogen to which they are attached form a cyclic amino group such as a piperidinyl, piperazinyl, N-substituted piperazinyl, morpholinyl or homopiperidinyl group;

$R^6$ is hydrogen or $C_{1-4}$-alkyl; and

X is selected from the radicals of formulae (1-16) wherein the bond marked * is attached to $R^1$A- and the bond marked ** is attached to —$R^2$:

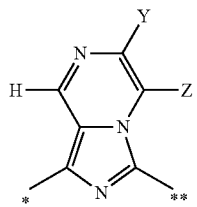

1

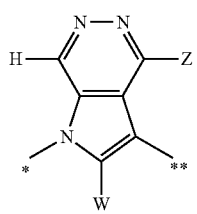

2

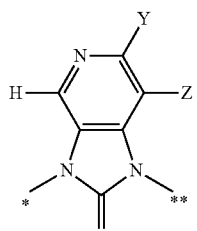

3

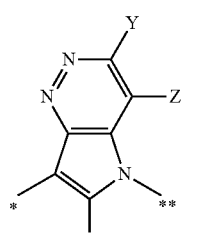

4

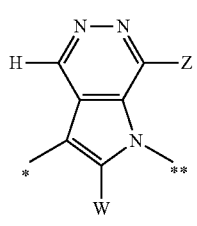

5

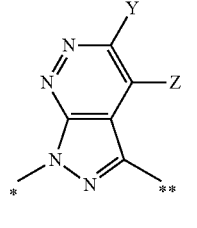

6

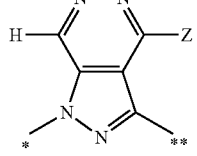

7

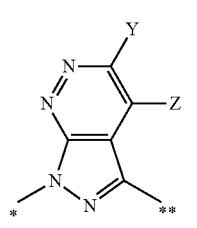

8

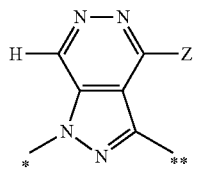

9

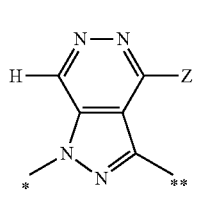

10

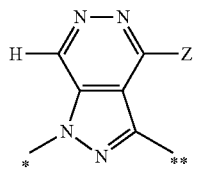

11

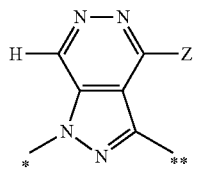

12

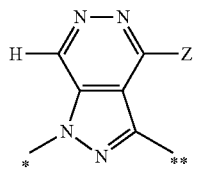

13

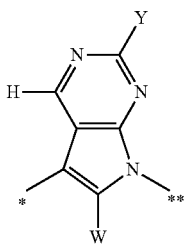

14

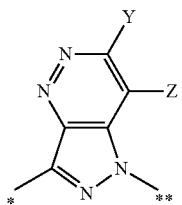

15

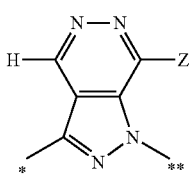

16

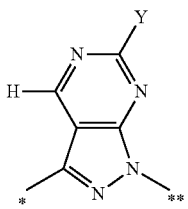

wherein Y is selected from hydrogen, hydroxyl, amino, —NHR⁶, —OCH₃;

Z is selected from hydrogen, fluorine, hydroxyl, $C_{1-4}$-alkoxy, halo-$C_{1-4}$-alkyl, CONH₂, cyano, SO₂NH₂, amino, —NHR⁶; and W is selected from H, $C_{1-4}$-alkyl, halo-$C_{1-4}$-alkyl;

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Since compounds of the invention have a nitrogen atom in an aromatic ring they may form N-oxides, and the invention includes compounds of the invention in their N-oxide form.

Definitions

The following definitions shall apply throughout the specification and the appended claims, unless otherwise stated or indicated.

The term "$C_{1-4}$-alkyl" denotes a straight or branched alkyl group having from 1 to 4 carbon atoms. For parts of the range $C_{1-4}$-alkyl all subgroups thereof are contemplated such as $C_{1-3}$-alkyl, $C_{1-2}$-alkyl, $C_{2-4}$-alkyl, $C_{2-3}$-alkyl and $C_{3-4}$-alkyl. Examples of said $C_{1-4}$-alkyl include methyl, ethyl, n-propyl, isopropyl, n-butyl, isobutyl, sec-butyl and tert-butyl.

The term "$C_{1-4}$-alkoxy" refers to a straight or branched $C_{1-4}$-alkyl group which is attached to the remainder of the molecule through an oxygen atom. For parts of the range $C_{1-4}$-alkoxy, all subgroups thereof are contemplated such as $C_{1-3}$-alkoxy, $C_{1-2}$-alkoxy, $C_{2-4}$-alkoxy, $C_{2-3}$-alkoxy and $C_{3-4}$-alkoxy. Examples of said $C_{1-4}$-alkoxy include methoxy, ethoxy, n-propoxy, isopropoxy, n-butoxy, isobutoxy, sec-butoxy and tert-butoxy.

The term "hydroxy-$C_{1-4}$-alkyl" denotes a straight or branched $C_{1-4}$-alkyl group that has one or more hydrogen atoms thereof replaced with OH. Examples of said hydroxy-$C_{1-4}$-alkyl include hydroxymethyl, 2-hydroxyethyl and 2,3-dihydroxypropyl.

The term "halo-$C_{1-4}$-alkyl" denotes a straight or branched $C_{1-4}$-alkyl group that has one or more hydrogen atoms thereof replaced with halogen. Examples of said halo-$C_{1-4}$-alkyl include fluoromethyl, trifluoromethyl, trichloromethyl and 2-fluoroethyl.

The term "cyano-$C_{1-4}$-alkyl" denotes a straight or branched $C_{1-4}$-alkyl group that has one or more hydrogen atoms thereof replaced with cyano. Examples of said cyano-$C_{1-4}$-alkyl include cyanomethyl, 2-cyanoethyl and 3-cyanopropyl.

The term "amino-$C_{1-4}$-alkyl" denotes a straight or branched $C_{1-4}$-alkyl group substituted with an amino group. Examples of said amino-$C_{1-4}$-alkyl group include aminomethyl and 2-aminoethyl.

The term "$C_{1-4}$-alkylamino-$C_{1-4}$-alkyl" denotes an amino-$C_{1-4}$-alkyl group as defined above, wherein the amino group is substituted with a straight or branched $C_{1-4}$-alkyl group. Examples of said $C_{1-4}$-alkylamino-$C_{1-4}$-alkyl include methylaminoethyl and ethylaminopropyl.

The term "di($C_{1-4}$-alkyl)amino-$C_{1-4}$-alkyl" denotes an amino-$C_{1-4}$-alkyl group as defined above, wherein the amino group is disubstituted with straight or branched $C_{1-4}$-alkyl groups, which can be the same or different. Examples of said di($C_{1-4}$-alkyl)amino-$C_{1-4}$-alkyl include N,N-dimethylaminomethyl, N-ethyl-N-methylaminoethyl and N,N-diethylaminomethyl.

The term "$C_{1-4}$-alkoxycarbonylamino-$C_{1-4}$-alkyl" denotes an amino-$C_{1-4}$-alkyl group as defined above, wherein the amino group is substituted with a straight or branched $C_{1-4}$-alkoxycarbonyl group, $C_{1-4}$-alkoxy-C(O)—. Examples of said $C_{1-4}$-alkoxycarbonylamino-$C_{1-4}$-alkyl include methoxycarbonylaminomethyl and tert-butoxycarbonylaminoethyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, pyrazolyl, pyridazinyl, pyrazinyl and thiadiazolyl.

The terms "heterocyclic" and "heterocyclic ring" include heteroaryl, and refer to a monocyclic ring structure having from 3 to 7 ring atoms, especially 5 or 6 ring atoms, in which one or more of the ring atoms are other than carbon, such as nitrogen, sulphur or oxygen. Examples of heterocyclic groups include those heteroaryl groups mentioned in the preceding paragraph, and piperidinyl, morpholinyl, homomorpholinyl, azepanyl, piperazinyl, oxo-piperazinyl, diazepinyl, tertahydropyridinyl, tetrahydropyranyl, pyrrolidinyl, tertrahydrofuranyl, and dihydropyrrolyl, groups.

The term "phenyl-$C_{1-4}$-alkyl" refers to a phenyl group that is directly linked to a straight or branched $C_{1-4}$-alkyl group. Examples of said phenyl-$C_{1-4}$-alkyl include phenylmethyl (i.e. benzyl), 2-phenylethyl and 2-phenylpropyl.

The term "heterocyclic-$C_{1-4}$-alkyl" refers to a heterocyclic ring that is directly linked to a straight or branched $C_{1-4}$-alkyl group via a carbon or nitrogen atom of said ring. Examples of said heterocyclic-$C_{1-4}$-alkyl include piperidin-4-ylmethyl, piperidin-1-ylmethyl, morpholin-4-yl-methyl and piperazin-4-ylmethyl.

The term "heteroaryl-$C_{1-4}$-alkyl" refers to a heteroaryl ring that is directly linked to a straight or branched $C_{1-4}$-alkyl group via a carbon or nitrogen atom of said ring. Examples of said heteroaryl-$C_{1-4}$-alkyl include pyrazolylmethyl, thiazolylmethyl and pyridinylethyl.

The term "$C_{1-3}$-alkylene" denotes a straight or branched divalent saturated hydrocarbon chain having from 1 to 3 carbon atoms. The $C_{1-3}$-alkylene chain may be attached to the rest of the molecule and to the radical group through one carbon within the chain or through any two carbons within the chain. Examples of $C_{1-3}$-alkylene radicals include methylene [—$CH_2$—], 1,2-ethylene [—$CH_2$—$CH_2$—], 1,1-ethylene [—$CH(CH_3)$—], 1,2-propylene [—$CH_2$—$CH(CH_3)$—] and 1,3-propylene [—$CH_2$—$CH_2$—$CH_2$—]. When referring to a "$C_{1-3}$-alkylene" radical, all subgroups thereof are contemplated, such as $C_{1-2}$-alkylene and $C_{2-3}$-alkylene.

"Halogen" refers to fluorine, chlorine, bromine or iodine, preferably fluorine and chlorine, most preferably fluorine.

"Hydroxy" refers to the —OH radical.

"Cyano" refers to the —CN radical.

"Oxo" refers to the carbonyl group =O.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, $2^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The Group X

In the compounds of the invention, X may be selected from any one of the radicals of formula 1-16.

Currently preferred embodiments of the invention include those where X is:
the formula 1 and $R^1$, $R^2$, Y, Z and W are as defined above; or
the formula 2 and $R^1$, $R^2$, Y, Z and W are as defined above; or
the formula 3 and $R^1$, $R^2$, Y, and Z are as defined above; or
the formula 4 and $R^1$, $R^2$, Y and W are as defined above; or
the formula 5 and $R^1$, $R^2$, and Y are as defined above; or
the formula 6 and $R^1$, $R^2$, Y, and Z are as defined above.

The Group B

In an embodiment of the invention, B is a bond, O, $NR^4$ such as NH, $NCH_3$, or $NCH_2CH_3$, —C(O)— or $C_{1-3}$alkylene such as methylene, ethylene or propylene radicals. In a currently preferred embodiment B is a bond, —C(O)— or methylene. In another preferred embodiment B is a bond.

The Group Y

In a currently preferred embodiment of the invention Y is selected from hydrogen, hydroxyl, amino ($NH_2$), —$NHR^6$ such as $NHCH_3$, $NHCH_2CH_3$, or —$OCH_3$. In another currently preferred embodiment Y is H, OH, or $NH_2$. In an alternative currently preferred embodiment Y is hydrogen The Group Z Z is selected from hydrogen, fluorine, hydroxyl, $C_{1-4}$-alkoxy such as methoxy or ethoxy, halo-$C_{1-4}$-alkyl such as fluoromethoxy, difluoromethyoxy or trimethoxy, $CONH_2$, cyano, $SO_2NH_2$, amino, —$NHR^6$ such as $NHCH_3$, $NHCH_2CH_3$. In a presently preferred embodiment of the invention Z is hydrogen or hydroxyl.

The Group W

In a currently preferred embodiment of the invention W is selected from H, $C_{1-4}$-alkyl such as methyl, ethyl, propyl, isopropyl, or halo-$C_{1-4}$-alkyl such as fluoromethyl, difluoromethyl or trifluoromethyl. In another currently preferred embodiment W is hydrogen.

The Group $R^1$

In one embodiment of the invention $R^1$ is phenyl or 6-membered heteroaryl such as pyridine, pyridazine, pyrimidine, pyrazine, optionally substituted with one or more substituents selected from halogen such as chloro or fluoro, cyano, $C_{1-4}$-alkyl such as methyl, ethyl, propyl or isopropyl, halo-$C_{1-4}$-alkyl such as fluoromethyl, difluoromethyl or trifluoromethyl, $C_{1-4}$alkoxy-$C_{1-4}$alkyl, hydroxy-$C_{1-4}$-alkyl such as hydroxylmethyl or hydroxylethyl, cyano-$C_{1-4}$-alkyl such as cyanomethyl or cyanoethyl, amino-$C_{1-4}$-alkyl such as aminomethyl, aminoethyl or aminopropyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^3$, —$NR^6C(O)NR^{4A}R^{4B}$, —$C(O)NR^{4A}R^{4B}$, —$C(O)R^5$, —$C(O)OR^5$, and —$NR^6S(O)_2R^5$.

In a currently preferred embodiment of the invention $R^1$ is optional substituted with one or more substituents selected from halogen such as fluoro or chloro, cyano, hydroxyl, $C_{1-4}$-alkyl such as methyl or ethyl, halo-$C_{1-4}$-alkyl such as fluoromethyl, difluoromethyl or trifluoromethyl, $C_{1-4}$alkoxy-$C_{1-4}$ alkyl, hydroxy-$C_{1-4}$-alkyl, cyano-$C_{1-4}$-alkyl such as cyanomethyl or cyanoethyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$.

In another currently preferred embodiment $R^1$ is heteroaryl such as pyridine-2-yl, pyridine-3-yl or pyridine-4-yl optionally substituted with one or more substituents selected from as fluoro, chloro, and $C_{1-4}$-alkyl such as methyl, ethyl, propyl, or isopropyl.

In an alternative embodiment $R^1$ is phenyl, optionally substituted at one or more of the para-, meta- and ortho-positions by one or more substituents selected from hydrogen, fluoro, chloro, cyano, hydroxyl, $C_{1-4}$-alkyl such as methyl, ethyl, propyl or isopropyl, or fluoromethyl, difluoromethyl, or trifluoromethyl.

In a currently preferred embodiment $R^1$ is phenyl substituted at the para position by a substituent selected from, fluoro, chloro, cyano, hydroxyl, $C_{1-4}$-alkyl such as methyl, ethyl, propyl or isopropyl, or fluoromethyl, difluoromethyl, or trifluoromethyl. In an alternative currently preferred embodiment the para substituent is selected from fluoro, chloro or methyl.

In another currently preferred embodiment $R^1$ is phenyl substituted at the meta-position by hydrogen.

In a further currently preferred embodiment $R^1$ is phenyl substituted at the ortho position by a substituent selected from hydrogen, fluoro, methyl, fluoromethyl, difluoromethyl, or trifluoromethyl. In another preferred embodiment $R^1$ is phenyl substituted at the ortho position by hydrogen, fluoro or methyl.

In a currently preferred embodiment of the invention $R^1$ is a mono, di, or tri substituted phenyl ring wherein the ortho, meta and/or para positions may be any combination of the substituents discussed above.

In a preferred embodiment the optional substituents of $R^1$ have a length of 4 atoms or fewer, preferably of 3 atoms or fewer, more preferably of 2 atoms or fewer.

The Group $R^2$

In one currently preferred embodiment of the invention $R^2$ is —B-Q-[$R^3$]$_n$. n can be 1, 2, 3, or 4. In another currently preferred embodiment n is 1 or 2.

The ring Q is a saturated or partially unsaturated monocyclic 3-7 membered heterocyclic or $C_{3-7}$-cycloalkyl ring substituted with $R^3$. In a currently preferred embodiment Q is a 7-membered saturated or partially unsaturated 7-membered heterocyclic ring such as a homomorpholine ring, or a bridged homomorpholine ring wherein the bridge is formed by an ethylene or propylene radical, or a 7-membered cycloalkyl ring such as cycloheptane.

In an alternative preferred embodiment Q is a 5- or 6-membered saturated or partially unsaturated 5 or 6 membered heterocyclic such as tetrahydrofuranyl, tetrahydropyranyl, piperidinyl, piperazinyl, morpholinyl, cyclohexyl, or any of the foregoing rings comprising a bridge formed by an ethylene or propylene radical, or a 5 or 6-membered cycloalkyl ring such cyclopentyl or cyclohexyl.

In a currently preferred embodiment $R^2$ is —B-Q-[$R^3$]$_n$, wherein $R^3$ is selected from hydrogen, halogen such as fluoro or chloro, cyano, amino (—$NH_2$), hydroxyl, oxo (═O), $C_{1-4}$-alkyl such as methyl, ethyl, propyl, isopropyl, butyl, halo-$C_{1-4}$-alky such as fluoromethyl, difluoromethyl or trifluoromethyl, $C_{1-4}$-alkoxy such as methoxy, ethoxy, propoxy or isopropoxy, $C_{1-4}$alkoxy-$C_{1-4}$alkyl such as methoxymethyl, methoxyethyl, or ethoxyethyl, hydroxy-$C_{1-4}$-alkyl such as hydroxymethyl or hydroxylethyl, cyano-$C_{1-4}$-alkyl such as cyanomethyl or cyanoethyl, amino-$C_{1-4}$-alkyl such as aminomethyl or aminoethyl, $C_{1-4}$-alkylamino-$C_{1-4}$-alkyl such as methylaminoethyl, di($C_{1-4}$-alkyl)amino-$C_{1-4}$-alkyl such as dimethylaminoethyl, —$NR^{4A}R^{4B}$ wherein $R^{4A}$ and $R^{4B}$ are, for example, hydrogen, methyl, or ethyl or taken with the nitrogen to which they are attached form a cyclic amino group such as piperidinyl, piperazinyl or morpholinyl, —$NR^6C(O)OR^5$, —$NR^6C(O)R^5$ wherein $R^6$ is hydrogen for example and $R^5$ is, for example methyl, ethyl or n- or iso-propy, —$NR^6C(O)NR^{4A}R^{4B}$ or —$C(O)NR^{4A}R^{4B}$ wherein $R^6$ is hydrogen for example and $R^{4A}$ and $R^{4B}$ are, for example, hydrogen, methyl, or ethyl or taken with the nitrogen to which they are attached form a cyclic amino group such as piperidinyl, piperazinyl or morpholinyl, —$C(O)R^5$ or —$C(O)OR^5$, —$NR^6S(O)_2R^5$, —$S(O)_2R^5$ wherein $R_5$ is, for example, hydrogen, methyl, ethyl, phenyl-$C_{1-4}$-alkyl such as benzyl or phenylethyl, and heteroaryl-$C_{1-4}$-alkyl having 5 or 6 ring atoms in the heteroaryl part, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —$NR^{4A}R^{4B}$, —$NR^6C(O)OR^5$, —$NR^6C(O)R^5$, $NR^6C(O)NR^{4A}R^{4B}$, —$C(O)NR^{4A}R^{4B}$, —$C(O)R^5$, —$C(O)OR^5$, —$NR^6S(O)_2R^5$;

In an alternative currently preferred embodiment $R^2$ is —B—$R^3$, wherein $R^3$ is selected from amino (—$NH_2$), $C_{1-4}$-alkoxy such as methoxy, ethoxy, propoxy or isopropoxy, $C_{1-4}$alkoxy-$C_{1-4}$alkyl such as methoxymethyl, methoxyethyl, or ethoxyethyl, hydroxy-$C_{1-4}$-alkyl such as hydroxymethyl or hydroxylethyl, cyano-$C_{1-4}$-alkyl such as cyanomethyl or cyanoethyl, amino-$C_{1-4}$-alkyl such as aminomethyl or aminoethyl, $C_{1-4}$-alkylamino-$C_{1-4}$-alkyl such as methylaminoethyl, di($C_{1-4}$-alkyl)amino-$C_{1-4}$-alkyl such as dimethylaminoethyl, —$NR^{4A}R^{4B}$, —$NR^6C(O)OR^5$, —$NR^6C(O)R^5$, —$NR^6C(O)NR^{4A}R^{4B}$, —$C(O)NR^{4A1}R^{4B}$, —$C(O)R^5$, —$NR^6S(O)_2R^5$, phenyl-$C_{1-4}$-alkyl and heteroaryl-$C_{1-4}$-alkyl, and wherein any phenyl or heteroaryl residue is optionally substituted with one or more substituents selected from halogen, cyano, $C_{1-4}$-alkyl, halo-$C_{1-4}$-alkyl, $C_{1-4}$-alkoxy, $C_{1-4}$alkoxy-$C_{1-4}$-alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl, —NR$^{4A}$R$^{4B}$, —NR$^{6}$C(O)OR$^{5}$, —NR$^{6}$C(O)R$^{5}$, —NR$^{6}$C(O)NR$^{4A}$R$^{4B}$, —C(O)NR$^{4A}$R$^{4B}$, —C(O)R$^{3}$, —C(O)OR$^{5}$, —NR$^{6}$S(O)$_{2}$R$^{5}$, provided that when R$^{2}$ is —B—R$^{3}$, and B is a bond and R$^{3}$ is —C(O)R$^{5}$, then R$^{5}$ is not hydrogen In the currently preferred embodiments of the invention R$^{4A}$, R$^{4B}$, R$^{5}$ and R$^{4A1}$ are as defined above.

In a currently preferred embodiment of the invention R$^{2}$ is selected from morpholine including morpholin-4-yl, morpholin-4-yl-methyl, oxolane including oxolan-3-yl, oxolan-3-yl-methyl, oxane including oxan-4-ylmethyl, oxan-4-yl, tetrahydropyridinyl, piperidine including piperidin-4-yl, piperidin-4-yl-methyl, oxo piperidine, piperazine including piperazin-1-yl, oxo piperazine, or piperazin-1-yl methyl, any of which being substituted by R$^{3}$ on the ring, or on the ring nitrogen in the 1-position.

In an alternative currently preferred embodiment R$^{2}$ is selected from:
(i) piperidine including piperidin-1-yl, pyrrolidine including pyrrolidin-1-yl, and cyclopropyl, cyclobutyl, cyclopentyl, or cyclohexyl any of which being substituted by R$^{3}$ on the ring.
(ii) a mono- or disubstituted amino group, the substituents being selected from $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, hydroxy-$C_{1-4}$-alkylamino-$C_{1-4}$-alkyl, di($C_{1-4}$-alkyl)amino-$C_{1-4}$-alkyl or $C_{1-4}$ alkoxy-$C_{1-4}$alkyl wherein in any of the foregoing an $C_{1-4}$alkyl part may be methyl, ethyl or n- or isopropyl and an $C_{1-4}$alkoxy part may be ethoxy or methoxy.
(iii) an $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl or di($C_{1-4}$-alkyl)amino-$C_{1-4}$-alkyl group wherein in any of the foregoing an $C_{1-4}$alkyl part may be methyl, ethyl or n- or isopropyl and an $C_{1-4}$alkoxy part may be ethoxy or methoxy.
(iv) morpholin-4-yl, morpholin-4-yl-methyl, 4-methoxycyclohexyl, 4-aminocyclohexyl, 4-tertbutoxycarbonylaminocyclohexyl, oxolan-3-yl, oxolan-3-ylmethyl, oxan-4-ylmethyl, oxan-4-yl, 3,6-dihydrooxan-4-yl, dimethylamino, N-(2-methoxyethyl)-N-methyl-amino, 1-hydroxyethylaminomethyl, piperidin-4-yl, 1-hydroxypiperidin-4-yl, 1-hydroxypiperidin-4-ylmethyl, 1-hydroxymethylpiperidin-4-yl, 1-hydroxyethylpiperidin-4-yl, 1-(3-cyanopropyl)piperidin-4-yl, 1-(3-cyanoethyl)piperidin-4-yl, 1-(1H-pyrazol-4-yl)methyl-piperidin-4-yl, 1-(1-methyl-1H-pyrazol-4-yl)methyl-piperidin-4-yl, 1-(3-aminopropan-1-one-1-yl)piperidin-4-yl, 1-(2-aminoethan-1-one-1-yl)piperidin-4-yl, 1-(2-dimethylaminoethan-1-one-1-yl)piperidin-4-yl, 1-(2-hydroxyethan-1-one-1-yl)piperidin-4-yl, 1-(3-(tertbutoxycarbonylamino)propan-1-one-1-yl)-piperidin-4-yl, 1-(2-(tertbutoxycarbonylamino)ethan-1-one-1-yl)-piperidin-4-yl, piperazin-1-yl, 4-methylpiperazin-1-yl, piperazin-1-yl-methyl, 4-methylpiperazin-1-yl-methyl, 4-methoxycarbonyl-piperazin-1-yl-methyl, hydroxymethyl, 2-hydroxyethyl, 1,2,3,6-tetrahydropyridin-4-yl, homomorpholin-4-yl, 2,2-dimethyl-morpholin-4-yl, 3,3-dimethyl-morpholin-4-yl, piperazin-2-one-4-yl, piperazine-2-one-5-yl, 8-oxa-3-azabicyclo[3.2.1]octane, 4-tertbutoxycarbonylpiperazin-1-yl-methyl, 3,3-difluoropyrrolidin-1-yl, 3-hydroxypyrrolidin-1-yl, 3-methoxypyrrolidin-1-yl, 4,4-difluoropiperidin-1-yl, 4-hydroxypiperidin-1-yl, 4-aminocarboxypiperidin-1-yl, 3-methylmorpholine-4-yl, 2-secbutylmorpholin-4-yl, (2S, 6R)-dimethyl morpholine-4-yl, 3-methyloxycarbonylmorpholin-4-yl, 1-methoxyethylaminomethyl, 2-aminomethylmorpholin-4-yl, 1-methoxyethylamino, 1-(3-aminoethylpropan-1-one)-piperazin-4-yl, 3-aminocarboxylmorpholin-4-yl, 3-(morpholine-4-carboxy)-morpholin-4-yl, 3-(1-aminoethyl-2-aminocarboxy)-morpholin-4-yl, morpholine-3-yl, morpholine-2-yl, 1-butylpiperidin-4-yl, 1-dimethylaminocarboxypiperidin-4-yl, 1-ethoxycarboxypiperidin-4-yl, 1-(4-aminobutan-1-one)piperidin-4-yl, 1-(2-aminoethoxycarboxy)piperidine-4-yl, 1-tertbutoxycarbonyl-lpiperidin-4-yl, formyl.

In any of the compounds of the invention, the R$^{2}$ group may be any one of the specific R$^{2}$ groups of the corresponding position of any of the examples described herein.

Specific currently preferred embodiments of the invention include:
4-[1-(4-Chlorophenyl)-1H-pyrrolo[2,3-c]pyridin-3-yl]cyclohexan-1-amine
1-{4-[1-(4-Chlorophenyl)-1H-pyrrolo[2,3-c]pyridine-3-yl] piperidin-1-yl}-2-hydroxyethan-1-one
2-Amino-1-{4-[1-(4-chlorophenyl)-1H-pyrrolo[2,3-c]pyridin-3-yl]piperidin-1-yl}ethan-1-one
3-Amino-1-{4-[1-(4-chlorophenyl)-1H-pyrrolo[2,3-c]pyridin-3-yl]piperidin-1-yl}propan-1-one
4-[3-(4-Methylphenyl)imidazo[1,5-a]pyrazin-1-yl]morpholine
4-[3-(4-Chlorophenyl)imidazo[1,5-a]pyrazin-1-yl]morpholine
3-(4-Chlorophenyl)-1-(oxan-4-yl)imidazo[1,5-a]pyrazine
1-(4-Chloro-2-fluorophenyl)-3-(oxan-4-yl)-1H-pyrazolo[3,4-c]pyridine
1-[1-(4-Chlorophenyl)-1H-pyrazolo[3,4-c]pyridin-3-yl]pyrrolidin-3-ol
3-Methoxy-1-[1-(4-methylphenyl)-1H-pyrazolo[3,4-c]pyridin-3-yl]pyrrolidine
1-[1-(4-Chlorophenyl)-1H-pyrazolo[3,4-c]pyridin-3-yl]piperidin-4-ol
1-[1-(4-Methylphenyl)-1H-pyrazolo[3,4-c]pyridin-3-yl]piperidine-4-carboxamide
4-[1-(4-Chlorophenyl)-1H-pyrazolo[3,4-c]pyridin-3-yl]morpholine
2,2,2-Trifluoroacetic acid; 4-[1-(4-methylphenyl)-1H-pyrazolo[3,4-c]pyridin-3-yl]morpholine
4-[1-(2-Fluoro-4-methylphenyl)-1H-pyrazolo[3,4-c]pyridin-3-yl]morpholine
4-[1-(4-Chlorophenyl)-1H-pyrazolo[3,4-c]pyridin-3-yl]-2-methylmorpholine
4-[1-(4-Chlorophenyl)-1H-pyrazolo[3,4-c]pyridin-3-yl]-3-methylmorpholine
3-[1-(4-Methylphenyl)-1H-pyrazolo[3,4-c]pyridin-3-yl]-8-oxa-3-azabicyclo[3.2.1]octane
2,2-Dimethyl-4-[1-(4-methylphenyl)-1H-pyrazolo[3,4-c]pyridin-3-yl]morpholine
Methyl 4-[1-(4-methylphenyl)-1H-pyrazolo[3,4-c]pyridin-3-yl]morpholine-3-carboxylate
4-[1-(4-Methylphenyl)-1H-pyrazolo[3,4-c]pyridin-3-yl]-1,4-oxazepane
4-[1-(4-Methylphenyl)-1H-pyrazolo[3,4-c]pyridin-3-yl]piperazin-2-one
1-[1-(4-Methylphenyl)-1H-pyrazolo[3,4-c]pyridin-3-yl]piperidin-4-ol
1-(4-Chlorophenyl)-3-(oxan-4-yl)-1H-pyrrolo[2,3-c]pyridine
1-(4-Methylphenyl)-3-(oxan-4-yl)-1H-pyrrolo[2,3-c]pyridine
4-[1-(4-Chlorophenyl)-1H-pyrrolo[2,3-c]pyridin-3-yl]morpholine 4-amino-1-{4-[1-(4-chlorophenyl)-1H-pyrrolo[2,3-c]pyridin-3-yl]piperidin-1-yl}butan-1-one 2-Aminoethyl 4-[1-(4-chlorophenyl)-1H-pyrrolo[2,3-c]pyridin-3-yl]piperidine-1-carboxylate 3-(3,6-Dihydro-2H-pyran-4-yl)-2-methyl-1-(4-methylphenyl)-1H-pyrrolo[2,3-c]pyridine or a pharmaceutically acceptable salt, or N-oxide thereof.

In one aspect, the invention relates to a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, or inhibition of tumour growth.

In particular, it is believed that compounds of formula (I) are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfusion injury), and myocardial infarction and/or the complications thereof.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

It is also believed that the compounds of the invention are especially useful for the treatment of rheumatoid arthritis, chronic obstructive pulmonary disease or atopic dermatitis.

In view of the evidence cited in the above introduction that VAP1 is up regulated in several cancers, including gastric cancer, melanoma, hepatoma and head and neck tumours and that mice bearing enzymatically inactive VAP-1 grow melanomas more slowly, and in view of the link between VAP1 and angiogenesis, it is also expected that the compounds of the invention are anti-angiogenic and therefore have utility in the treatment of cancers by inhibition of tumour growth.

The invention thus includes the compounds of formula (I) above for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Compositions

A currently preferred embodiment of the invention is a pharmaceutical composition comprising a compound of formula (I), together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Schemes. Definitions of variables in the structures in schemes herein are commensurate with those of corresponding positions in the formulas delineated herein.

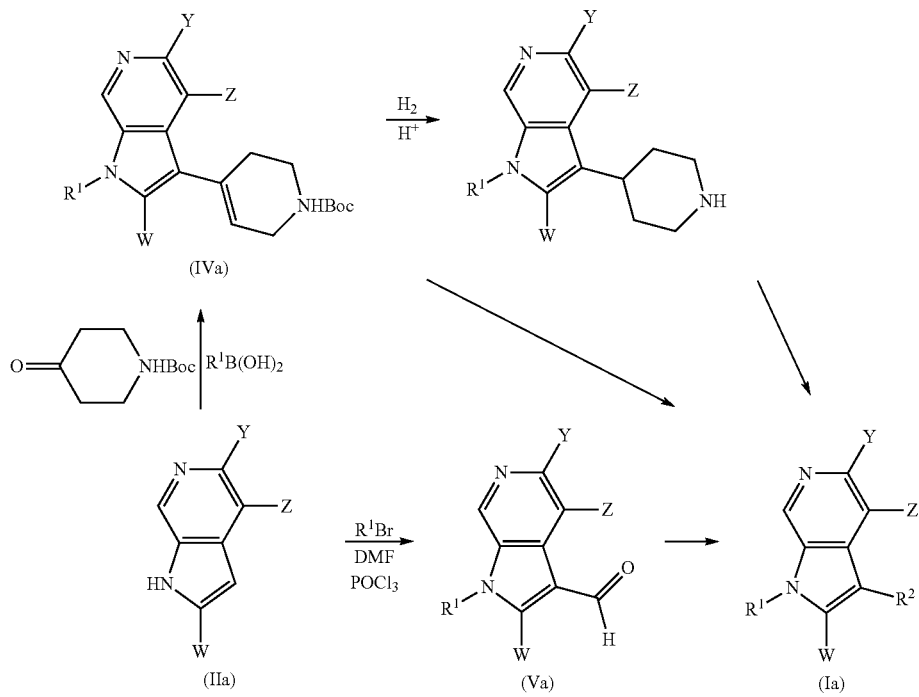

Scheme 1. General synthetic routes for preparation of compounds of formula (Ia)

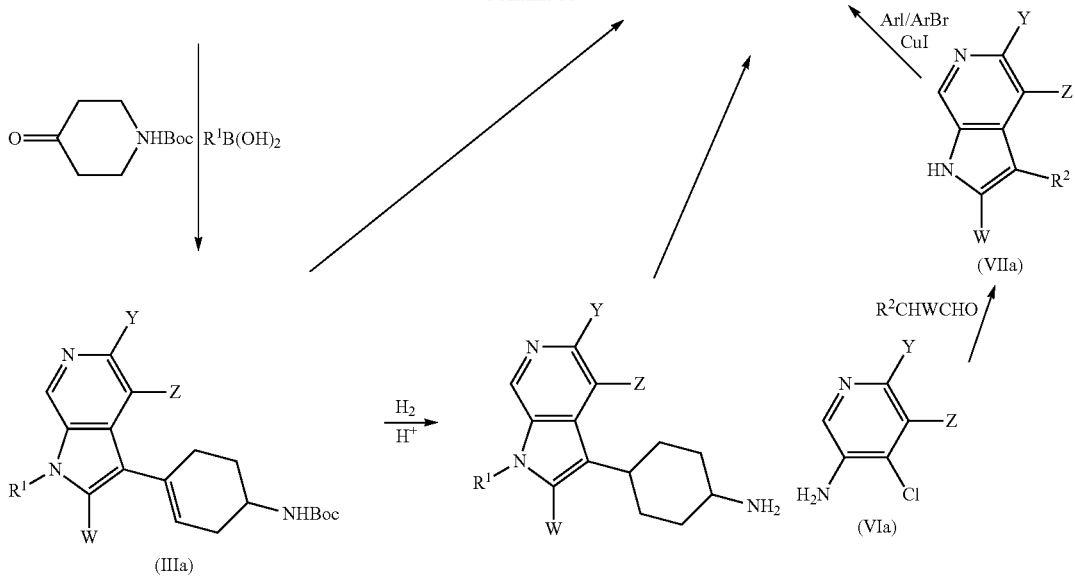

wherein W, Y, Z, R¹ and R² are as defined in formula (I);

Compounds of general formula (Ia) can easily be prepared from 1H-pyrrolo[2,3-c]pyridines (IIa) by either reaction with a ketone to introduce a functional group at R² followed by introduction of R¹ (for example by a Suzuki reaction) to give compounds of formula (IIIa/IVa), or by initial introduction of R¹ followed by introduction of a functional group at R² that can be modified to give alternative R², as in (Va). Compounds of formulae (IIIa), (IVa) and (Va) can easily be converted into compounds of general formula (Ia) by standard synthetic methods. Alternatively, 4-Chloro-3-aminopyridines (VIa) can be cyclised with the appropriate aldehyde to give compounds of general formula (VIIa) followed by introduction of R¹ (for example by an arylation reaction). The latter approach is known to those skilled in the art, for example in Xu et al., Synthesis, 24, 3981-3987, 2008.

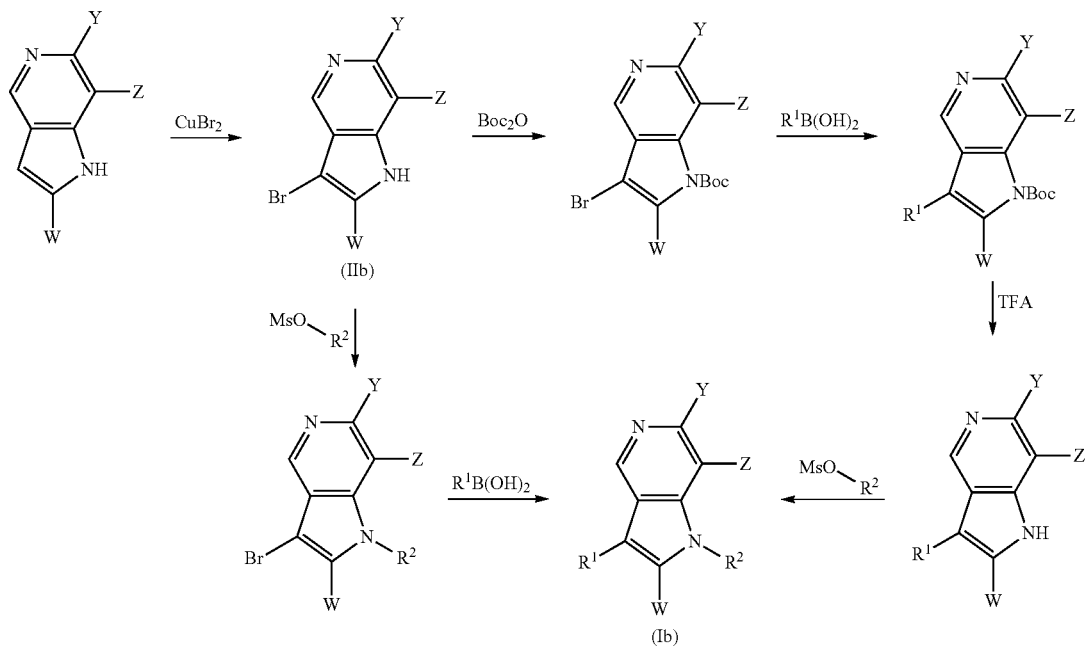

wherein W, Y, Z, R¹ and R² are as defined in formula (I);

Compounds of general formula (Ib) can easily be prepared from bromoindoles (IIb) by either introduction of R² (for example by nucleophilic substitution) followed by R¹ (for example by a Suzuki reaction), or by reversing these steps (with an appropriate protecting group strategy).

Scheme 3. General synthetic route for preparation of compounds of formula (Ic).

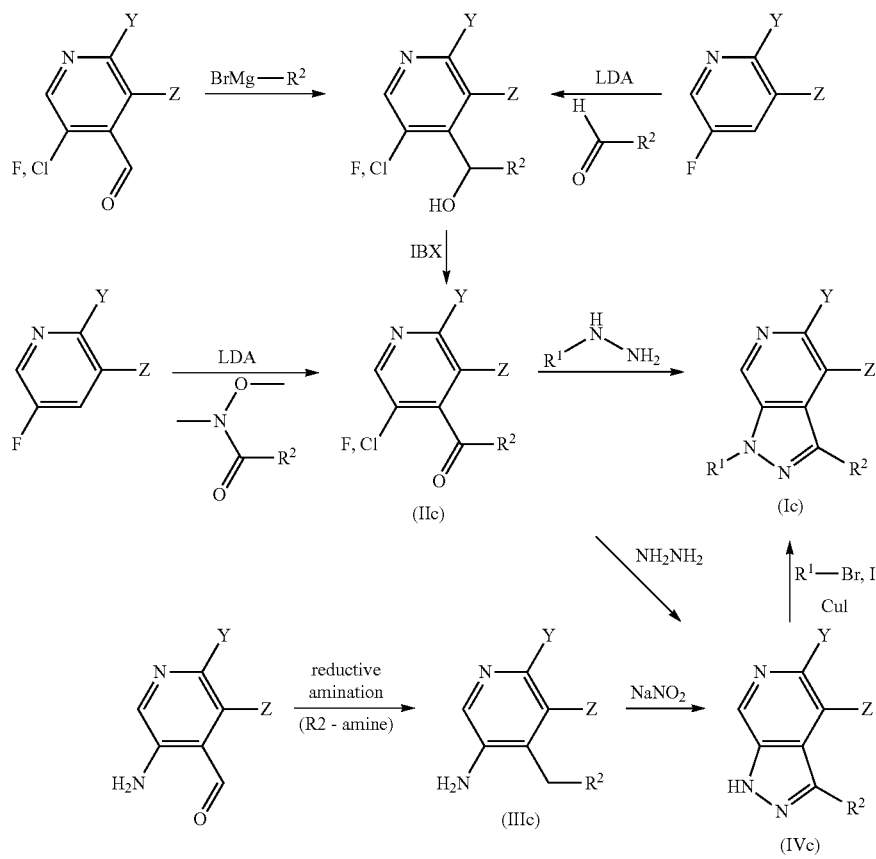

wherein Y, Z, $R^1$, $R^2$ and $R^3$ are as defined in formula (I);

Compounds of general formula (Ic) can easily be prepared according to standard methods known in the scientific literature, for example, by the cyclisation of 3-halo-4-[(pyridin-4-yl)carbonyl compounds of general formula (IIc) with hydrazines, or by cyclisation of compounds of general formula (IIIc) to give compounds of general formula (IVc), and subsequent introduction of $R^1$ (for example by an arylation reaction). Such methods are known to those skilled in the art, for example in Verma et al, Tet. Lett., 50, 383, 2009 and Zhu et al., BioOrg. Med. Chem. Lett., 15, 2441-2452, 2007.

Scheme 4. General synthetic route for preparation of compounds of formula (Id).

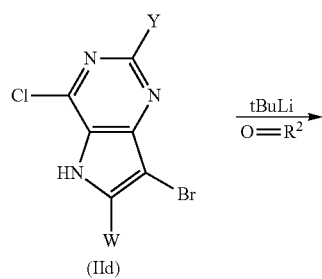

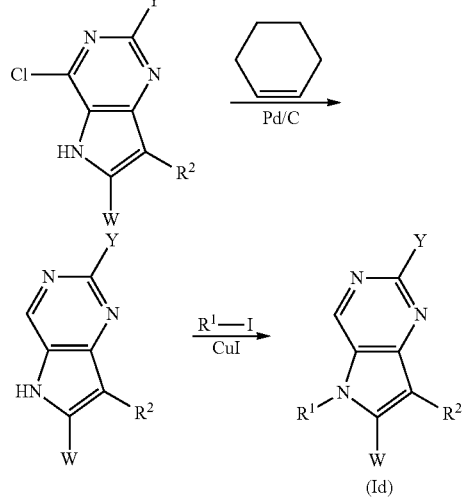

wherein W, Y, $R^1$ and $R^2$ are as defined in formula (I);

Compounds of general formula (Id) can easily be prepared according to standard methods known in the scientific literature, for example, by lithiation of 7-bromo-4-chloro-5H-pyrrolo[3,2-d]pyrimidines (IId) and reaction with an aldehyde, followed by reduction and subsequent introduction of $R^1$ (for example by an arylation reaction). Such methods are known to those skilled in the art, for example in WO2008070507 and Antilla et al., JOC, 69, 5578, 2004.

Scheme 5. General synthetic route for preparation of compounds of formula (Ie).

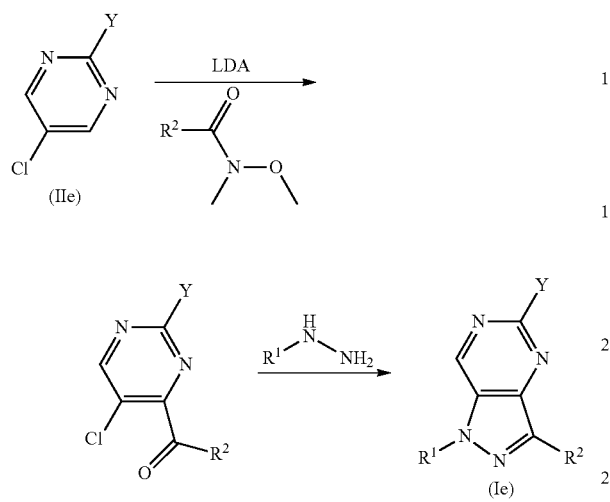

wherein Y, $R^1$ and $R^2$ are as defined in formula (I);

Compounds of general formula (Ie) can easily be prepared according to standard methods known in the scientific literature, for example, by condensation of 5-chloropyrimidines (IIe) with a Weinreb amide and subsequent reaction with a hydrazine. Such methods are known to those skilled in the art, for example in WO2003039469 and Verma et al, Tet. Lett., 50, 383, 2009.

Scheme 6. General synthetic route for preparation of compounds of formula (If).

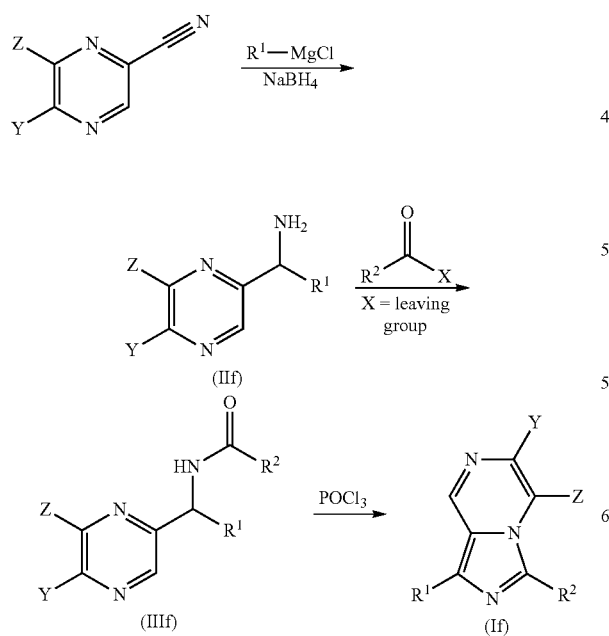

wherein Y, Z, $R^1$ and $R^2$ are as defined in formula (I);

Compounds of general formula (If) can easily be prepared by the condensation of pyrazine-2-carbonitriles with a Grignard reagent to give amine intermediates (IIf). Functionalisation of amines (IIf) to give amides or ureas of general formula (IIIf) and cyclisation with phosphorus oxychloride gives compounds of general formula (If).

Scheme 7. General synthetic route for preparation of compounds of formula (Ig).

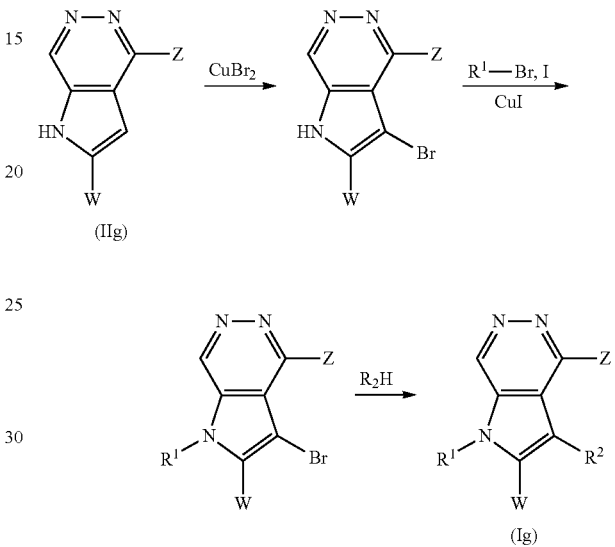

wherein W, Z, $R^1$ and $R^2$ are as defined in formula (I);

Compounds of general formula (Ig) can be prepared from 1H-pyrrolo[2,3-d]pyridazines (IIg) by bromination with CuBr (for example, as described in Gallou et al., Syn. Lett., 2, 211-214, 2007) and subsequent introduction of $R^1$ (for example by an arylation reaction) and $R^2$ (for example by a Buchwald-Hartwig reaction).

Scheme 8. General synthetic route for preparation of compounds of formula (Ih).

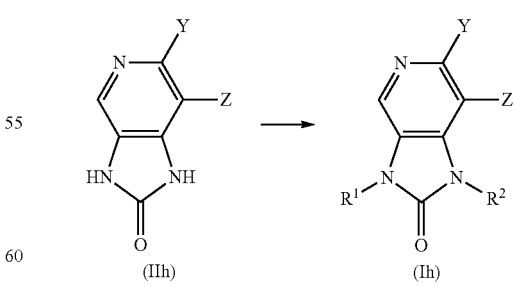

wherein Y, Z, $R^1$ and $R^2$ are as defined in formula (I);

Compounds of general formula (Ih) can be prepared by sequential alkylations of 1H,2H,3H-imidazo[4,5-c]pyridin-2-ones (IIh), for example as described in WO2008054749.

Scheme 9. General synthetic route for preparation of compounds of formula (Ii).

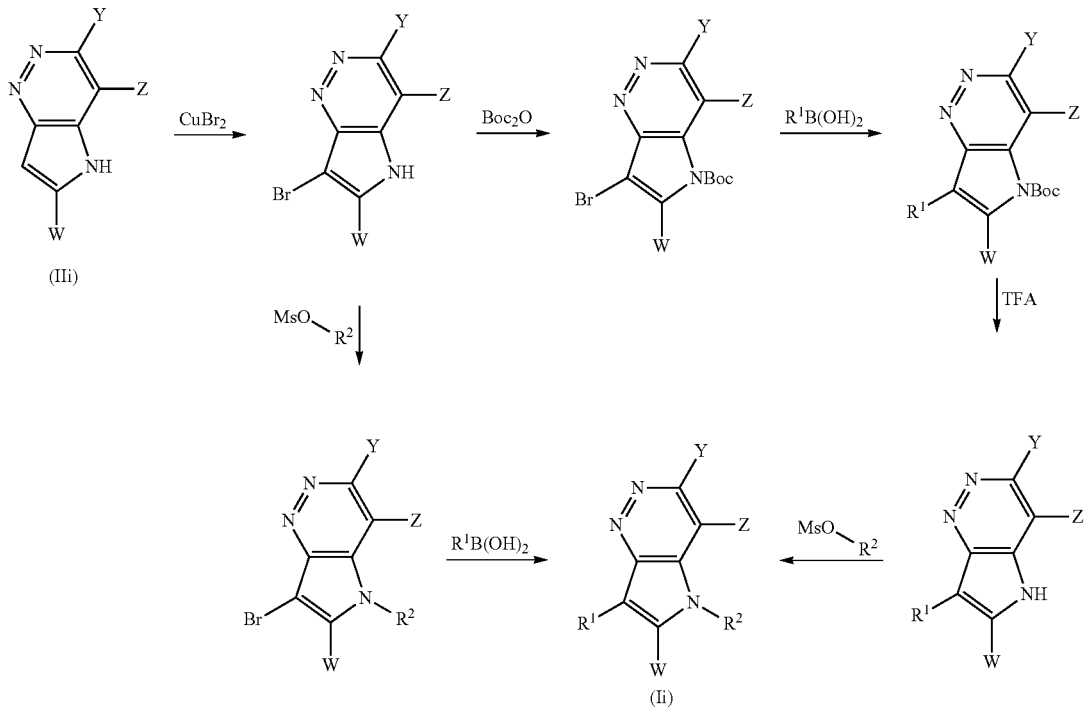

wherein W, Y, Z, R¹ and R² are as defined in formula (I);

Compounds of general formula (Ii) can be prepared from 1H-pyrrolo[2,3-d]pyridazines (IIi) by bromination with CuBr (for example, as described in Gallou et al., Syn. Lett., 2, 211-214, 2007) followed by either introduction of R² (for example by nucleophilic substitution) followed by R¹ (for example by a Suzuki reaction), or by reversing these steps (with an appropriate protecting group strategy).

wherein W, Z, R¹ and R² are as defined in formula (I);

Compounds of general formula (Ij) can be prepared from 1H-pyrrolo[2,3-d]pyridazines (IIj) by bromination with CuBr (for example, as described in Gallou et al., Syn. Lett., 2, 211-214, 2007) followed by either introduction of R² (for example by nucleophilic substitution) followed by R¹ (for example by a Suzuki reaction), or by reversing these steps (with an appropriate protecting group strategy).

Scheme 10. General synthetic route for preparation of compounds of formula (Ij).

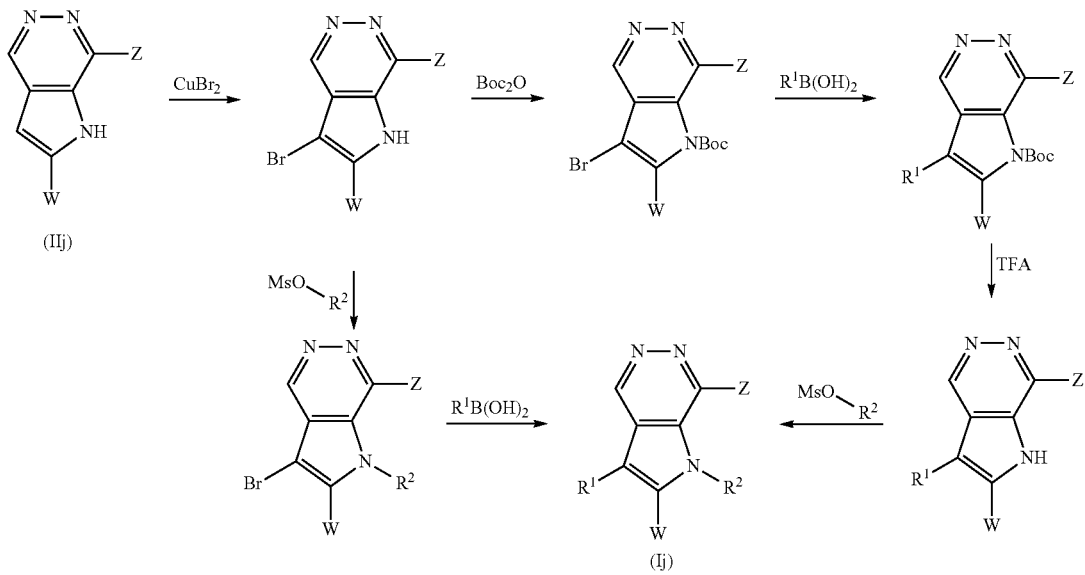

Scheme 11. General synthetic route for preparation of compounds of formula (Ik).

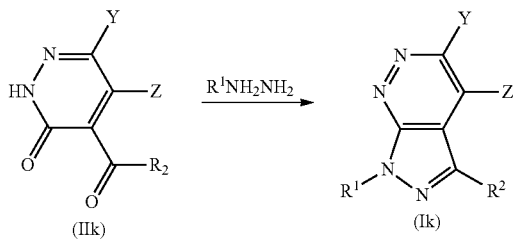

wherein Y, Z, $R^1$ and $R^2$ are as defined in formula (I);

Compounds of general formula (Ik) can be prepared by cyclisation of compounds of general formula (IIk) with hydrazines, for example, as described in Deeb et al., Journal of the Chinese Chemical Society, 37(3), 287-94; 1990.

Scheme 12. General synthetic route for preparation of compounds of formula (Il).

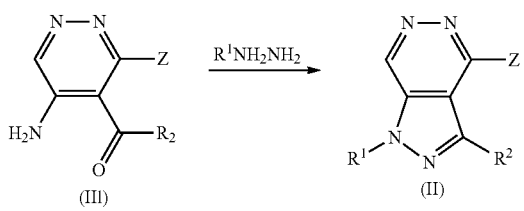

wherein Z, $R^1$ and $R^2$ are as defined in formula (I);

Compounds of general formula (II) can be prepared by cyclisation of compounds of general formula (III) with hydrazines, for example, as described in Haider et al., Journal of the Chemical Society, Perkin Transactions 1: Organic and Bio-Organic Chemistry, 1, 169-72; 1986.

Scheme 13. General synthetic route for preparation of compounds of formula (Im).

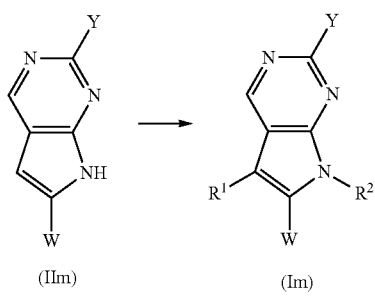

wherein W, Y, $R^1$ and $R^2$ are as defined in formula (I);

Compounds of general formula (Im) can be prepared by sequential alkylation/arylation of 7H-pyrrolo[2,3-d]pyrimidines (IIm), for example as described in WO2009080682.

Scheme 14. General synthetic route for preparation of compounds of formula (In).

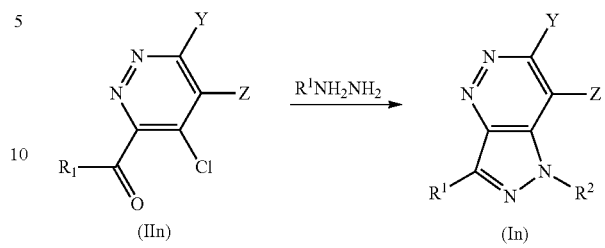

wherein Y, Z, $R^1$ and $R^2$ are as defined in formula (I);

Compounds of general formula (In) can be prepared by cyclisation of compounds of general formula (IIn) with hydrazines, for example, as described in Filaok et al., Journal of Organic Chemistry, 73(10), 3900-3906, 2008.

Scheme 15. General synthetic route for preparation of compounds of formula (Io).

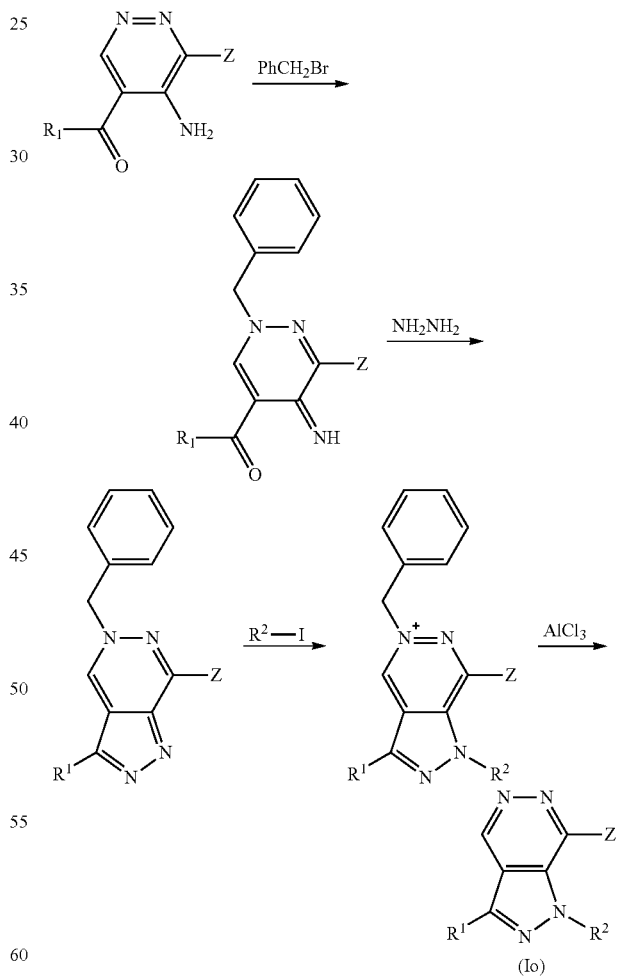

wherein Z, $R^1$ and $R^2$ are as defined in formula (I);

Compounds of general formula (Io) can be prepared according to Scheme 15, for example as described in Haider et al., Journal of the Chemical Society, Perkin Transactions 1: Organic and Bio-Organic Chemistry, 1, 169-72; 1986.

Scheme 16. General synthetic route for
preparation of compounds of formula (Ip).

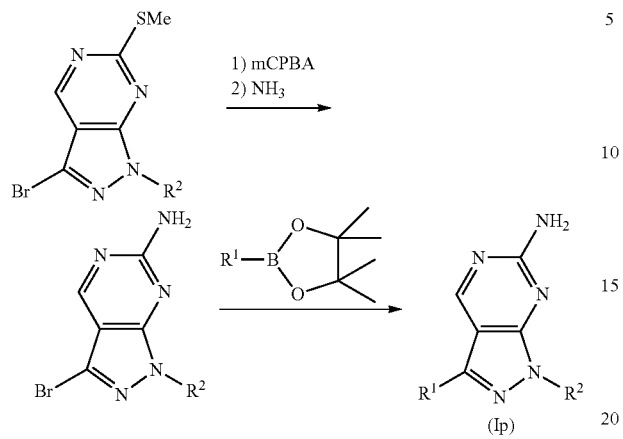

wherein R¹ and R² are as defined in formula (I);

Compounds of general formula (Ip) can be prepared according to Scheme 16, for example as described in WO 2007134828.

Optionally, a compound of formula (I) can also be transformed into another compound of formula (I) in one or more synthetic steps.

The following abbreviations have been used:
Ac acetyl
AcOH acetic acid
aq aqueous
Ar aryl
Boc tert-butoxycarbonyl
calcd calculated
cat catalytic
conc concentrated
d day
DCE dichloroethane
DCM dichloromethane
DIPEA diisopropylethylamine
DMA dimethylacetamide
DMF dimethylformamide
EDC 1-ethyl-3-(3-dimethylaminopropyl)carbodiimide hydrochloride
ESI electrospray ionization
EtOAc ethyl acetate
EtOH ethanol
h hour(s)
HBTU O-benzotriazole-N,N,N',N'-tetramethyl-uronium-hexafluoro-phosphate
HOBT 1-hydroxybenzotriazole hydrate
HPLC High Performance Liquid Chromatography
HRMS High-Resolution Mass Spectrometry
IBX 2-Iodoxybenzoic acid
Int Intermediate
LDA lithium diisopropylamide
M molar
mCPBA meta-chloroperbenzoic acid
Me methyl
MeCN Acetonitrile
MeOH methanol
min minute(s)
Ms methanesulfonate
MS Mass Spectrometry
NaBH(OAc)₃ sodium triacetoxyborohydride
NMP N-methylpyrrolidone
Pd₂(dba)₃ tris(dibenzylideneacetone)dipalladium(0)
Ph phenyl
PhMe toluene
r.t. room temperature
SCX Strong Cation Exchange
SM starting material
tBuLi tert-butyllithium
tBuOH tert-butanol
TFA trifluoroacetic acid
THF tetrahydrofuran
TsOH p-toluenesulfonic acid
X-Phos 2-dicyclohexylphosphino-2',4',6'-triisopropylbiphenyl

EXAMPLES AND INTERMEDIATE COMPOUNDS

Experimental Methods

Reactions were conducted at room temperature unless otherwise specified. Microwave reactions were performed with a Personal Chemistry/Biotage microwave reactor using process vials fitted with aluminum caps and septa. Hydrogenations were performed using a Thales H-Cube. Preparative flash chromatography was performed on Merck silica gel 60 (230-400 mesh) or using a Flash Master Personal system equipped with Strata SI-1 silica gigatubes. Reverse phase column chromatography was performed on a Gilson system (Gilson 321 pump and Gilson FC204 fraction collector) equipped with Merck LiChroprep® RP-18 (40-63 um) columns. Reverse Phase HPLC was performed on a Gilson system with a UV detector equipped with Phenomenex Synergi Hydro RP 150×10 mm, or YMC ODS-A 100/150×20 mm columns, or on an XTerra Prep MS C18 5 μm 19×50 mm system. The purest fractions were collected, concentrated and dried under vacuum. The methanesulfonate intermediates were prepared from the corresponding alcohols and methanesulfonyl chloride and triethylamine in DCM. Compounds were typically dried in a vacuum oven at 40° C. prior to purity analysis. Compound analysis was performed by HPLC/LCMS using either an Agilent 1100/1200 Series Liquid Chromatograph/Mass Selective Detector (MSD) (Single Quadrupole) (1946A/1946C/1956C/6110) equipped with an electrospray interface or using an Agilent 1100 HPLC system/Waters ZQ mass spectrometer connected to an Agilent 1100 HPLC system with either an ACE 3 C8 column (50×3.0 mm, 1 mL per min, gradient 10-97% MeCN in water (+0.1% TFA) over 3 min, 215-395 nm, method A) or a Phenomenex Synergi, RP-Hydro column (150×4.6 mm, 4 μm, 1.5 mL per min, 30° C., gradient 5-100% MeCN (+0.085% TFA) in water (+0.1% TFA) over 7 min, 200-300 nm, method B). Accurate masses (HRMS) were measured using either an Agilent MSD-TOF connected to an Agilent 1100 HPLC system (during the analyses the calibration was checked by two masses and automatically corrected when needed. Spectra were acquired in positive electrospray mode. The acquired mass range was m/z 100-1100. Profile detection of the mass peaks was used), or using a Thermo Scientific LTQ Orbitrap XL equipped with an Advio TriVersa NanoMate electrospray ion source (during the analyses the calibration was checked by three masses. Spectra were acquired in positive electrospray mode. The acquired mass range was m/z 100-2000. Samples were dissolved in DMSO to give 10 mM solutions which were then further diluted with MeOH or 10 mM NH₄OAc in MeOH to ~0.1M solutions prior to analysis). The compounds prepared were named using ACD Name 6.0, 7.0 or 10.0.

Intermediate 1

3-Bromo-1H-pyrrolo[3,2-c]pyridine

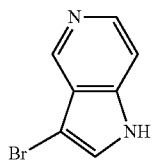

5-Azaindole (118 mg, 1.00 mmol) and copper(II) bromide (669 mg, 3.00 mmol) were mixed with MeCN (10 mL) and stirred for 1.5 h. To the mixture was added 2 M ammonia in MeOH (12 mL) and the resulting suspension was added to water (40 mL) and extracted with EtOAc (2×60 mL). The organic layers were combined and washed with brine and evaporated to yield the title compound (190 mg, 32%). MS (ESI+) m/z=197, 199 (M+H)$^+$.

Intermediate 2 tert-Butyl 3-bromo-1H-pyrrolo[3,2-c]pyridine-1-carboxylate

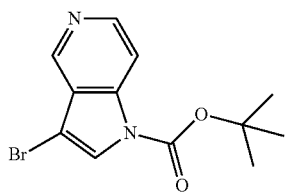 [SMILES: CC(C)(C)OC(=O)n1cc(Br)c2cnccc21]

To a mixture of Intermediate 1 (1.80 g, 9.14 mmol) in DCM (60 mL) was added di-tert-butyl dicarbonate (2.18 g, 10.0 mmol) followed by 4-dimethylaminopyridine (122 mg, 1.00 mmol). After 80 min the solution was diluted with DCM (20 mL) and washed with 0.1 M HCl (25, 10 mL) and brine. The organic layer was dried (Na$_2$SO$_4$), filtered and evaporated to yield the title compound as a light yellow solid (2.47 g, 90%). MS (ESI+) m/z=299 (M+H)$^+$.

Intermediate 3 tert-Butyl 3-(4-chlorophenyl)-1H-pyrrolo[3,2-c]pyridine-1-carboxylate

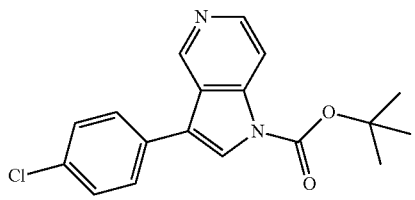 [SMILES: CC(C)(C)OC(=O)n1cc(-c2ccc(Cl)cc2)c2cnccc21]

Intermediate 2 (33.0 mg, 0.10 mmol) was mixed with 80% aqueous dimethoxyethane (1 mL), 4-chlorophenylboronic acid (23.0 mg, 0.15 mmol) and K$_2$CO$_3$ (35.0 mg, 0.25 mmol). Tetrakis-(triphenylphosphine)palladium(0) (6.00 mg, 0.005 mmol) was added and the mixture was stirred at 80° C. for 80 min. After cooling, water (0.8 mL) and EtOAc (8 mL) were added. The mixture was centrifuged and the organic layer was separated. Flash chromatography (1:3 EtOAc/toluene) gave the title compound (21 mg, 64%). HRMS (ESI+) calcd for C$_{18}$H$_{17}$ClN$_2$O$_2$ 328.0979. found 328.0980.

Intermediate 4

3-(4-Chlorophenyl)-1H-pyrrolo[3,2-c]pyridine

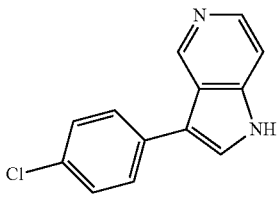 [SMILES: Clc1ccc(-c2c[nH]c3ccncc23)cc1]

Intermediate 3 (2.20 g, 6.68 mmol) was mixed with DCM (20 mL) and TFA (10 mL, 130 mmol). After 3 h the mixture was evaporated and then co-evaporated with MeOH (3×). The residue was dissolved in EtOAc (80 mL) and washed with 10% aq. Na$_2$CO$_3$ (3×20 mL) and brine. The organic layer was dried (Na$_2$SO$_4$) and concentrated to yield the title compound (1.48 g, 97%). MS (ESI+) m/z=229, 231.

Intermediate 5 tert-Butyl 4-(3-bromo-1H-pyrrolo[3,2-c]pyridin-1-yl)piperidine-1-carboxylate

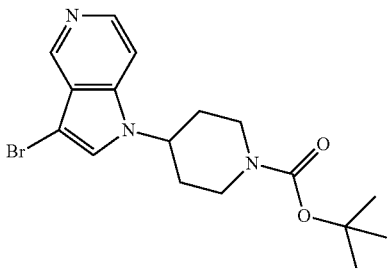 [SMILES: CC(C)(C)OC(=O)N1CCC(n2cc(Br)c3cnccc32)CC1]

Intermediate 1 (394 mg, 1.99 mmol), tert-butyl 4-[(methylsulfonyl)oxy]piperidine-1-carboxylate (614 mg, 2.20 mmol) and Cs$_2$CO$_3$ (1.30 g, 4.00 mmol) in DMF (10 mL) was heated at 80° C. overnight. Most of the solvent was evaporated and the residue was purified by flash chromatography (3% MeOH in CHCl$_3$) to give the title compound as an off-white solid (260 mg, 34%). MS (ESI+) m/z=380, 382 (M+H)$^+$.

Intermediate 6 tert-Butyl 4-[3-(3,4-dichlorophenyl)-1H-pyrrolo[3,2-c]pyridin-1-yl]piperidine-1-carboxylate

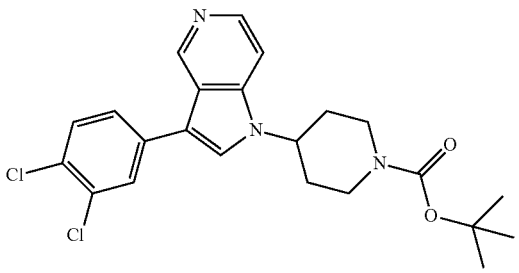 [SMILES: CC(C)(C)OC(=O)N1CCC(n2cc(-c3ccc(Cl)c(Cl)c3)c3cnccc32)CC1]

A mixture of Intermediate 5 (38.0 mg, 0.10 mmol), K₂CO₃ (34.0 mg, 0.25 mmol), tetrakis(triphenylphosphine)palladium(0) (6.00 mg, 0.005 mmol) and 3,4-dichlorophenyl-boronic acid (23.0 mg, 0.12 mmol) in 1,4-dioxane (0.8 mL) and water (0.2 mL) was heated at 80° C. for 3 h. The crude product was purified by preparative HPLC to give the title compound as a white solid (12 mg, 27%). HRMS (ESI+) calcd for $C_{23}H_{25}Cl_2N_3O_2$ 445.1324. found 445.1336.

Intermediate 7 tert-Butyl 4-{1H-pyrrolo[2,3-c]pyridin-3-yl}-1,2,3,6-tetrahydropyridine-1-carboxylate

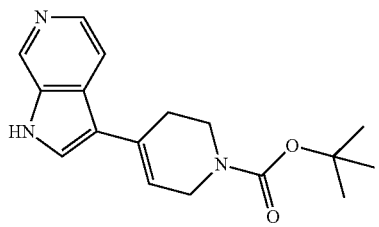 [SMILES: CC(C)(C)OC(=O)N1CC=C(c2c[nH]c3cnccc23)CC1]

A suspension of 1H-pyrrolo[2,3-c]pyridine (0.95 g, 8.05 mmol), tert-butyl 4-oxo-piperidine-1-carboxylate (1.70 g, 8.54 mmol) and KOH (0.95 g, 17.0 mmol) in MeOH (10 mL) was heated at reflux overnight. The mixture was added to ice-water (50 mL) and then MeOH (50 mL) was added. The resulting solution was concentrated to circa 50 mL and then extracted three times with DCM/MeOH (9:1, 50 mL). The organic layers were combined and concentrated and the residue was purified by flash chromatography (9:1 DCM/MeOH) to yield the title compound as a light yellow solid (2.21 g, 92%). MS (ESI+) m/z=300 (M+H)⁺.

Intermediate 8 tert-Butyl 4-[1-(4-chlorophenyl)-1H-pyrrolo[2,3-c]pyridin-3-yl]-1,2,3,6-tetrahydropyridine-1-carboxylate

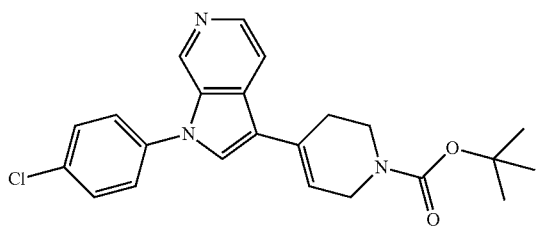 [SMILES: CC(C)(C)OC(=O)N1CC=C(c2cn(-c3ccc(Cl)cc3)c3cnccc23)CC1]

A suspension of Intermediate 7 (30.0 mg, 0.10 mmol), (4-chlorophenyl)boronic acid (16.0 mg, 0.10 mmol), copper (II) acetate (18.0 mg, 0.10 mmol) and triethylamine (20.0 mg, 0.20 mmol) in DCM (1 mL) was stirred for 72 h. The mixture was concentrated and then purified by preparative HPLC to yield the title compound (5.20 mg, 13%). MS (ESI+) m/z=410, 412 (M+H)⁺.

Intermediate 9 tert-Butyl 4-{1H-pyrrolo[2,3-c]pyridin-3-yl}piperidine-1-carboxylate

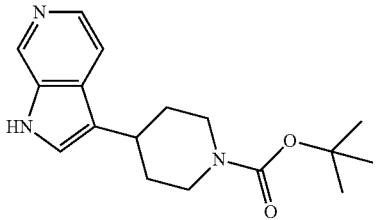 [SMILES: CC(C)(C)OC(=O)N1CCC(c2c[nH]c3cnccc23)CC1]

A suspension of Intermediate 7 (598 mg, 2.00 mmol) and 10% Pd/C (cat) in EtOH (3 mL) and cyclohexene (1.5 mL) was heated at 150° C. for 25 min in a microwave reactor. The mixture was filtered and evaporated to yield the title compound as a colourless oil (540 mg, 89%). MS (ESI+) m/z=302 (M+H)⁺.

Intermediate 10 tert-Butyl N-(4-{1H-pyrrolo[2,3-c]pyridin-3-yl}cyclohex-3-en-1-yl)carbamate

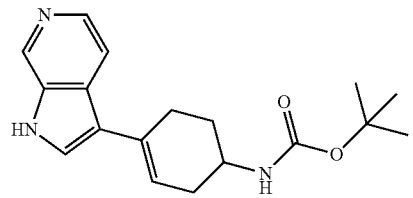 [SMILES: CC(C)(C)OC(=O)NC1CC=C(c2c[nH]c3cnccc23)CC1]

A suspension of 1H-pyrrolo[2,3-c]pyridine (0.95 g, 8.05 mmol), tert-butyl (4-oxocyclohexyl)carbamate (1.82 g, 8.54 mmol) and KOH (0.95 g, 17.0 mmol) in MeOH (10 mL) was heated at reflux overnight. The solution was added to ice-water (50 mL) and then MeOH (50 mL) was added. The resulting solution was concentrated to circa 50 mL and extracted three times with DCM/MeOH (9:1, 50 mL) and the organic layers were combined and concentrated. The residue was purified by flash chromatography (9:1 DCM/MeOH) to give the title compound as a white solid (1.96 g, 78%). MS (ESI+) m/z=314 (M+H)⁺.

Intermediate 11 tert-Butyl N-(4-{1H-pyrrolo[2,3-c]pyridin-3-yl}cyclohexyl)carbamate

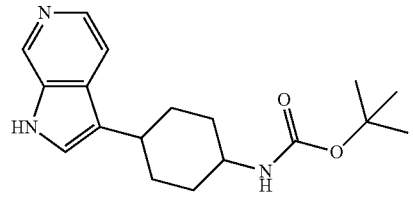 [SMILES: CC(C)(C)OC(=O)NC1CCC(c2c[nH]c3cnccc23)CC1]

A suspension of Intermediate 10 (235 mg, 0.75 mmol) and 10% Pd/C (cat) in EtOH (2.5 mL) and cyclohexene (1 mL) was heated at 140° C. for 20 min in a microwave reactor. The mixture was filtered and concentrated to yield a diastereoisomeric mixture of the title compound (229 mg, 97%). MS (ESI+) m/z=316 (M+H)⁺.

Intermediate 12 tert-Butyl N-{4-[1-(4-chloro-2-methylphenyl)-1H-pyrrolo[2,3-c]pyridin-3-yl]-cyclohexyl}carbamate

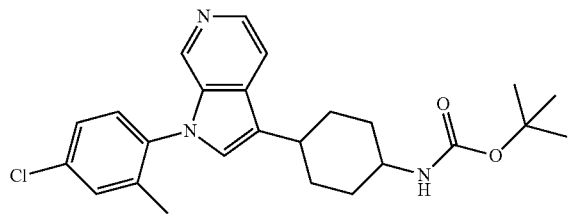 [SMILES: Cc1cc(Cl)ccc1-n1cc(C2CCC(NC(=O)OC(C)(C)C)CC2)c2ccncc21]

A suspension of Intermediate 11 (32.0 mg, 0.10 mmol), (4-chloro-2-methylphenyl)boronic acid (17.0 mg, 0.10 mmol), copper(II) acetate (18.0 mg, 0.10 mmol) and triethylamine (20.0 mg, 0.20 mmol) in DCM (1 mL) was stirred for 72 h. The mixture was concentrated and then purified by preparative HPLC to yield a diastereoisomeric mixture of the title compound (1.30 mg, 2.9%). MS (ESI+) m/z=440, 442 (M+H)⁺.

Intermediate 13

1-(4-Chlorophenyl)-1H-pyrrolo[2,3-c]pyridine

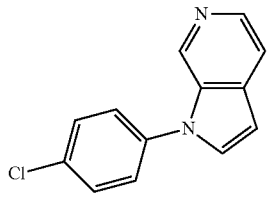 [SMILES: Clc1ccc(-n2ccc3ccncc32)cc1]

A suspension of 1H-pyrrolo[2,3-c]pyridine (1.18 g, 10.0 mmol), 1-bromo-4-chlorobenzene (2.87 g, 15.0 mmol), copper(I) iodide (95.0 mg, 0.50 mmol), K₃PO₄ (4.46 g, 21.0 mmol) and trans-diaminocyclohexane (250 µL, 2.00 mmol) in 1,4-dioxane (15 mL) was heated to reflux for 5 days. The mixture was concentrated and the residue was purified by flash chromatography (EtOAc) to yield the title compound as a light brown solid (2.08 g, 90%). MS (ESI+) m/z=229, 231 (M+H)⁺.

Intermediate 14

(4-Chlorophenyl)(pyrazin-2-yl)methanamine

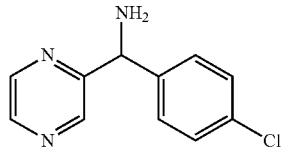 [SMILES: NC(c1ccc(Cl)cc1)c1cnccn1]

Pyrazine-2-carbonitrile (10.5 g, 100 mmol) was dissolved in PhMe (100 mL) at 0° C. and 4-chlorophenyl magnesium bromide (100 ml, 1.0 M in Et₂O, 100 mmol) was added portion-wise over 5 min. The reaction mixture was stirred for 6 h and NaBH₄ (7.58 g, 201 mmol) and tBuOH (100 mL) were added. The reaction mixture was warmed to 60° C. for 18 h and quenched with 1 M aq NaOH solution. The aqueous layer was extracted with EtOAc and the combined organic layers were dried (MgSO₄) and concentrated in vacuo. The residue was purified by flash chromatography (DCM:EtOH:NH3 200:8:1 to 50:8:1) to give the title compound as a brown oil (7.46 g, 34%). MS (ESI+) m/z=220.0 (M+H)⁺.

Intermediate 15

(4-Methylphenyl)(pyrazin-2-yl)methanamine

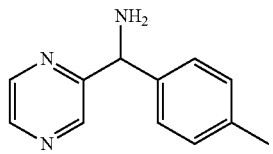

The title compound was prepared as a crude brown oil (890 mg, 9%), similarly to Intermediate 14, using p-toluoyl magnesium bromide instead of 4-chlorophenyl magnesium bromide.

Intermediate 16

N-[(4-Methylphenyl)(pyrazin-2-yl)methyl]morpholine-4-carboxamide

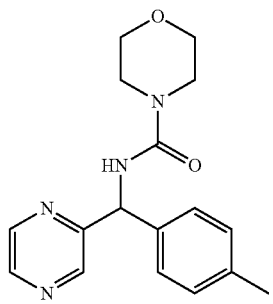 [SMILES: Cc1ccc(C(NC(=O)N2CCOCC2)c2cnccn2)cc1]

Intermediate 15 (890 mg, 4.47 mmol) and DIPEA (0.93 mL, 5.36 mmol) were dissolved in DCM (20 mL). 4-Morpholinecarbonyl chloride (0.56 mL, 4.91 mmol) was added and the reaction mixture was stirred for 2 d. The reaction mixture was diluted with DCM, washed with 1 M aq HCl and 1 M aq Na₂CO₃, dried (MgSO₄) and concentrated in vacuo. The crude product was purified by flash chromatography (1-2% MeOH in DCM) to give the title compound as a yellow gum (690, 49% mg). MS (ESI+) m/z=313.5 (M+H)⁺.

Intermediate 17

N-[(4-Chlorophenyl)(pyrazin-2-yl)methyl]morpholine-4-carboxamide

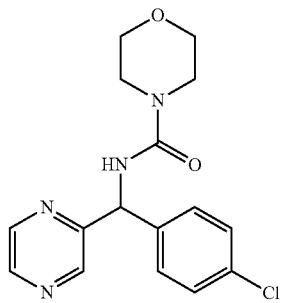 [SMILES: O=C(NC(c1ccc(Cl)cc1)c1cnccn1)N1CCOCC1]

Intermediate 14 (1.83 g, 8.33 mmol) and DIPEA (1.59 mL, 9.16 mmol) were dissolved in DCM (40 mL). 4-Morpholinecarbonyl chloride (1.05 mL, 9.16 mmol) was added and the reaction mixture was stirred for 3 d. The reaction mixture was diluted with DCM, washed with 1 M aq HCl and 1 M aq Na$_2$CO$_3$, dried (MgSO$_4$) and concentrated in vacuo to give the crude title compound as a brown solid (2.55 g, 92%). MS (ESI+) m/z=333.0 (M+H)$^+$.

Intermediate 18

1-[(4-Chlorophenyl)(pyrazin-2-yl)methyl]-3-(2-methoxyethyl)-3-methylurea

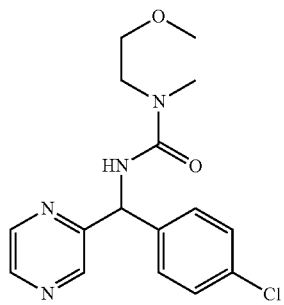 [SMILES: COCCN(C)C(=O)NC(c1ccc(Cl)cc1)c1cnccn1]

N-(2-Methoxyethyl)methylamine (203 mg, 2.28 mmol) was dissolved in DCM (10 mL) at 0° C. and DIPEA (417 µl, 2.39 mmol) was added. Triphosgene (223 mg, 0.75 mmol) was added and the reaction mixture was stirred at 0° C. for 1 h. A solution of Intermediate 14 (500 mg, 2.28 mmol) and DIPEA (417 µl, 2.39 mmol) in DCM (10 mL) was added and the reaction mixture was stirred at r.t. for 64 h. The reaction mixture was diluted with DCM, washed with sat aq NaHCO$_3$, sat aq NH$_4$Cl and brine, dried (MgSO$_4$) and concentrated in vacuo. The residue was purified by reverse phase column chromatography (20-100% MeOH in water) to give the crude title compound which was used without further purification in the synthesis of Example 37.

Intermediate 19

1-[(4-Chlorophenyl)(pyrazin-2-yl)methyl]-3,3-dimethylurea

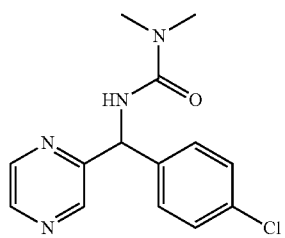 [SMILES: CN(C)C(=O)NC(c1ccc(Cl)cc1)c1cnccn1]

Intermediate 14 (440 mg, 2.00 mmol) and DIPEA (0.42 mL, 2.40 mmol) were dissolved in DCM (20 mL). Dimethylcarbamyl chloride (0.20 mL, 2.20 mmol) was added and the reaction mixture was stirred for 3 d. Further dimethylcarbamyl chloride (0.10 mL, 1.10 mmol) was added and the reaction mixture was stirred for 6 h. The reaction mixture was diluted with DCM, washed with 1 M aq HCl and 1 M aq Na$_2$CO$_3$, dried (MgSO$_4$) and concentrated in vacuo to give the crude title compound as a red oil (510 mg, 88%). MS (ESI+) m/z=291.3 (M+H)$^+$.

Intermediate 20

N-[(4-Chlorophenyl)(pyrazin-2-yl)methyl]oxane-4-carboxamide

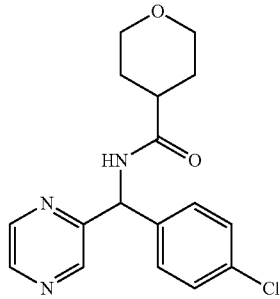 [SMILES: O=C(NC(c1ccc(Cl)cc1)c1cnccn1)C1CCOCC1]

Intermediate 14 (490 mg, 2.23 mmol), tetrahydropyran-4-carboxylic acid (319 mg, 2.45 mmol) and DIPEA (0.43 mL, 2.23 mmol) were dissolved in DMF (10 mL) and HBTU (930 mg, 2.45 mmol) was added. The reaction mixture was stirred for 3 d and concentrated in vacuo. The reaction mixture was dissolved in EtOAc, washed with 1 M aq HCl and 1 M aq Na$_2$CO$_3$, dried (MgSO$_4$) and concentrated in vacuo to give the crude title compound as a light brown gum (514 mg, 69%). MS (ESI+) m/z=332.4 (M+H)$^+$.

Intermediate 21

N-[(4-Chlorophenyl)(pyrazin-2-yl)methyl]-2-(oxan-4-yl)acetamide

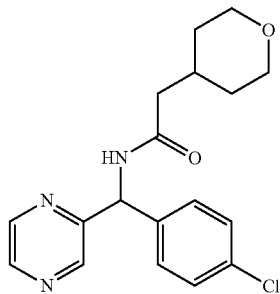 [SMILES: O=C(CC1CCOCC1)NC(c1ccc(Cl)cc1)c1cnccn1]

The title compound was prepared as a crude brown oil (419 mg, 53%), similarly to Intermediate 20, using tetrahydropyran-4-yl-acetic acid instead of tetrahydropyran-4-carboxylic acid. MS (ESI+) m/z=346.1 (M+H)$^+$.

Intermediate 22

N-[(4-Chlorophenyl)(pyrazin-2-yl)methyl]oxolane-3-carboxamide

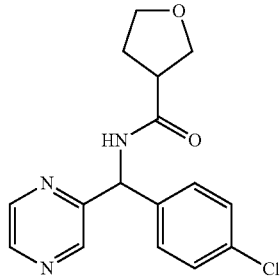 [SMILES: O=C(NC(c1ccc(Cl)cc1)c1cnccn1)C1CCOC1]

The title compound was prepared as a crude brown oil (465 mg, 61%), similarly to Intermediate 20, using tetrahydro-3-furoic acid instead of tetrahydropyran-4-carboxylic acid. MS (ESI+) m/z=318.0 (M+H)+.

Intermediate 23

N-[(4-Chlorophenyl)(pyrazin-2-yl)methyl]-4-methoxycyclohexane-1-carboxamide

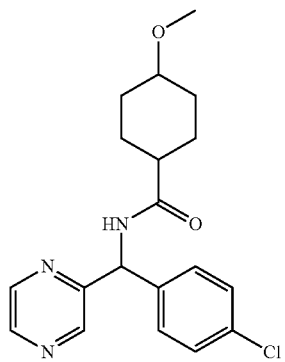 [SMILES: COC1CCC(C(=O)NC(c2ccc(Cl)cc2)c2cnccn2)CC1]

The title compound (523 mg) was prepared similarly to Intermediate 20, using 4-methoxycyclohexane carboxylic acid instead of tetrahydropyran-4-carboxylic acid, as a crude brown oil which was used without further purification.

Intermediate 24

N-Methoxy-N-methyloxane-4-carboxamide

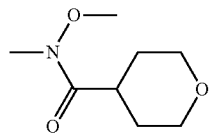

N,O-Dimethylhydroxylamine hydrochloride (1.23 g, 12.7 mmol) and N-methylmorpholine (3.80 mL, 34.5 mmol) were dissolved in DCM (20 mL) and a solution of oxane-4-carbonyl chloride (1.71 g, 11.5 mmol) in DCM (20 mL) was added drop-wise. The reaction mixture was stirred for 2 h, then diluted to 200 mL with DCM, washed with 1 M aq HCl (2×100 mL), 1M aq Na$_2$CO$_3$ (100 mL) and water (100 mL), dried (MgSO$_4$) and concentrated in vacuo to give the crude title compound as a yellow oil (1.87 g, 94%). LCMS (ES+): 174.1 (M+H)+.

Intermediate 25

3-Fluoro-4-[(oxan-4-yl)carbonyl]pyridine

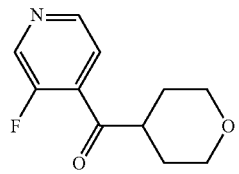

Diisopropylamine (1.50 ml, 10.8 mmol) was dissolved in THF (30 mL) and cooled to −78° C. under nitrogen. nBuLi (4.32 mL, 2.5 M in hexanes, 10.8 mmol) was added drop-wise and the resulting solution was stirred at −78° C. for 10 min, at 0° C. for 30 min and then re-cooled to −78° C. 3-Fluoro-pyridine (0.93 mL, 10.8 mmol) was added drop-wise over 5 min and the reaction mixture was stirred for 2 h. A solution of Intermediate 24 (1.87 g, 10.8 mmol) in THF (15 mL) was added and the reaction mixture was allowed to warm to room temperature and stirred for 15 min. The reaction mixture was quenched with sat aq NH$_4$OAc (10 mL) and diluted with EtOAc (200 mL). The organic fraction was washed with water (2×50 mL), dried (MgSO$_4$) and concentrated in vacuo to give the crude title compound as an orange oil (1.45 g, 64%). LCMS (ES+): 210.1 (M+H)+.

Intermediate 26

3-(Oxan-4-yl)-1H-pyrazolo[3,4-c]pyridine

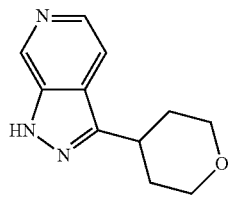

Intermediate 25 (255 mg, 1.22 mmol) and hydrazine monohydrate (134 mg, 2.68 mmol) were dissolved in NMP (3 mL) and the reaction mixture was heated in a microwave at 160° C. for 20 min. The reaction mixture was purified by SCX chromatography to give the title compound as an orange oil (245 mg, 99%). LCMS (ES+): 204.1 (M+H)+.

Intermediate 27

4-[(3,3-Difluoropyrrolidin-1-yl)methyl]pyridin-3-amine

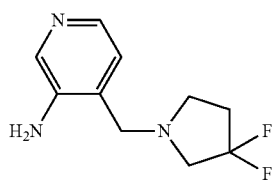 [SMILES: Nc1cnccc1CN1CCC(F)(F)C1]

3-Amino-pyridine-4-carbaldehyde (250 mg, 2.05 mmol) was dissolved in DCM (4 mL) and MeOH (4 mL), and 3,3-difluoropyrrolidine hydrochloride (353 mg, 2.46 mmol) and NaBH(OAc)$_3$ (521 mg, 2.46 mmol) were added. The reaction mixture was stirred for 18 h, quenched with water (5 mL) and the solvents were removed in vacuo. The residue was dissolved in DCM (20 mL) and washed with sat aq Na$_2$CO$_3$ (5 mL). The aqueous phase was extracted with DCM (3×20 mL) and the combined organic fractions were dried (MgSO$_4$) and concentrated in vacuo to give the crude title compound as a yellow gum (246 mg, 56%). LCMS (ES+): 214.0 (M+H)+.

Intermediates 28-50

Intermediates 28-50 were prepared similarly to Intermediate 27, by reacting 3-amino-pyridine-4-carbaldehyde with the appropriate amine; see Table 1 below.

TABLE 1

Preparation of pyridin-3-amino intermediates

| Int | Structure | Crude yield | LCMS (ES+) | Intermediate Name |
|-----|-----------|-------------|------------|-------------------|
| 28 | 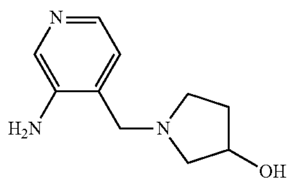 [SMILES: Nc1cnccc1CN1CCC(O)C1] | 58% | 194.1 (M + H)+ | 1-[(3-Aminopyridin-4-yl)methyl]pyrrolidin-3-ol |
| 29 | 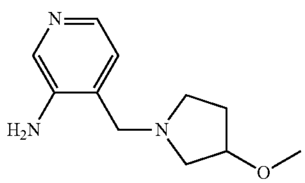 | 67% | 208.0 (M + H)+ | 4-[(3-Methoxypyrrolidin-1-yl)methyl]pyridin-3-amine |
| 30 | 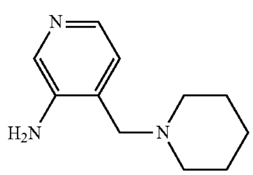 [SMILES: Nc1cnccc1CN1CCCCC1] | 48% | 192.1 (M + H)+ | 4-(Piperidin-1-ylmethyl)pyridin-3-amine |
| 31 | 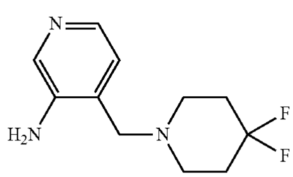 [SMILES: Nc1cnccc1CN1CCC(F)(F)CC1] | 63% | 228.0 (M + H)+ | 4-[(4,4-Difluoropiperidin-1-yl)methyl]pyridin-3-amine |
| 32 | 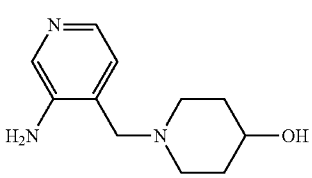 [SMILES: Nc1cnccc1CN1CCC(O)CC1] | 46% | 208.0 (M + H)+ | 1-[(3-Aminopyridin-4-yl)methyl]piperidin-4-ol |
| 33 | 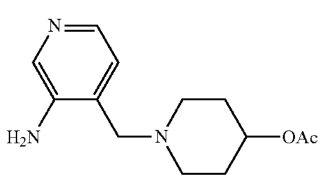 [SMILES: CC(=O)OC1CCN(Cc2ccncc2N)CC1] | 42% | 250.1 (M + H)+ | 1-[(3-Aminopyridin-4-yl)methyl]piperidin-4-yl acetate |
| 34 | 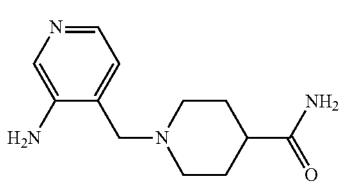 [SMILES: NC(=O)C1CCN(Cc2ccncc2N)CC1] | 48% | 235.1 (M + H)+ | 1-[(3-Aminopyridin-4-yl)methyl]piperidine-4-carboxamide |

TABLE 1-continued

Preparation of pyridin-3-amino intermediates

| Int | Structure | Crude yield | LCMS (ES+) | Intermediate Name |
|---|---|---|---|---|
| 35 | 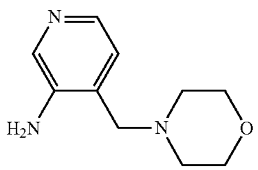 [SMILES: Nc1cnccc1CN1CCOCC1] | 63% | 194.1 (M + H)+ | 4-(Morpholin-4-ylmethyl)pyridin-3-amine |
| 36 | 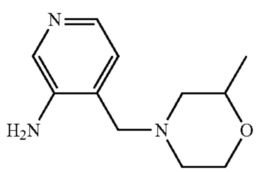 | 45% | 208.1 (M + H)+ | 4-[(2-Methylmorpholin-4-yl)methyl]pyridin-3-amine |
| 37 | 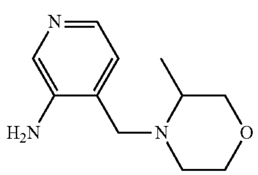 | 83% | 208.1 (M + H)+ | 4-[(3-Methylmorpholin-4-yl)methyl]pyridin-3-amine |
| 38 | 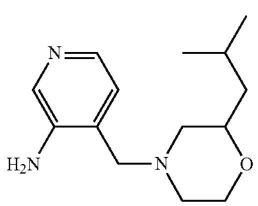 [SMILES: CC(C)CC1CN(Cc2ccncc2N)CCO1] | 100% | 250.1 (M + H)+ | 4-{[2-(2-Methylpropyl)morpholin-4-yl]methyl}pyridin-3-amine |
| 39 | 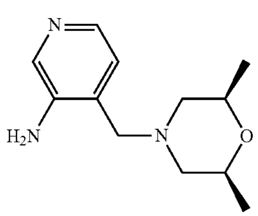 [SMILES: C[C@@H]1CN(Cc2ccncc2N)C[C@H](C)O1] | 72% | 222.1 (M + H)+ | 4-{[(2R,6S)-2,6-Dimethylmorpholin-4-yl]methyl}pyridin-3-amine |
| 40 | 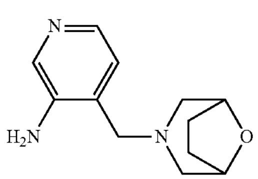 | 70% | 220.0 (M + H)+ | 4-{8-Oxa-3-azabicyclo[3.2.1]octan-3-ylmethyl}pyridin-3-amine |
| 41 | 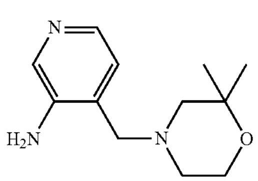 [SMILES: CC1(C)CN(Cc2ccncc2N)CCO1] | 99% | 222.1 (M + H)+ | 4-[(2,2-Dimethylmorpholin-4-yl)methyl]pyridin-3-amine |

TABLE 1-continued

Preparation of pyridin-3-amino intermediates

| Int | Structure | Crude yield | LCMS (ES+) | Intermediate Name |
|---|---|---|---|---|
| 42 | 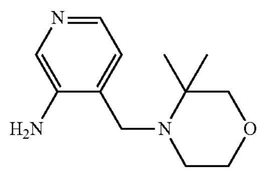 [SMILES: CC1(C)COCCN1Cc1ccncc1N] | 100% | 222.1 (M + H)+ | 4-[(3,3-Dimethylmorpholin-4-yl)methyl]pyridin-3-amine |
| 43 | 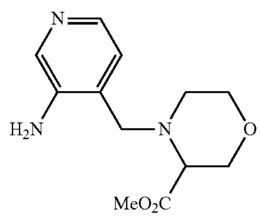 [SMILES: COC(=O)C1COCCN1Cc1ccncc1N] | 79% | 252.1 (M + Na)+ | Methyl 4-[(3-aminopyridin-4-yl)methyl]morpholine-3-carboxylate |
| 44 | 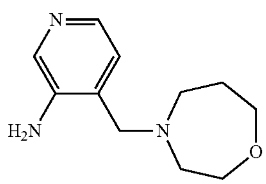 [SMILES: Nc1cnccc1CN1CCCOCC1] | 92% | 208.0 (M + H)+ | 4-(1,4-Oxazepan-4-ylmethyl)pyridin-3-amine |
| 45 | 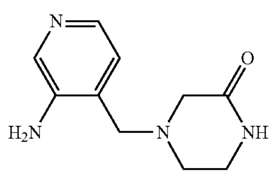 [SMILES: Nc1cnccc1CN1CCNC(=O)C1] | 75% | 207.0 (M + H)+ | 4-[(3-Aminopyridin-4-yl)methyl]piperazin-2-one |
| 46 | 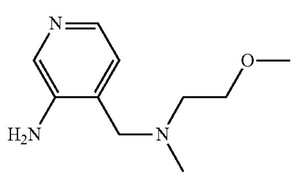 | 84% | 196.1 (M + H)+ | 4-{[(2-Methoxyethyl)(methyl)amino]methyl}pyridin-3-amine |
| 47 | 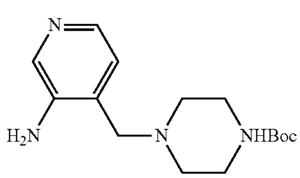 | 70% | 293.1 (M + H)+ | tert-Butyl 4-[(3-aminopyridin-4-yl)methyl]piperazine-1-carboxylate |

TABLE 1-continued

Preparation of pyridin-3-amino intermediates

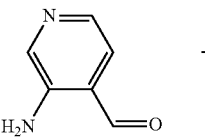

| Int | Structure | Crude yield | LCMS (ES+) | Intermediate Name |
|---|---|---|---|---|
| 48 | 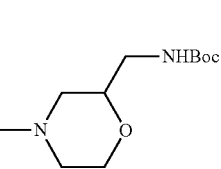 | 55% | 307.2 (M + H)+ | tert-Butyl N-{1-[(3-aminopyridin-4-yl)methyl]piperidin-4-yl}carbamate |
| 49 | 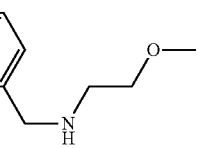 | 100% | 323.1 (M + H)+ | tert-Butyl N-({4-[(3-aminopyridin-4-yl)methyl]morpholin-2-yl}methyl)carbamate |
| 50 | 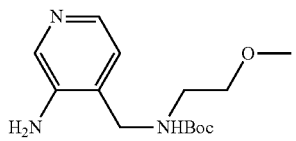 | 79% | 182.1 (M + H)+ | 4-{[(2-Methoxyethyl)amino]methyl}pyridin-3-amine |

Intermediate 51 tert-butyl N-[(3-aminopyridin-4-yl)methyl]-N-(2-methoxyethyl)carbamate

Intermediate 50 (293 mg, 1.62 mmol) was dissolved in DCM (20 mL) and di-tert-butyl dicarbonate (388 mg, 1.78 mmol) was added. The reaction mixture was stirred for 2 h, washed with sat aq Na$_2$CO$_3$ (20 mL), dried (MgSO$_4$) and concentrated in vacuo to give the crude title compound as a yellow gum (366 mg, 81%). LCMS (ES+): 282.1 (M+H)+.

Intermediate 52

3,3-Difluoro-1-{1H-pyrazolo[3,4-c]pyridin-3-yl}pyrrolidine

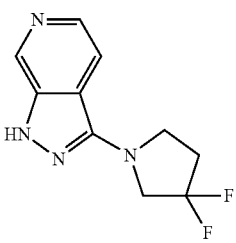 [SMILES: FC1(F)CCN(c2n[nH]c3cnccc23)C1]

Intermediate 27 (246 mg, 1.15 mmol) was dissolved in AcOH (14 mL), and a solution of NaNO$_2$ (79.6 mg, 1.15 mmol) in water (121 µL) was added. The reaction mixture was stirred for 5 min and then concentrated in vacuo. The residue was dissolved in EtOAc (20 mL) and washed with sat aq Na$_2$CO$_3$ (2×10 mL). The organic phase was dried (MgSO$_4$) and concentrated in vacuo to give the crude title compound as a yellow gum (182 mg, 70%). LCMS (ES+): 225.0 (M+H)+.

Intermediates 53-75

Intermediates 53-75 were prepared similarly to Intermediate 52, by reacting Intermediates 29-49 and 51 with NaNO$_2$: see Table 2 below.

TABLE 2

Preparation of 1H-pyrazolo[3,4-c]pyridin-3-yl intermediates

| Int | Structure | SM | Crude yield | LCMS (ES+) | Intermediate Name |
|---|---|---|---|---|---|
| 53 | 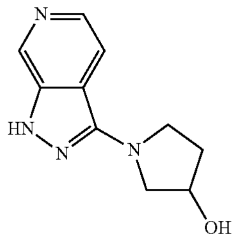 [SMILES: OC1CCN(c2n[nH]c3cnccc23)C1] | 28 | 98% | 205.0 (M + H)+ | 1-{1H-Pyrazolo[3,4-c]pyridin-3-yl}pyrrolidin-3-ol |
| 54 | 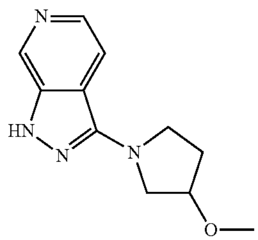 [SMILES: COC1CCN(c2n[nH]c3cnccc23)C1] | 29 | 89% | 219.0 (M + H)+ | 3-Methoxy-1-{1H-pyrazolo[3,4-c]pyridin-3-yl}pyrrolidine |
| 55 | 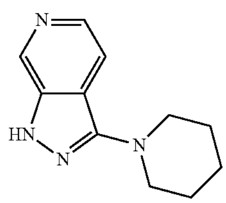 [SMILES: c1cc2c(N3CCCCC3)n[nH]c2cn1] | 30 | 72% | 203.1 (M + H)+ | 1-{1H-Pyrazolo[3,4-c]pyridin-3-yl}piperidine |
| 56 | 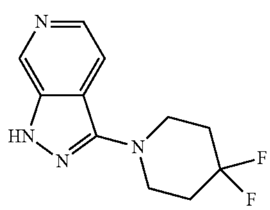 [SMILES: FC1(F)CCN(c2n[nH]c3cnccc23)CC1] | 31 | 70% | 239.0 (M + H)+ | 4,4-Difluoro-1-{1H-pyrazolo[3,4-c]pyridin-3-yl}piperidine |
| 57 | 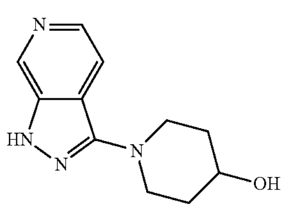 [SMILES: OC1CCN(c2n[nH]c3cnccc23)CC1] | 32 | 60% | 219.1 (M + H)+ | 1-{1H-Pyrazolo[3,4-c]pyridin-3-yl}piperidin-4-ol |
| 58 | 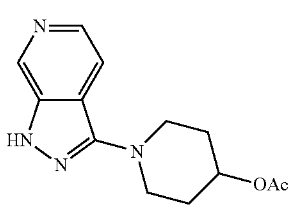 [SMILES: CC(=O)OC1CCN(c2n[nH]c3cnccc23)CC1] | 33 | 69% | 261.1 (M + H)+ | 1-{1H-Pyrazolo[3,4-c]pyridin-3-yl}piperidin-4-yl acetate |

TABLE 2-continued

Preparation of 1H-pyrazolo[3,4-c]pyridin-3-yl intermediates

| Int | Structure | SM | Crude yield | LCMS (ES+) | Intermediate Name |
|---|---|---|---|---|---|
| 59 | 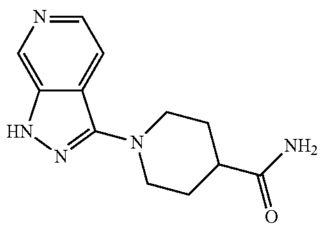 [SMILES: NC(=O)C1CCN(c2n[nH]c3cnccc23)CC1] | 34 | 52% | 246.0 (M + H)+ | 1-{1H-Pyrazolo[3,4-c]pyridin-3-yl}piperidine-4-carboxamide |
| 60 | 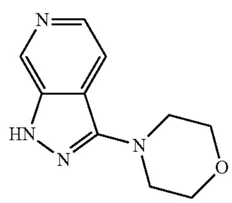 [SMILES: c1cc2c(N3CCOCC3)n[nH]c2cn1] | 35 | 53% | 205.1 (M + H)+ | 4-{1H-Pyrazolo[3,4-c]pyridin-3-yl}morpholine |
| 61 | 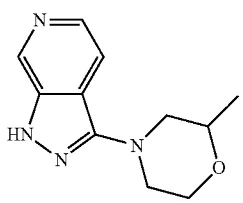 [SMILES: CC1CN(c2n[nH]c3cnccc23)CCO1] | 36 | 75% | 219.1 (M + H)+ | 2-Methyl-4-{1H-pyrazolo[3,4-c]pyridin-3-yl}morpholine |
| 62 | 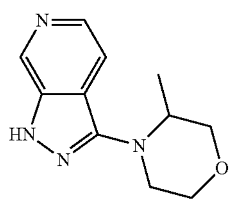 [SMILES: CC1COCCN1c1n[nH]c2cnccc12] | 37 | 66% | 219.1 (M + H)+ | 3-Methyl-4-{1H-pyrazolo[3,4-c]pyridin-3-yl}morpholine |
| 63 | 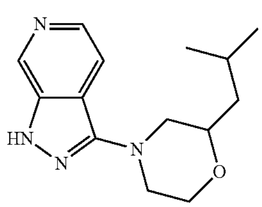 [SMILES: CC(C)CC1CN(c2n[nH]c3cnccc23)CCO1] | 38 | 100% | 261.1 (M + H)+ | 2-(2-Methylpropyl)-4-{1H-pyrazolo[3,4-c]pyridin-3-yl}morpholine |
| 64 | 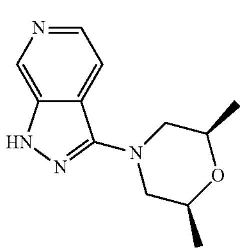 [SMILES: C[C@@H]1CN(c2n[nH]c3cnccc23)C[C@H](C)O1] | 39 | 52% | 233.1 (M + H)+ | (2R,6S)-2,6-Dimethyl-4-{1H-pyrazolo[3,4-c]pyridin-3-yl}morpholine |

TABLE 2-continued

Preparation of 1H-pyrazolo[3,4-c]pyridin-3-yl intermediates

| Int | Structure | SM | Crude yield | LCMS (ES$^+$) | Intermediate Name |
|---|---|---|---|---|---|
| 65 | 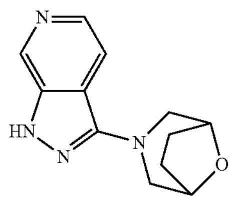 [SMILES: c1cc2c(N3CC4CCC(C3)O4)n[nH]c2cn1] | 40 | 72% | 231.1 (M + H)$^+$ | 3-{1H-Pyrazolo[3,4-c]pyridin-3-yl}-8-oxa-3-azabicyclo[3.2.1]octane |
| 66 | 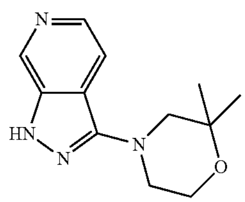 [SMILES: CC1(C)CN(c2n[nH]c3cnccc23)CCO1] | 41 | 91% | 233.1 (M + H)$^+$ | 2,2-Dimethyl-4-{1H-pyrazolo[3,4-c]pyridin-3-yl}morpholine |
| 67 | 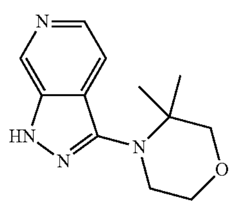 [SMILES: CC1(C)COCCN1c1n[nH]c2cnccc12] | 42 | 73% | 233.1 (M + H)$^+$ | 3,3-Dimethyl-4-{1H-pyrazolo[3,4-c]pyridin-3-yl}morpholine |
| 68 | 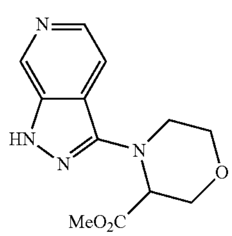 [SMILES: COC(=O)C1COCCN1c1n[nH]c2cnccc12] | 43 | 74% | 263.0 (M + H)$^+$ | Methyl 4-{1H-pyrazolo[3,4-c]pyridin-3-yl}morpholine-3-carboxylate |
| 69 | 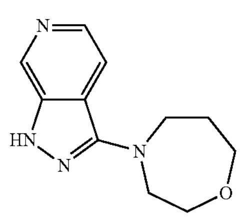 [SMILES: c1cc2c(N3CCCOCC3)n[nH]c2cn1] | 44 | 88% | 219.0 (M + H)$^+$ | 4-{1H-Pyrazolo[3,4-c]pyridin-3-yl}-1,4-oxazepane |
| 70 | 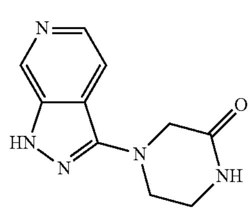 [SMILES: O=C1CN(c2n[nH]c3cnccc23)CCN1] | 45 | 60% | 218.0 (M + H)$^+$ | 4-{1H-Pyrazolo[3,4-c]pyridin-3-yl}piperazin-2-one |

TABLE 2-continued

Preparation of 1H-pyrazolo[3,4-c]pyridin-3-yl intermediates

| Int | Structure | SM | Crude yield | LCMS (ES⁺) | Intermediate Name |
|---|---|---|---|---|---|
| 71 | | 46 | 100% | 207.0 (M + H)⁺ | N-(2-Methoxyethyl)-N-methyl-1H-pyrazolo[3,4-c]pyridin-3-amine |
| 72 | | 47 | 45% | 304.2 (M + H)⁺ | tert-Butyl 4-{1H-pyrazolo[3,4-c]pyridin-3-yl}piperazine-1-carboxylate |
| 73 | | 48 | 66% | 318.1 (M + H)⁺ | tert-Butyl N-(1-{1H-pyrazolo[3,4-c]pyridin-3-yl}piperidin-4-yl)carbamate |
| 74 | | 49 | 71% | 334.0 (M + H)⁺ | tert-Butyl N-[(4-{1H-pyrazolo[3,4-c]pyridin-3-yl}morpholin-2-yl)methyl]carbamate |
| 75 | | 51 | 87% | 293.0 (M + H)⁺ | tert-Butyl N-(2-methoxyethyl)-N-{1H-pyrazolo[3,4-c]pyridin-3-yl}carbamate |

Intermediate 76 tert-Butyl 4-[1-(4-chlorophenyl)-1H-pyrazolo[3,4-c]pyridin-3-yl]piperazine-1-carboxylate

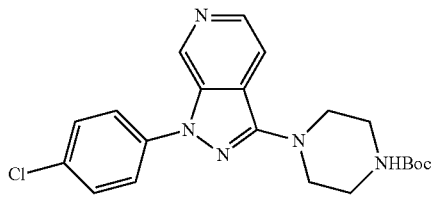

Intermediate 72 (400 mg, 1.32 mmol) was dissolved in DMF (3.6 mL) and 1-chloro-4-iodobenzene (377 mg, 1.58 mmol), N,N'-dimethylethylenediamine (28.4 μL, 0.26 mmol), $K_3PO_4$ (588 mg, 2.77 mmol) and CuI (25.1 mg, 0.13 mmol) were added. The reaction mixture was placed under $N_2$ and heated in a microwave at 140° C. for 20 min. The solvents were removed in vacuo and the residue was purified by column chromatography to give the crude title compound as a light yellow gum (138 mg, 25%). LCMS (ES+): 414.0 $(M+H)^+$.

Intermediate 77 tert-Butyl N-{1-[1-(4-chlorophenyl)-1H-pyrazolo[3,4-c]pyridin-3-yl]piperidin-4-yl}carbamate

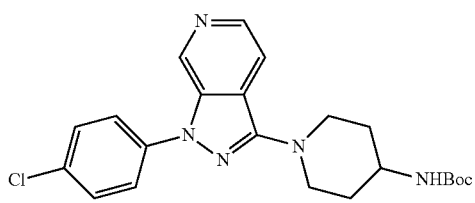 [SMILES: CC(C)(C)OC(=O)NC1CCN(c2nn(-c3ccc(Cl)cc3)c3cnccc23)CC1]

Intermediate 77 was prepared similarly to Intermediate 76 using Intermediate 73 instead of Intermediate 72, to give the crude title compound as a light yellow solid (5.0%). LCMS $(ES^+)$: 428.0 $(M+H)^+$.

Intermediate 78 tert-Butyl N-({4-[1-(4-methylphenyl)-1H-pyrazolo[3,4-c]pyridin-3-yl]morpholin-2-yl}methyl)carbamate

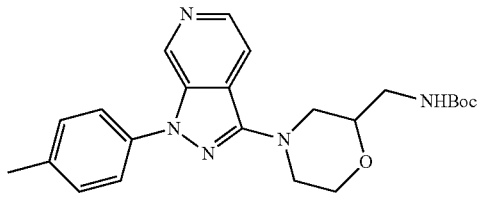 [SMILES: Cc1ccc(-n2nc(N3CCOC(CNC(=O)OC(C)(C)C)C3)c3ccncc32)cc1]

Intermediate 78 was prepared similarly to Intermediate 76, using Intermediate 74 instead of Intermediate 72 and 1-methyl-4-iodo-benzene instead of 1-chloro-4-iodobenzene, to give the crude title compound as a yellow gum (35%). LCMS $(ES^+)$: 424.0 $(M+H)^+$.

Intermediate 79 tert-Butyl N-(2-methoxyethyl)-N-[1-(4-methylphenyl)-1H-pyrazolo[3,4-c]pyridin-3-yl]carbamate

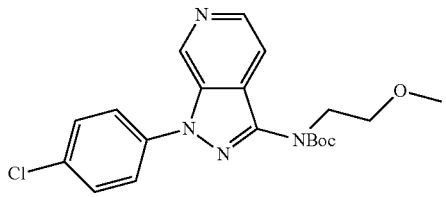 [SMILES: COCCN(C(=O)OC(C)(C)C)c1nn(-c2ccc(Cl)cc2)c2cnccc12]

Intermediate 79 was prepared similarly to Intermediate 76, using Intermediate 75 instead of Intermediate 72, to give the crude title compound as a yellow gum (6.9%). LCMS $(ES^+)$: 383.1 $(M+H)^+$.

Intermediate 80

1-[1-(4-Methylphenyl)-1H-pyrazolo[3,4-c]pyridin-3-yl]piperidin-4-yl acetate

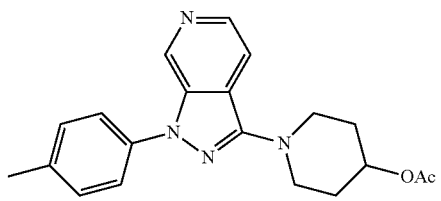 [SMILES: CC(=O)OC1CCN(c2nn(-c3ccc(C)cc3)c3cnccc23)CC1]

Intermediate 80 was prepared similarly to Intermediate 76, using Intermediate 58 instead of Intermediate 72 and 1-methyl-4-iodo-benzene instead of 1-chloro-4-iodobenzene, to give the crude title compound as a yellow gum (30%). LCMS $(ES^+)$: 351.0 $(M+H)^+$.

Intermediate 81

4-[1-(4-Methylphenyl)-1H-pyrazolo[3,4-c]pyridin-3-yl]morpholine-3-carboxylic acid hydrochloride

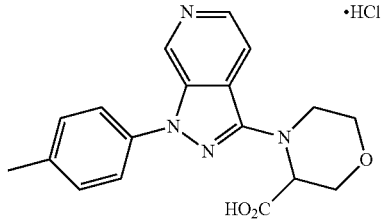 [SMILES: Cc1ccc(-n2nc(N3CCOCC3C(=O)O)c3ccncc32)cc1 ; Cl]

Example 66 (1.00 g, 2.84 mmol) was dissolved in THF/water (16 mL, 1:1), lithium hydroxide monohydrate (262 mg, 6.24 mmol) was added and the reaction mixture was stirred for 3 h. The THF was removed in vacuo and the resulting aqueous solution was acidified to pH 1 with 1 M aq HCl (~5 mL). The precipitate was collected by filtration and washed with water to yield the title compound as an orange solid (28.3 mg, 2.7%). LCMS (ES+): 338.9 (M+H)+. HPLC (method B): Rf 4.40 min, 97% purity.

Intermediate 82

N-methoxy-N-methyloxolane-3-carboxamide

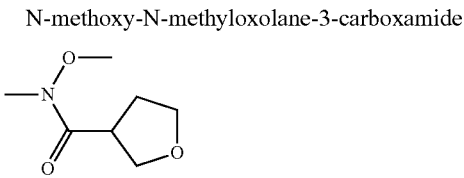

Tetrahydro-3-furoic acid (412 μL, 4.31 mmol) was dissolved in DMF (18 mL) and HBTU (1.96 g, 5.17 mmol) was added. The reaction mixture was stirred for 1 h and N,O-dimethylhydroxylamine hydrochloride (504 mg, 5.17 mmol) and DIPEA (2.25 mL, 12.9 mmol) were added. The reaction mixture was stirred overnight and concentrated in vacuo. The residue was diluted with DCM (40 mL) and washed with sat aq NH₄Cl (20 mL) and sat aq Na₂CO₃ (20 mL), dried (MgSO₄) and concentrated in vacuo. The residue was purified by normal phase column chromatography to give the crude title compound as a yellow gum (1.11 g). LCMS (ES+): 160.1 (M+H)+.

Intermediates 83-85

Intermediates 83-85 were prepared similarly to Intermediate 82, by reacting N,O-dimethylhydroxylamine hydrochloride with the appropriate carboxylic acid; see Table 3 below.

Intermediate 86

(3-Chloropyridin-4-yl)(oxan-4-yl)methanol

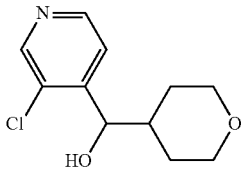

Magnesium (86.5 mg, 3.60 mmol) was stirred vigorously under nitrogen for 30 min. THF (2 mL) and dibromoethane (2 drops) were added and the reaction mixture was warmed to 50° C. A solution of 4-bromotetrahydropyran (495 mg, 3.00 mmol) in THF (4 mL) was added drop-wise over 5 min and the reaction mixture was heated at reflux for 2 h. A solution of 3-chloro-4-pyridaldehyde (170 mg, 1.20 mmol) in THF (4 mL) was added drop-wise over 5 min and the reaction mixture was heated at reflux for 6 h, stirred at room temperature overnight and heated at reflux for 8 h. The reaction mixture was cooled to 0° C. and quenched with sat aq NH₄Cl (10 mL). The reaction mixture was diluted with EtOAc (40 mL) and the aqueous fraction was extracted with EtOAc (3×40 mL). The combined organic fractions were washed with sat aq Na₂CO₃ (20 mL), dried (MgSO₄) and concentrated in vacuo. The residue was purified by normal phase column chromatography to give the crude title compound as a pale yellow gum (69.0 mg, 25%). LCMS (ES+): 228.2 (M+H)+.

TABLE 3

Preparation of Weinreb amide intermediates

| Int | Structure | Crude yield | LCMS (ES+) | Intermediate Name |
|---|---|---|---|---|
| 83 | 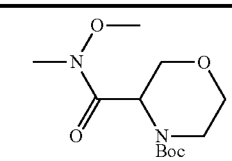 | 100% | 297.0 (M + Na)+ | tert-Butyl 3-[methoxy(methyl)carbamoyl]morpholine-4-carboxylate |
| 84 | 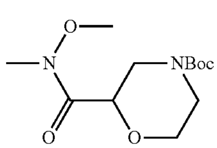 [SMILES: CON(C)C(=O)C1CN(C(=O)OC(C)(C)C)CCO1] | 85% | 297.0 (M + Na)+ | tert-Butyl (2R)-2-[methoxy(methyl)carbamoyl]morpholine-4-carboxylate |
| 85 | 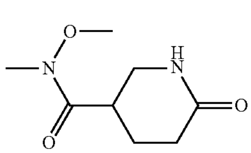 | 48% | 187.0 (M + H)+ | N-Methoxy-N-methyl-6-oxopiperidine-3-carboxamide |

Intermediate 87

3-Chloro-4-[(oxan-4-yl)carbonyl]pyridine

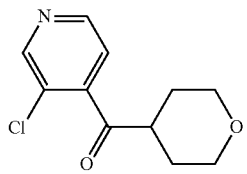

Intermediate 86 (99.0 mg, 0.43 mmol) and IBX (183 mg, 0.65 mmol) were suspended in DCE (2 mL) and the reaction mixture was heated at 70° C. overnight. The reaction mixture was filtered and the solids washed with DCM (50 mL). The filtrate was concentrated in vacuo to give the crude title compound as a yellow gum (109 mg). LCMS is (ES+): 226.2 (M+H)+.

Intermediate 88

3-Fluoro-4-[(oxolan-3-yl)carbonyl]pyridine

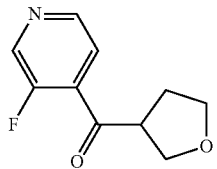

Diisopropylamine (605 µL, 4.30 mmol) was dissolved in THF (8 mL) and cooled to −78° C. nBuLi (1.72 mL, 2.5 M in hexanes, 4.30 mmol) was added and the resulting solution was stirred for 10 min, warmed to room temperature for 30 min and re-cooled to −78° C. 3-Fluoro-pyridine (370 µL, 4.30 mmol) was added drop-wise and the reaction mixture was stirred for 2 h. A solution of N-methoxy-N-methyloxolane-3-carboxamide (685 mg, 4.30 mmol) in THF (4.2 mL) was added drop-wise and the reaction mixture was warmed to room temperature and stirred for 15 min. The reaction mixture was quenched with sat aq $NH_4OAc$ (5 mL), diluted with EtOAc (50 mL), washed with water (2×25 mL), dried ($MgSO_4$) and concentrated in vacuo. The residue was purified by normal phase column chromatography to give the title compound as a yellow gum (61.0 mg, 10%). LCMS (ES+): 196.0 (M+H)+.

Intermediates 89-93

Intermediates 89-93 were prepared similarly to Intermediate 88, by reacting 3-fluoro-pyridines with the appropriate Weinreb amide; see Table 4 below.

TABLE 4

Preparation of 3-fluoro-4-[(pyridin-4-yl)carbonyl]intermediates

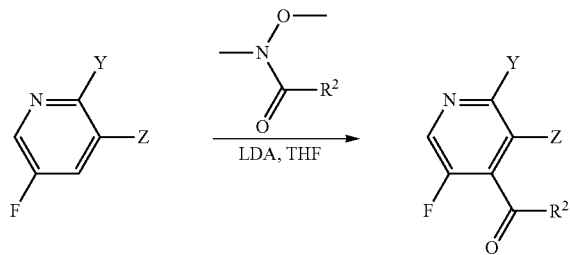

| Int | Structure | SM | Crude yield | LCMS (ES+) | Intermediate Name |
|---|---|---|---|---|---|
| 89 | 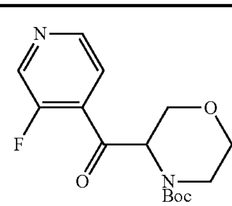 | 83 | 54% | 311.0 (M + H)+ | tert-Butyl 3-[(3-fluoropyridin-4-yl)carbonyl]morpholine-4-carboxylate |
| 90 | 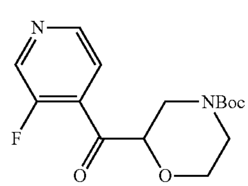 [SMILES: CC(C)(C)OC(=O)N1CCOC(C(=O)c2ccncc2F)C1] | 84 | 50% | 311.0 (M + H)+ | tert-Butyl (2R)-2-[(3-fluoropyridin-4-yl)carbonyl]morpholine-4-carboxylate |

TABLE 4-continued

Preparation of 3-fluoro-4-[(pyridin-4-yl)carbonyl]intermediates

| Int | Structure | SM | Crude yield | LCMS (ES+) | Intermediate Name |
|---|---|---|---|---|---|
| 91 | 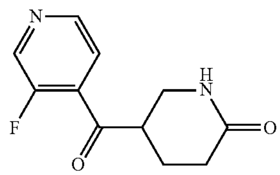 [SMILES: O=C1CCC(C(=O)c2ccncc2F)CN1] | 85 | 5.4% | 223.0 (M + H)+ | 5-[(3-Fluoropyridin-4-yl)carbonyl]piperidin-2-one |
| 92 | 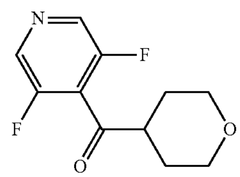 [SMILES: O=C(c1c(F)cncc1F)C1CCOCC1] | 24 | 32% | 228.1 (M + H)+ | 3,5-Difluoro-4-[(oxan-4-yl)carbonyl]pyridine |
| 93 | 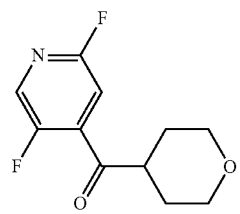 [SMILES: O=C(c1cc(F)ncc1F)C1CCOCC1] | 24 | 67% | 228.1 (M + H)+ | 2,5-Difluoro-4-[(oxan-4-yl)carbonyl]pyridine |

Intermediate 94 tert-Butyl 4-[(3-chloropyridin-4-yl)(hydroxy)methyl]piperidine-1-carboxylate

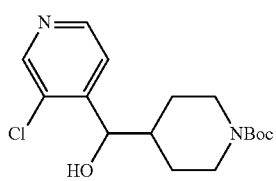

Diisopropylamine (1.82 mL, 12.9 mmol) was dissolved in THF (40 mL) and cooled to −78° C. nBuLi (4.93 mL, 2.5 M in hexanes, 12.3 mmol) was added drop-wise and the solution was warmed to room temperature, stirred for 45 min and re-cooled −78° C. A solution of 3-chloropyridine (1.40 g, 12.3 mmol) in THF (6 mL) was added and the reaction mixture was stirred at −78° C. for 4 h. A solution of tert-butyl 4-formylpiperidine-1-carboxylate (2.89 g, 13.6 mmol) in THF (6 mL) was added and the reaction mixture was warmed to r.t. and stirred for 2 h. The reaction mixture was quenched with water (60 mL) and extracted with DCM (100 mL and 2×30 mL). The combined organic fractions were dried (MgSO4) and concentrated in vacuo. The residue was purified by normal phase column chromatography to give the title compound (2.94 g, 73%) as a yellow gum. LCMS (ES+): 271.0 (M+H-tBu)+.

Intermediate 95 tert-Butyl 4-[(3-chloropyridin-4-yl)carbonyl]piperidine-1-carboxylate

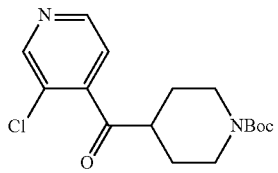 [SMILES: CC(C)(C)OC(=O)N1CCC(C(=O)c2ccncc2Cl)CC1]

Intermediate 95 was prepared similarly to Intermediate 87, using Intermediate 94 instead of Intermediate 86, to give the crude title compound as a yellow liquid (84%). LCMS (ES+): 269.0 (M+H-tBu)+.

Intermediate 96

1-(4-Chlorophenyl)-5-fluoro-3-(oxan-4-yl)-1H-pyrazolo[3,4-c]pyridine

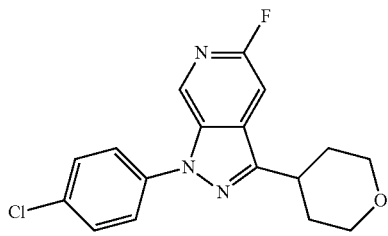 [SMILES: Fc1cc2c(C3CCOCC3)nn(-c3ccc(Cl)cc3)c2cn1]

Intermediate 93 (3.09 g, 13.6 mmol), 4-chlorophenylhydrazine hydrochloride (2.68 g, 15.0 mmol) and DIPEA (4.73 mL, 27.2 mmol) were dissolved in DMA (20 mL) and heated using a microwave at 175° C. for 2 h. The precipitate was collected by filtration, washed with MeOH (2×10 mL) and dried in vacuo to give the title compound as a light yellow solid (974 mg, 22%). LCMS (ES+): 332.0 (M+H)+.

Intermediate 97

3H,4H,5H-Pyrrolo[3,2-d]pyrimidin-4-one

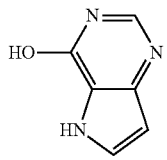

Ethyl 3-amino-1H-pyrrole-2-carboxylate hydrochloride (3.00 g, 15.7 mmol) was dissolved in EtOH (40 mL). Formamidine acetic acid salt (2.44 g, 23.5 mmol) was added and the reaction mixture was heated under reflux at 83° C. for 18 h. The reaction mixture was cooled to r.t. and the precipitate was collected by filtration, washed with EtOH and dried in vacuo to give the title compound as a beige solid (1.70 g, 80%). LCMS (ES+): 135.9 (M+H)+.

Intermediate 98

7-Bromo-3H,4H,5H-pyrrolo[3,2-d]pyrimidin-4-one

Intermediate 97 (1.70 g, 12.6 mmol) and NBS (2.69 g, 15.1 mmol) were dissolved in DMF (100 mL) and stirred for 18 h. The reaction mixture was diluted with water (50 mL) and the resulting solid was collected by filtration, dried, suspended in MeOH and filtered. The filtrate was concentrated in vacuo to give the title compound as a beige solid (2.60 g, 97%). LCMS (ES+): 213.9, 215.9 (M+H)+.

Intermediate 99

7-Bromo-4-chloro-5H-pyrrolo[3,2-d]pyrimidine

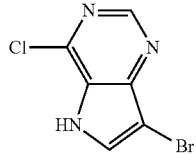 [SMILES: Clc1ncnc2c(Br)c[nH]c12]

Intermediate 98 (1.30 g, 6.07 mmol) was suspended in POCl₃ (60 mL) and heated at 115° C. for 3 h. The reaction mixture was cooled to r.t. and poured cautiously onto ice (300 mL). The reaction mixture was basified with K₂CO₃ and extracted with EtOAc (3×200 mL). The combined organic fractions were dried (MgSO₄) and concentrated in vacuo to give the title compound as a beige solid (490 mg, 35%). LCMS (ES+): 231.9, 233.9, 235.9 (M+H)+.

Intermediate 100

4-Chloro-7-(3,6-dihydro-2H-pyran-4-yl)-5H-pyrrolo[3,2-d]pyrimidine

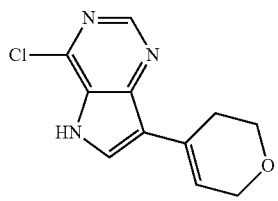 [SMILES: Clc1ncnc2c(C3=CCOCC3)c[nH]c12]

Intermediate 99 (500 mg, 2.15 mmol) was dissolved in THF (30 mL) and cooled to −78° C. tBuLi (3.39 mL, 1.9 M in pentane, 6.45 mmol) was added drop-wise and the reaction mixture was stirred at −78° C. for 5 min. A solution of oxan-4-one (1.08 g, 10.8 mmol) in THF (10 mL) was added and the reaction mixture was stirred at −78° C. for 30 min and then warmed to r.t. The reaction mixture was quenched with water (5 mL) and concentrated in vacuo. The residue was purified by reverse phase column chromatography to give the crude title compound as a yellow solid (507 mg, 100%). LCMS (ES+): 236.0 (M+H)+.

Intermediate 101

7-(Oxan-4-yl)-5H-pyrrolo[3,2-d]pyrimidine

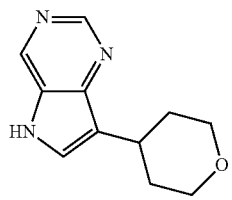 [SMILES: c1ncc2[nH]cc(C3CCOCC3)c2n1]

Intermediate 100 (513 mg, 2.18 mmol) was dissolved in EtOH (4 mL) and cyclohexene (1 mL) and 5 mol % Pd on C (cat) were added. The reaction mixture was heated using a microwave at 150° C. for 30 min, filtered through celite and the solids washed with MeOH (100 mL). The filtrate was concentrated in vacuo and the residue was purified by normal phase column chromatography to give the title compound as a yellow gum (52.0 mg, 12%). LCMS (ES+): 204.0 (M+H)+.

Intermediate 102

(5-Chloropyrimidin-4-yl)(oxan-4-yl)methanone

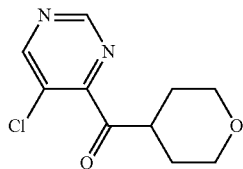

Intermediate 102 was prepared similarly to Intermediate 25, using 5-chloropyrimidine instead of 3-fluoro-pyridine, to give the crude title compound as a yellow liquid (61%). LCMS (ES+): 227.0 (M+H)+.

Intermediate 103

3-(Oxan-4-yl)-1H-pyrrolo[2,3-c]pyridine

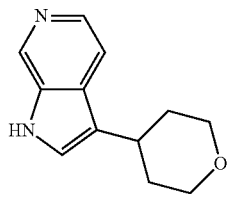

4-Chloro-3-aminopyridine (200 mg, 1.56 mmol) was dissolved in DMA (4 mL) and Pd$_2$(dba)$_3$ (71.2 mg, 0.08 mmol), X-Phos (74.2 mg, 0.16 mmol), potassium acetate (458 mg, 4.67 mmol) and (tetrahydro-pyran-4-yl)-acetaldehyde (598 mg, 4.67 mmol) were added under nitrogen. The reaction mixture was heated at 120° C. overnight, cooled to r.t. and partitioned between water (100 mL) and DCM (100 mL). The aqueous fraction was concentrated in vacuo and the residue was dissolved in DCM (100 mL), dried (MgSO$_4$) and concentrated in vacuo to give the crude title compound as an orange/brown solid (314 mg, 99.8%). LCMS (ES+): 203.1 (M+H)+.

Intermediate 104

1-(4-Chlorophenyl)-3-nitro-1H-pyrrolo[2,3-c]pyridine

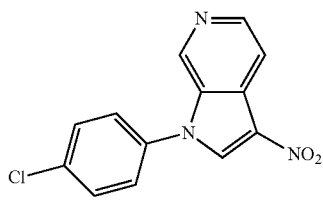 [SMILES: O=[N+]([O-])c1cn(-c2ccc(Cl)cc2)c2cnccc12]

Intermediate 13 (1.54 g, 6.74 mmol) was added portionwise to sulfuric acid (5.85 mL) at 0° C. The reaction mixture was heated to 55° C. and nitric acid (0.42 mL, 69% aq solution, 6.40 mmol) was added cautiously. The reaction mixture was heated at 55° C. for 3 h and then cooled to room temperature, poured into ice-water (100 mL) and neutralised cautiously with 6 M aq NaOH. The resulting precipitate was collected by filtration to give the crude title compound as a brown solid (1.01 g, 55%). LCMS (ES+): 274.0 (M+H)+.

Intermediate 105

1-(4-Chlorophenyl)-1H-pyrrolo[2,3-c]pyridin-3-amine

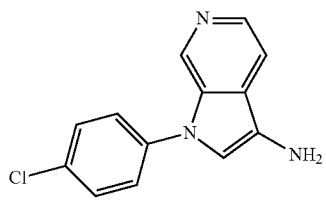

Intermediate 104 (900 mg, 3.29 mmol) was dissolved in EtOAc/EtOH (130 mL, 1:1) and hydrogenated at 70° C. over 10% Ru/C using a Thales H-cube (0.5 mL/min, 70 bar). The solvents were removed in vacuo and the residue was purified by normal phase column chromatography to give the title compound as a brown gum (156 mg, 20%). LCMS (ES+): 244.0 (M+H)+.

Intermediate 106

3-Iodo-2-methyl-1H-pyrrolo[2,3-c]pyridine

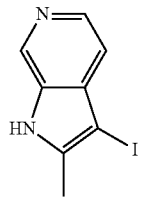

2-Methyl-1H-pyrrolo[2,3-c]pyridine (100 mg, 0.76 mmol) was dissolved in CHCl$_3$ (5 mL), N-iodosuccinimide (179 mg, 0.79 mmol) was added and the reaction mixture was stirred for 2 h. The reaction mixture was quenched with 1 M aq sodium thiosulphate (5 mL) and the CHCl$_3$ was removed in vacuo. The reaction mixture was partitioned between sat aq NaHCO$_3$ (40 mL) and EtOAc (40 mL). The aqueous layer was extracted with EtOAc (40 mL) and the combined organic fractions were washed with sat aq NaHCO$_3$ (50 mL) and brine (50 mL), dried (MgSO$_4$) and concentrated in vacuo to give the title compound as a cream solid (179 mg, 92%). LCMS (ES+): 258.9 (M+H)+.

Intermediate 107 tert-Butyl 3-iodo-2-methyl-1H-pyrrolo[2,3-c]pyridine-1-carboxylate

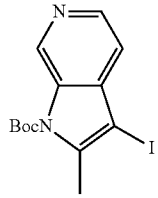

Intermediate 106 (317 mg, 1.23 mmol) was dissolved in DCM (10 mL), 4-dimethylaminopyridine (15.0 mg, 0.12 mmol) and di-tert-butyl dicarbonate (295 mg, 1.35 mmol) were added and the reaction was stirred overnight. The reaction mixture was concentrated in vacuo and the residue was purified by column chromatography to give the title compound as a white solid (369 mg, 84%). LCMS (ES+): 358.9 (M+H)+.

Intermediate 108

3-(3,6-Dihydro-2H-pyran-4-yl)-2-methyl-1H-pyrrolo[2,3-c]pyridine

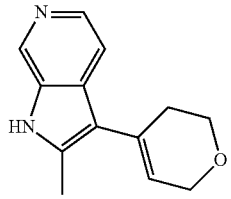

Intermediate 107 (369 mg, 1.03 mmol), 4-(4,4,5,5-tetramethyl-1,3,2-dioxaborolan-2-yl)-3,6-dihydro-2h-pyran (260 mg, 1.24 mmol), tetrakis(triphenylphosphine) palladium(0) (95.2 mg, 0.08 mmol) and Na$_2$CO$_3$ (328 mg, 3.09 mmol) were dissolved in dioxane (2 mL) and water (2 mL) and the reaction mixture was heated in a microwave at 160° C. for 15 min. The reaction mixture was concentrated in vacuo and the residue was purified by column chromatography to give the title compound as a pale yellow solid (161 mg, 73%). LCMS (ES+): 215.1 (M+H)+.

Intermediate 109 tert-Butyl N-(2-{4-[1-(4-chlorophenyl)-1H-pyrrolo[2,3-c]pyridin-3-yl]piperidin-1-yl}-2-oxoethyl)carbamate

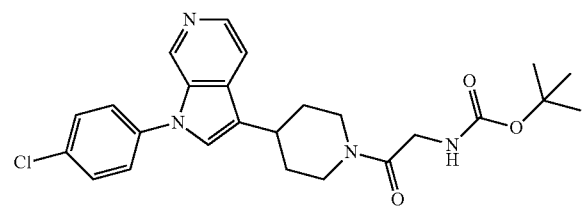 [SMILES: CC(C)(C)OC(=O)NCC(=O)N1CCC(c2cn(-c3ccc(Cl)cc3)c3cnccc23)CC1]

A suspension of Example 10 (30.0 mg, 0.070 mmol), N-(tert-butoxycarbonyl)glycine (15.0 mg, 0.085 mmol), EDC (27.0 mg, 0.14 mmol), HOBT (19.0 mg, 0.14 mmol) and triethylamine (40.0 µL, 0.28 mmol) in THF (2 mL) and MeOH (0.5 mL) was stirred overnight. The mixture was concentrated in vacuo and purified by preparative HPLC to yield the title compound (13.5 mg, 41%). HRMS (ESI+) calcd for C$_{25}$H$_{29}$ClN$_4$O$_3$ 468.1928. found 468.1936. HPLC (method A): Rf 1.89 min, 97% purity.

Intermediate 110 tert-Butyl N-(3-{4-[1-(4-chlorophenyl)-1H-pyrrolo[2,3-c]pyridin-3-yl]piperidin-1-yl}-3-oxopropyl)carbamate

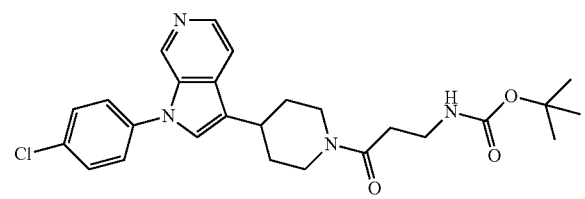 [SMILES: CC(C)(C)OC(=O)NCCC(=O)N1CCC(c2cn(-c3ccc(Cl)cc3)c3cnccc23)CC1]

A suspension of Example 10 (30.0 mg, 0.070 mmol), N-(tert-butoxycarbonyl)-β-alanine (16.0 mg, 0.085 mmol), EDC (27.0 mg, 0.14 mmol), HOBT (19.0 mg, 0.14 mmol) and triethylamine (40.0 µL, 0.28 mmol) in THF (2 mL) and MeOH (0.5 mL) was stirred overnight. The mixture was concentrated in vacuo and purified by preparative HPLC to yield the title compound (11.5 mg, 41%). HRMS (ESI+) calcd for C$_{26}$H$_{31}$ClN$_4$O$_3$ 482.2085. found 482.2097. HPLC (method A): Rf 1.88 min, 99% purity.

Intermediate 111

1-(4-Chlorophenyl)-1H-pyrrolo[2,3-c]pyridine-3-carbaldehyde

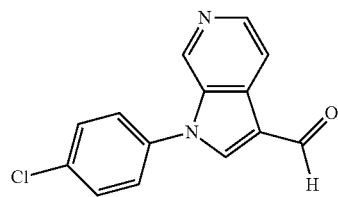 [SMILES: O=Cc1cn(-c2ccc(Cl)cc2)c2cnccc12]

Intermediate 13 (229 mg, 1.00 mmol) was dissolved in dry DMF (770 µL, 10.0 mmol) and cooled in an ice-bath. Phosphoryl chloride (920 µL, 10.0 mmol) was added drop-wise under nitrogen and the reaction mixture was stirred at r.t. for 10 min and then heated at 100° C. for 6 h. After cooling the reaction mixture was added drop-wise to 10% aq Na$_2$CO$_3$ (30 mL). The precipitate formed was collected by filtration, washed with water (3×5 mL) and dried under vacuum to give the crude product (~80% purity) as a brown solid (240 mg). A small sample (12 mg) was purified by preparative HPLC to give the title compound as an off-white solid (3.80 mg, 30%). HRMS (ESI+) calcd for C$_{14}$H$_9$ClN$_2$O, 256.0403. found 256.0413. HPLC (method A): Rf 1.30 min, 100% purity.

Example 1

3-(4-Chlorophenyl)-1-(oxolan-3-ylmethyl)-1H-pyrrolo[3,2-c]pyridine

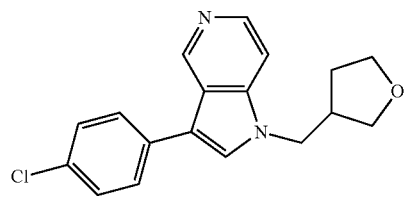 [SMILES: Clc1ccc(-c2cn(CC3CCOC3)c3ccncc23)cc1]

Intermediate 4 (46.0 mg, 0.20 mmol), tetrahydrofuran-3-ylmethyl methanesulfonate (54.0 mg, 0.30 mmol) and Cs$_2$CO$_3$ (98.0 mg, 0.30 mmol) were mixed with DMF (2 mL) and heated at 80° C. overnight. The solvent was evaporated and the residue was purified by flash chromatography (4% MeOH in CH$_3$Cl) to yield the title compound (41.0 mg, 66%).

HRMS (ESI+) calcd for $C_{18}H_{17}ClN_2O$, 312.1029. found 312.1036. HPLC (method A): Rf 1.75 min, 100% purity.

Example 2 tert-Butyl 4-[3-(4-chlorophenyl)-1H-pyrrolo[3,2-c]pyridin-1-yl]piperidine-1-carboxylate

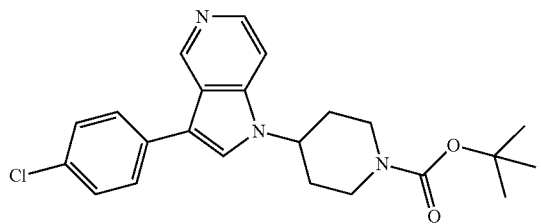 [SMILES: CC(C)(C)OC(=O)N1CCC(n2cc(-c3ccc(Cl)cc3)c3cnccc32)CC1]

Intermediate 4 (46.0 mg, 0.2 mmol), tert-butyl 4-[(methylsulfonyl)oxy]piperidine-1-carboxylate (60.0 mg, 0.30 mmol) and $Cs_2CO_3$ (98.0 mg, 0.30 mmol) were mixed with DMF (2 mL) and heated at 80° C. overnight. The solvent was evaporated and the residue was purified by flash chromatography (3% MeOH in $CH_3Cl$) to yield the title compound (11.0 mg, 13%). HRMS (ESI+) calcd for $C_{23}H_{26}ClN_3O_2$ 411.1714. found 411.1717. HPLC (method A): Rf 2.19 min, 98% purity.

Example 3

3-(4-Chlorophenyl)-1-(oxolan-3-yl)-1H-pyrrolo[3,2-c]pyridine

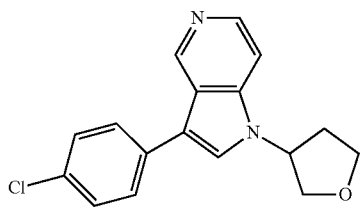 [SMILES: Clc1ccc(-c2cn(C3CCOC3)c3ccncc23)cc1]

Intermediate 4 (66.0 mg, 0.29 mmol), tetrahydrofuran-3-yl methanesulfonate (50.0 mg, 0.30 mmol) and $Cs_2CO_3$ (98.0 mg, 0.30 mmol) were mixed with DMF (2 mL) and heated at 80° C. overnight. The solvent was evaporated and the residue was purified by flash chromatography (3% MeOH in $CH_3Cl$) and then preparative HPLC to give the title compound (14.5 mg, 17%). HRMS (ESI+) calcd for $C_{17}H_{15}ClN_2O$, 298.0873. found 298.0880. HPLC (method A): Rf 1.69 min, 100% purity.

Example 4

3-(4-Chlorophenyl)-1-(oxan-4-yl)-1H-pyrrolo[3,2-c]pyridine

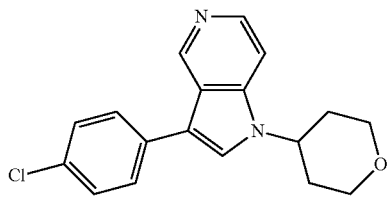 [SMILES: Clc1ccc(-c2cn(C3CCOCC3)c3ccncc23)cc1]

Intermediate 4 (46.0 mg, 0.20 mmol), tetrahydro-2H-pyran-4-yl methanesulfonate (54.0 mg, 0.30 mmol) and $Cs_2CO_3$ (98.0 mg, 0.30 mmol) were mixed with DMF (2 mL) and heated at 80° C. overnight. The solvent was evaporated and the residue was purified by flash chromatography (4% MeOH in $CH_3Cl$) and then preparative HPLC to give the title compound (8.70 mg, 14%). HRMS (ESI+) calcd for $C_{18}H_{17}ClN_2O$, 312.1029. found 312.1036. HPLC (method A): Rf 1.71 min, 100% purity.

Example 5

Bis(2,2,2-trifluoroacetic acid); 4-[3-(4-chlorophenyl)-1H-pyrrolo[3,2-c]pyridin-1-yl]piperidine

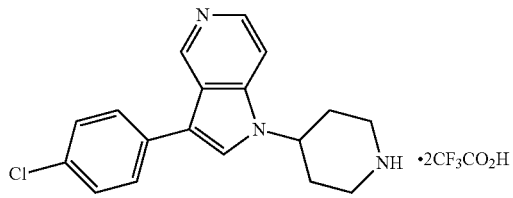 [SMILES: Clc1ccc(-c2cn(C3CCNCC3)c3ccncc23)cc1]

tert-Butyl 4-[3-(4-chlorophenyl)-1H-pyrrolo[3,2-c]pyridin-1-yl]piperidine-1-carboxylate (Example 2; 5 mg, 0.012 mmol) was mixed with DCM (0.15 mL) and TFA (0.05 mL) and kept at room temperature overnight. The solution was concentrated to yield the title compound (7 mg, 100%). HRMS (ESI+) calcd for $C_{18}H_{18}ClN_3$ 311.1189. found 311.1192. HPLC (method A): Rf 1.31 min, 100% purity.

Example 6

4-[3-(3,4-Dichlorophenyl)-1H-pyrrolo[3,2-c]pyridin-1-yl]piperidine hydrochloride

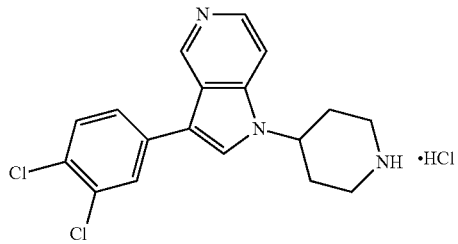 [SMILES: Clc1ccc(-c2cn(C3CCNCC3)c3ccncc23)cc1Cl ; Cl]

Intermediate 6 (11.0 mg, 0.025 mmol) was treated with conc. HCl (0.5 mL) in MeOH (2 mL) at 50° C. for 30 min. The solvents were evaporated and the residue was dried under vacuum overnight to give the title compound as a white solid (8 mg, 93%). HRMS (ESI+) calcd for $C_{18}H_{17}Cl_2N_3$ 345.0800. found 345.0802. HPLC (method A): Rf 1.42 min, 100% purity.

Example 7

1-{4-[3-(3,4-Dichlorophenyl)-1H-pyrrolo[3,2-c]pyridin-1-yl]piperidin-1-yl}-2-hydroxyethan-1-one

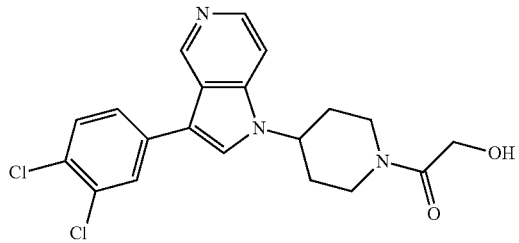 [SMILES: O=C(CO)N1CCC(n2cc(-c3ccc(Cl)c(Cl)c3)c3cnccc32)CC1]

To a mixture of Example 6 (5.00 mg, 0.013 mmol) and hydroxyacetic acid (2.00 mg, 0.03 mmol) in THF (1 mL) and MeOH (0.5 mL) was added HOBT (4.00 mg, 0.03 mmol), EDC (5.00 mg, 0.03 mmol) and triethylamine (7.00 μL, 0.05 mmol). The mixture was stirred overnight and then diluted with MeOH. Purification by preparative HPLC gave the title compound as a white solid (4 mg, 76%). HRMS (ESI+) calcd for $C_{20}H_{19}Cl_2N_3O_2$ 403.0854. found 403.0857. HPLC (method A): Rf 1.66 min, 99% purity.

Example 8

4-[1-(4-Chlorophenyl)-1H-pyrrolo[2,3-c]pyridin-3-yl]-hydrochloride

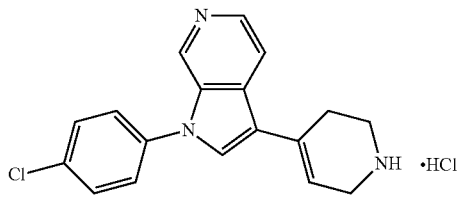 [SMILES: Clc1ccc(-n2cc(C3=CCNCC3)c3ccncc32)cc1 ; Cl]

A suspension of Intermediate 8 (3.50 mg, 0.0085 mmol) in 1.25 M HCl in MeOH (1 mL) was stirred overnight. The mixture was concentrated, dissolved in MeOH, concentrated again and then dried under vacuum to yield the title compound as a white solid (2.70 mg, 92%). HRMS (ESI+) calcd for $C_{18}H_{16}ClN_3$ 309.1033. found 309.1035. HPLC (method A): Rf 1.19 min, 94% purity.

Example 9 tert-Butyl 4-[1-(4-chlorophenyl)-1H-pyrrolo[2,3-c]pyridin-3-yl]piperidine-1-carboxylate

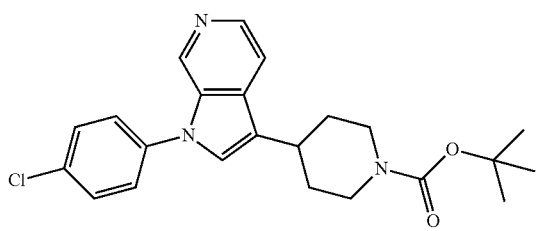 [SMILES: CC(C)(C)OC(=O)N1CCC(c2cn(-c3ccc(Cl)cc3)c3cnccc23)CC1]

A suspension of Intermediate 9 (497 mg, 1.65 mmol), 1-chloro-4-iodobenzene (472 mg, 1.98 mmol), copper(I) iodide (94.0 mg, 0.50 mmol), N,N'-dimethylethylenediamine (44.0 mg, 0.50 mmol) and $K_3PO_4$ (595 mg, 2.80 mmol) in toluene (15 mL) was heated at 110° C. for 72 h. The mixture was cooled to r.t. and diluted with MeOH (15 mL), filtered and concentrated. The residue was purified by flash chromatography (EtOAc) to yield the title compound as a yellow solid (606 mg, 89%). HRMS (ESI+) calcd for $C_{23}H_{26}ClN_3O_2$ 411.1714. found 411.1725. HPLC (method A): Rf 2.14 min, 97% purity.

Example 10

1-(4-Chlorophenyl)-3-piperidin-4-yl-1H-pyrrolo[2,3-c]pyridine trifluoroacetate

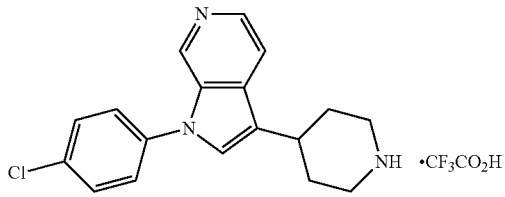 [SMILES: Clc1ccc(-n2cc(C3CCNCC3)c3ccncc32)cc1 ; "·CF3CO2H"]

A suspension of Example 9 (580 mg, 1.41 mmol) in DCM (10 mL) and TFA (6 mL) was stirred for 2 h, concentrated, dissolved in MeOH and concentrated in vacuo to yield the title compound (569 mg, 95%). HRMS (ESI+) calcd for $C_{18}H_{18}ClN_3$ 311.1189. found 311.1192. HPLC (method A): Rf 1.13 min, 97% purity.

Example 11 tert-Butyl N-{4-[1-(4-chlorophenyl)-1H-pyrrolo[2,3-c]pyridin-3-yl]cyclohexyl}-carbamate

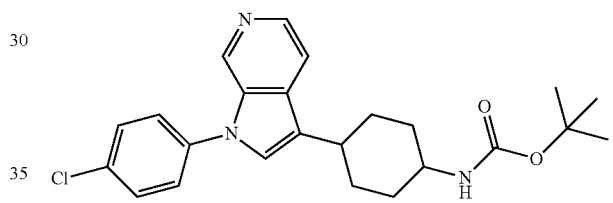

A suspension of Intermediate 11 (32.0 mg, 0.10 mmol), (4-chlorophenyl)boronic acid (16.0 mg, 0.10 mmol), copper (II) acetate (18.0 mg, 0.10 mmol) and triethylamine (20.0 mg, 0.20 mmol) in DCM (1 mL) was stirred for 72 h. The mixture was concentrated and purified by preparative HPLC to yield the title compound (6 mg, 14%). HRMS (ESI+) calcd for $C_{24}H_{28}ClN_3O_2$ 425.1870. found 425.1878. HPLC (method A): Rf 2.19 min, 99% purity.

Example 12

4-[1-(4-Chlorophenyl)-1H-pyrrolo[2,3-c]pyridin-3-yl]cyclohexan-1-amine hydrochloride

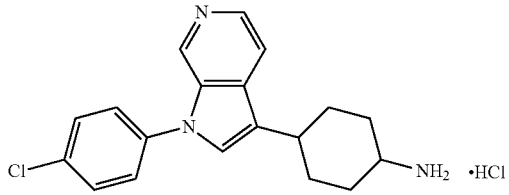 [SMILES: NC1CCC(c2cn(-c3ccc(Cl)cc3)c3cnccc23)CC1 ; Cl]

A suspension of Example 11 (3.50 mg, 0.0082 mmol) in 1.25 M HCl in MeOH (1 mL) was stirred overnight. The mixture was concentrated, dissolved in MeOH and concentrated in vacuo to yield a diastereoisomeric mixture of the title compound (2.80 mg, 94%). HRMS (ESI+) calcd for $C_{19}H_{20}ClN_3$ 325.1346. found 325.1350. HPLC (method A): Rf 1.20, 1.25 min, 99% purity.

Example 13

4-[1-(4-Chloro-2-methylphenyl)-1H-pyrrolo[2,3-c] pyridin-3-yl]cyclohexan-1-amine hydrochloride

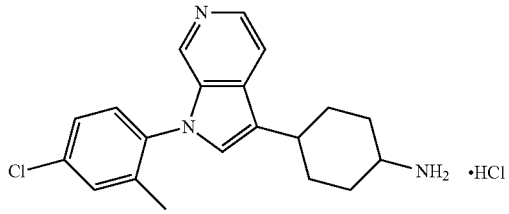 [SMILES: Cc1cc(Cl)ccc1-n1cc(C2CCC(N)CC2)c2ccncc21 ; Cl]

A suspension of Intermediate 12 (1.20 mg, 0.0027 mmol) in 1.25 M HCl in MeOH (1 mL) was stirred overnight. The mixture was concentrated, dissolved in MeOH and concentrated in vacuo to yield a diastereoisomeric mixture of the title compound (1 mg, 98%). HRMS (ESI+) calcd for $C_{20}H_{22}ClN_3$ 339.1502. found 339.1505. HPLC (method A): Rf 1.33, 1.39 min, 94% purity.

Example 14

1-{4-[1-(4-Chlorophenyl)-1H-pyrrolo[2,3-c]pyridin-3-yl]piperidin-1-yl}-2-(dimethyl-amino)ethan-1-one

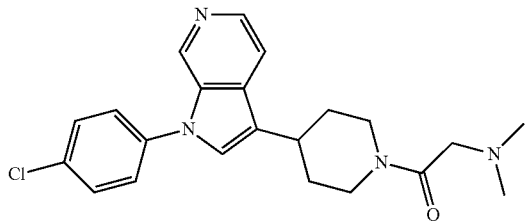 [SMILES: CN(C)CC(=O)N1CCC(c2cn(-c3ccc(Cl)cc3)c3cnccc23)CC1]

A suspension of Example 10 (30.0 mg, 0.070 mmol), N,N-dimethylglycine (9.00 mg, 0.085 mmol), EDC (27.0 mg, 0.14 mmol), HOBT (19.0 mg, 0.14 mmol) and triethylamine (40.0 µL, 0.28 mmol) in THF (2 mL) and MeOH (0.5 mL) was stirred overnight. The mixture was concentrated and then purified by preparative HPLC to yield the title compound (13.0 mg, 47%). HRMS (ESI+) calcd for $C_{22}H_{25}ClN_4O$, 396.1717. found 396.1727. HPLC (method A): Rf 1.23 min, 99% purity.

Example 15

1-{4-[1-(4-Chlorophenyl)-1H-pyrrolo[2,3-c]pyridine-3-yl]piperidin-1-yl}-2-hydroxyethan-1-one

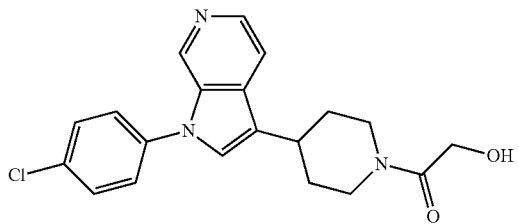 [SMILES: O=C(CO)N1CCC(c2cn(-c3ccc(Cl)cc3)c3cnccc23)CC1]

A suspension of Example 10 (30.0 mg, 0.070 mmol), hydroxyacetic acid (6.00 mg, 0.085 mmol), EDC (27.0 mg, 0.14 mmol), HOBT (19.0 mg, 0.14 mmol) and triethylamine (40.0 µL, 0.28 mmol) in THF (2 mL) and MeOH (0.5 mL) was stirred overnight. The mixture was concentrated in vacuo and purified by preparative HPLC to yield the title compound (11.9 mg, 46%). HRMS (ESI+) calcd for $C_{20}H_{20}ClN_3O_2$ 369.1244. found 369.1252. HPLC (method A): Rf 1.52 min, 98% purity.

Example 16

2-Amino-{4-[1-(4-chlorophenyl)-1H-pyrrolo[2,3-c] pyridin-3-yl]piperidin-1-yl}-ethan-1-one hydrochloride

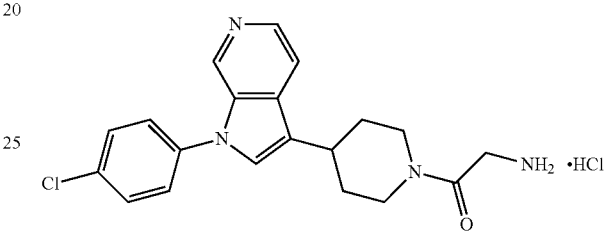

A suspension of Intermediate 109 (9.50 mg, 0.020 mmol) in 1.25 M HCl in MeOH (1.5 mL) was stirred overnight. The mixture was concentrated in vacuo, dissolved in MeOH, and concentrated in vacuo to yield the title compound as a white solid (8 mg, 97%). HRMS (ESI+) calcd for $C_{20}H_{21}ClN_4O$, 368.1404. found 368.1401. HPLC (method A): Rf 1.24 min, 99% purity.

Example 17

3-Amino-1-{4-[1-(4-chlorophenyl)-1H-pyrrolo[2,3-c]pyridin-3-yl]piperidin-1-yl}propan-1-one hydrochloride

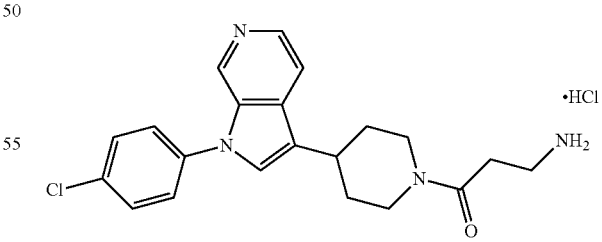

A suspension of Intermediate 110 (7.50 mg, 0.018 mmol) in 1.25 M HCl in MeOH (1.5 mL) was stirred overnight. The mixture was concentrated in vacuo, dissolved in MeOH and concentrated in vacuo to yield the title compound as a white solid (7.10 mg, 95%). HRMS (ESI+) calcd for $C_{21}H_{23}ClN_4O$, 382.1560. found 382.1564. HPLC (method A): Rf 1.27 min, 98% purity.

Example 18

2-{4-[1-(4-Chlorophenyl)-1H-pyrrolo[2,3-c]pyridin-3-yl]piperidin-1-yl}ethan-1-ol

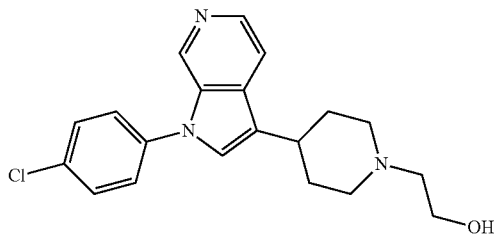 [SMILES: OCCN1CCC(c2cn(-c3ccc(Cl)cc3)c3cnccc23)CC1]

A suspension of Example 10 (25.0 mg, 0.059 mmol), hydroxyacetaldehyde (11.0 mg, 0.18 mmol) and NaBH(OAc)$_3$ (37.0 mg, 0.18 mmol) in MeOH (1.5 mL) was stirred overnight and purified by preparative HPLC to yield the title compound (14.8 mg, 71%). HRMS (ESI+) calcd for $C_{20}H_{22}ClN_3O$, 355.1451. found 355.1456. HPLC (method A): Rf 1.17 min, 99% purity.

Example 19

4-[1-(4-Chlorophenyl)-1H-pyrrolo[2,3-c]pyridin-3-yl]-1-(1H-pyrazol-3-ylmethyl)-piperidine

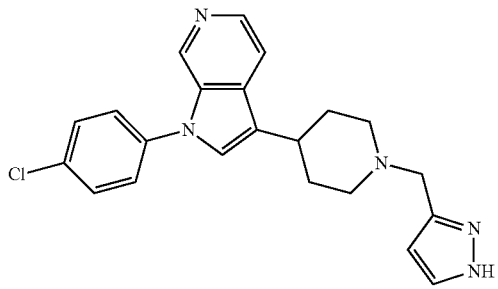 [SMILES: Clc1ccc(-n2cc(C3CCN(Cc4cc[nH]n4)CC3)c3ccncc32)cc1]

A suspension of Example 10 (25.0 mg, 0.059 mmol), 1H-pyrazole-3-carbaldehyde (17.0 mg, 0.18 mmol) and NaBH(OAc)$_3$ (37.0 mg, 0.18 mmol) in MeOH (1.5 mL) was stirred overnight and purified by preparative HPLC to yield the title compound (6.80 mg, 30%). HRMS (ESI+) calcd for $C_{22}H_{22}ClN_5$ 391.1564. found 391.1568. HPLC (method A): Rf 1.24 min, 100% purity.

Example 20

4-[1-(4-Chlorophenyl)-1H-pyrrolo[2,3-c]pyridin-3-yl]-1-[(1-methyl-1H-pyrazol-4-yl)-methyl]piperidine

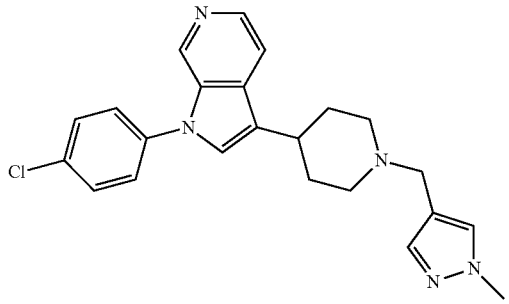 [SMILES: Cn1cc(CN2CCC(c3cn(-c4ccc(Cl)cc4)c4cnccc34)CC2)cn1]

A suspension of Example 10 (25.0 mg, 0.059 mmol), 1-methyl-1H-pyrazole-4-carbaldehyde (19.0 mg, 0.18 mmol) and NaBH(OAc)$_3$ (37.0 mg, 0.18 mmol) in MeOH (1.5 mL) was stirred overnight and purified by preparative HPLC to yield the title compound (4.90 mg, 21%). HRMS (ESI+) calcd for $C_{23}H_{24}ClN_5$ 405.1720. found 405.1735. HPLC (method A): Rf 1.26 min, 100% purity.

Example 21

3-{4-[1-(4-Chlorophenyl)-1H-pyrrolo[2,3-c]pyridine-3-yl]piperidin-1-yl}propanenitrile hydrochloride

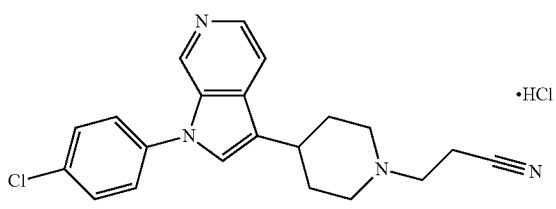 [SMILES: N#CCCN1CCC(c2cn(-c3ccc(Cl)cc3)c3cnccc23)CC1 ; Cl]

A suspension of Example 10 (25.0 mg, 0.059 mmol), 3-bromopropionitrile (16.0 mg, 0.12 mmol) and K$_2$CO$_3$ (excess) in dry DMF (2 mL) was stirred overnight. Further 3-bromopropionitrile (1 drop) was added and the reaction mixture was stirred for 24 h and then purified by preparative HPLC. 1.25 M HCl in MeOH (1.5 mL) was added and the mixture was concentrated in vacuo to give the title compound (9.80 mg, 42%). HRMS (ESI+) calcd for $C_{21}H_{21}ClN_4$ 364.1455. found 364.1459. HPLC (method A): Rf 1.28 min, 99% purity.

Example 22

4-{4-[1-(4-Chlorophenyl)-1H-pyrrolo[2,3-c]pyridin-3-yl]piperidin-1-yl}butanenitrile hydrochloride

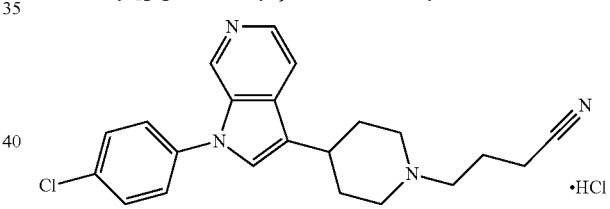

A suspension of Example 10 (25.0 mg, 0.059 mmol), 4-bromobutyronitrile (17.0 mg, 0.12 mmol) and K$_2$CO$_3$ (excess) (excess) in dry DMF (2 mL) was stirred overnight. The reaction mixture was concentrated in vacuo and purified by preparative HPLC. 1.25 M HCl in MeOH (1.5 mL) was added and the mixture was concentrated in vacuo to give the title compound (9 mg, 37%). HRMS (ESI+) calcd for $C_{22}H_{23}ClN_4$ 378.1611. found 378.1616. HPLC (method A): Rf 1.32 min, 99% purity.

Example 23

[1-(4-Chlorophenyl)-1H-pyrrolo[2,3-c]pyridin-3-yl]methanol

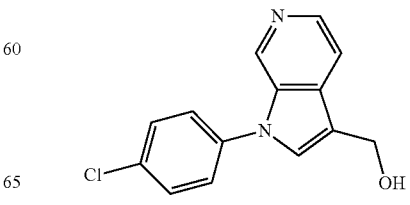

Sodium acetate (326 mg, 4.00 mmol), 12.3 M formaldehyde in water (780 μL, 10.0 mmol) and AcOH (2 mL) were added to Intermediate 13 (180 mg, 0.80 mmol). The mixture was heated at reflux for 30 h. After cooling the mixture was added to 2 M NaOH (30 mL). The precipitate formed was collected by filtration, washed with water (4×5 mL) and dried under vacuum. The residue was purified by preparative to give the title compound as a yellow solid (60.0 mg, 29%). HRMS (ESI+) calcd for $C_{14}H_{11}ClN_2O$, 258.0560. found 258.0570. HPLC (method A): Rf 1.29 min, 100% purity.

Example 24

1-{[1-(4-Chlorophenyl)-1H-pyrrolo[2,3-c]pyridin-3-yl]methyl}-4-methylpiperazine

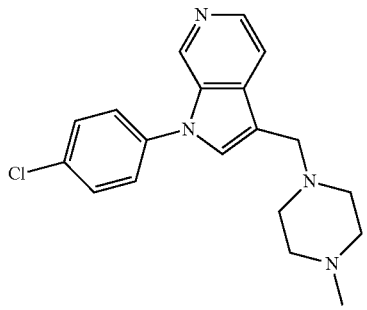 [SMILES: CN1CCN(Cc2cn(-c3ccc(Cl)cc3)c3cnccc23)CC1]

A mixture of Intermediate 111 (12.8 mg, 0.05 mmol) and 1-methylpiperazine (20.0 mg, 0.20 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (9.50 μL, 0.20 mmol). The reaction mixture was shaken for 1 h and was then diluted with MeOH (1.5 mL) and water (0.5 mL). The solution was purified by preparative HPLC to give the title compound as an off-white solid (6 mg, 35%). HRMS (ESI+) calcd for $C_{19}H_{21}ClN_4$ 340.1455. found 340.1465. HPLC (method A): Rf 1.07 min, 94% purity.

Example 25 tert-Butyl 4-{[1-(4-chlorophenyl)-1H-pyrrolo[2,3-c]pyridin-3-yl]

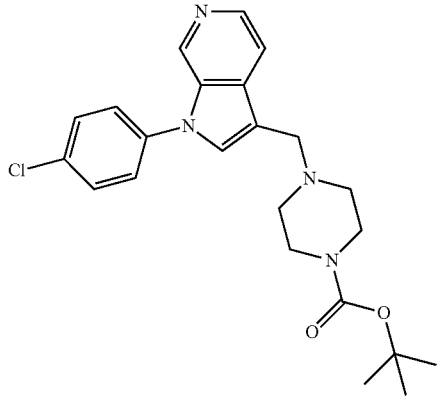 [SMILES: CC(C)(C)OC(=O)N1CCN(Cc2cn(-c3ccc(Cl)cc3)c3cnccc23)CC1]

A mixture of Intermediate 111 (15.0 mg, 0.06 mmol) and tert-butyl piperazine-1-carboxylate (45.0 mg, 0.24 mmol) in 1,2-dichloroethane (200 μL) and DMF (100 μL) was shaken for 1 h. A solution of NaBH(OAc)$_3$ (25.0 mg, 0.120 mmol) in DMF (100 μL) was added followed by AcOH (11.0 μL, 0.24 mmol). The reaction mixture was shaken for 1 h and then diluted with MeOH (1.5 mL) and water (0.5 mL). The solution was purified by preparative HPLC to give the title compound as an off-white solid (9.60 mg, 38%). HRMS (ESI+) calcd for $C_{23}H_{27}ClN_4O_2$ 426.1823. found 426.1838. HPLC (method A): Rf 1.51 min, 98% purity.

Example 26

1-{[1-(4-Chlorophenyl)-1H-pyrrolo[2,3-c]pyridin-3-yl]methyl}piperazine

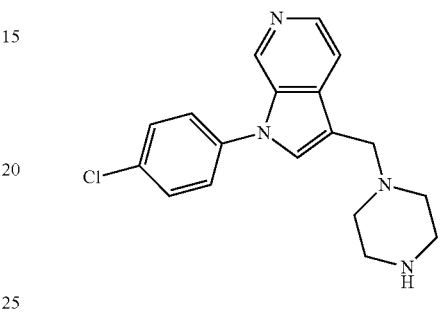

Example 25 (7.80 mg, 0.024 mmol) was dissolved in MeOH (500 μL) and 2 M HCl in diethyl ether (1 mL) was added. The mixture was kept at room temperature for 1.5 h. The reaction mixture was concentrated in vacuo and the residue was dissolved in MeOH (1 mL) and 2 M ammonia in MeOH (1 mL) was added. The solution was purified by preparative HPLC to give the title compound as a white solid (4.30 mg, 55%). HRMS (ESI+) calcd for $C_{18}H_{19}ClN_4$ 326.1298. found 326.1303. HPLC (method A): Rf 1.02 min, 81% purity.

Example 27

2-(1-{[1-(4-Chlorophenyl)-1H-pyrrolo[2,3-c]pyridin-3-yl]methyl}piperidin-4-yl)ethan-1-ol

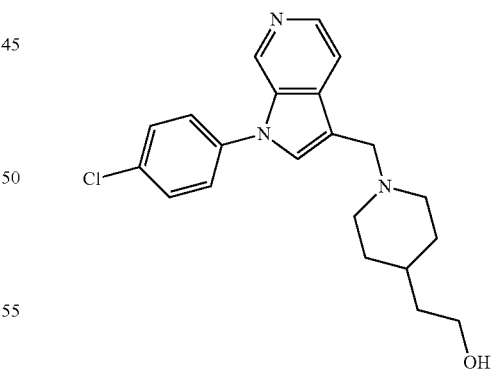

A mixture of Intermediate 111 (15.0 mg, 0.06 mmol) and 4-piperidine ethanol (31.0 mg, 0.24 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (11.0 μL, 0.24 mmol). The reaction mixture was shaken at overnight and then diluted with MeOH (1.5 mL) and water (0.5 mL). The solution was purified by preparative HPLC to give the title compound as a light yellow solid (9.80 mg, 44%). HRMS (ESI+) calcd for $C_{21}H_{24}ClN_3O$, 369.1608. found 369.1619. HPLC (method A): Rf 1.11 min, 91% purity.

Example 28

(1-{[1-(4-Chlorophenyl)-1H-pyrrolo[2,3-c]pyridin-3-yl]methyl}piperidin-4-yl)methanol

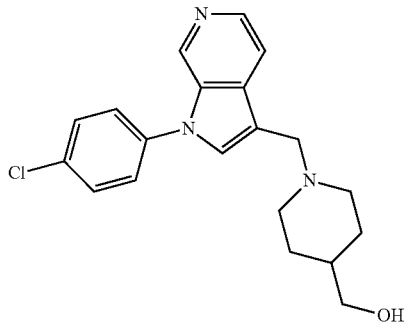 [SMILES: OCC1CCN(Cc2cn(-c3ccc(Cl)cc3)c3cnccc23)CC1]

A mixture of Intermediate 111 (15.0 mg, 0.06 mmol) and 4-piperidinemethanol (28.0 mg, 0.24 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (11.0 μL, 0.24 mmol). The reaction mixture was shaken at overnight and then diluted with MeOH (1.5 mL) and water (0.5 mL). The solution was purified by preparative HPLC to give the title compound as an off-white solid (8.10 mg, 38%). HRMS (ESI+) calcd for $C_{20}H_{22}ClN_3O$, 355.1451. found 355.1460. HPLC (method A): Rf 1.06 min, 98% purity.

Example 29

4-{[1-(4-Chlorophenyl)-1H-pyrrolo[2,3-c]pyridin-3-yl]methyl}morpholine

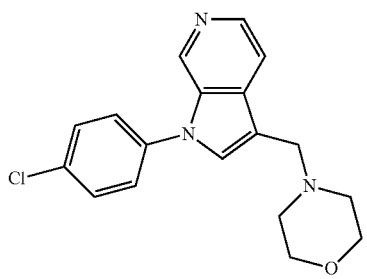 [SMILES: Clc1ccc(-n2cc(CN3CCOCC3)c3ccncc32)cc1]

A mixture of Intermediate 111 (15.0 mg, 0.06 mmol) and morpholine (21.0 mg, 0.24 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (11.0 μL, 0.24 mmol). The reaction mixture was shaken overnight and then diluted with MeOH (1.5 mL) and water (0.5 mL). The solution was purified by preparative HPLC to give the title compound as a light yellow solid (7.60 mg, 39%). HRMS (ESI+) calcd for $C_{18}H_{18}ClN_3O$, 327.1138. found 327.1153. HPLC (method A): Rf 1.06 min, 97% purity.

Example 30

1-{[1-(4-Chlorophenyl)-1H-pyrrolo[2,3-c]pyridin-3-yl]methyl}piperidin-4-ol

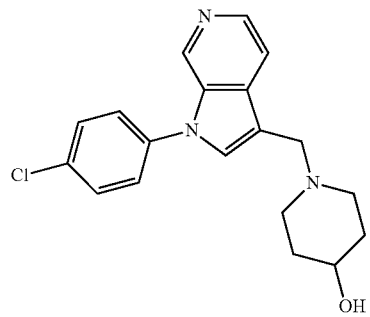 [SMILES: OC1CCN(Cc2cn(-c3ccc(Cl)cc3)c3cnccc23)CC1]

A mixture of Intermediate 111 (15.0 mg, 0.06 mmol) and 4-hydroxypiperidine (24.0 mg, 0.24 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (11.0 μL, 0.24 mmol). The reaction mixture was shaken overnight and then diluted with MeOH (1.5 mL) and water (0.5 mL). The solution was purified by preparative HPLC (Xterra C18, 50 mM NH$_4$HCO$_3$ (pH 10)-CH$_3$CN) and then re-purified (ACE C8, 0.1% TFA-CH$_3$CN). The combined acidic fractions were basified with 2 M NaOH (1.5 mL) and extracted with DCM (6 mL). The organic phase was collected, dried (MgSO$_4$) and concentrated in vacuo to give the title compound as a white solid (3.70 mg, 18%). HRMS (ESI+) calcd for $C_{19}H_{20}ClN_3O$, 341.1295. found 341.1304. HPLC (method A): Rf 1.00 min, 100% purity.

Example 31

2-({[1-(4-Chlorophenyl)-1H-pyrrolo[2,3-c]pyridin-3-yl]methyl}amino)ethan-1-ol

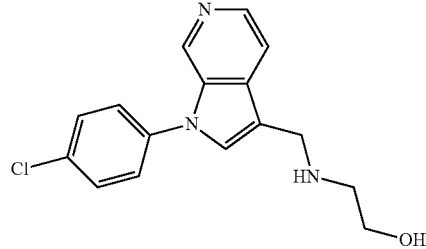 [SMILES: OCCNCc1cn(-c2ccc(Cl)cc2)c2cnccc12]

A mixture of Intermediate 111 (15.0 mg, 0.06 mmol) and ethanolamine (15.0 mg, 0.24 mmol) in 1,2-dichloroethane (200 μL) and DMF (100 μL) was shaken for 1 h. A solution of NaBH(OAc)$_3$ (25.0 mg, 0.12 mmol) in DMF (100 μL) was added followed by AcOH (11.0 μL, 0.24 mmol). The reaction mixture was shaken overnight and then diluted with MeOH (1.5 mL) and water (0.5 mL). The solution was purified by preparative HPLC to give the title compound as a light yellow solid (6.50 mg, 36%). HRMS (ESI+) calcd for $C_{16}H_{16}ClN_3O$, 301.0982. found 301.0984. HPLC (method A): Rf 1.01 min, 100% purity.

Example 32

4-[3-(4-Methylphenyl)imidazo[1,5-a]pyrazin-1-yl]morpholine

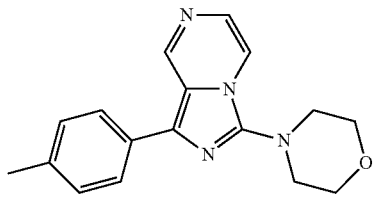 [SMILES: Cc1ccc(-c2nc(N3CCOCC3)n3ccncc23)cc1]

Intermediate 16 (690 mg, 2.21 mmol) was dissolved in $POCl_3$ (5 mL) and heated to 100° C. for 2 h. The reaction mixture was poured into ice/water (100 mL) and cautiously basified to pH ~9 with solid $Na_2CO_3$. The resulting solution was extracted with DCM (3×100 mL) and the combined organic fractions were dried ($MgSO_4$) and concentrated in vacuo. The crude product was purified by flash chromatography (1-2% MeOH in DCM) and recrystallised from EtOAc/heptane to give the title compound as an orange solid (162 mg). MS (ESI+) m/z=295.5 (M+H)+. HPLC (method B): Rf 4.62 min, 99.5% purity.

Examples 33-39

Examples 33-39 were prepared similarly to Example 32, by reacting Intermediates 17-23 with $POCl_3$; see Table 5 below.

TABLE 5

POCl3 cyclisations

| Ex | Structure | Name | Int | Yield | LCMS, HPLC |
|---|---|---|---|---|---|
| 33 | 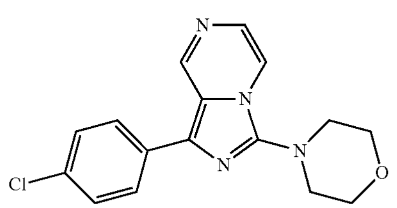 [SMILES: Clc1ccc(-c2nc(N3CCOCC3)n3ccncc23)cc1] | 4-[3-(4-Chlorophenyl)imidazo[1,5-a]pyrazin-1-yl]morpholine | 17 | 27% | LCMS (ES+) m/z = 315.1 (M + H)+. HPLC (method B): Rf 4.87 min, 100% purity. |
| 34 | 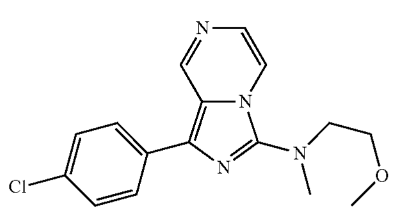 [SMILES: COCCN(C)c1nc(-c2ccc(Cl)cc2)c2cnccn12] | 3-(4-Chlorophenyl)-N-(2-methoxyethyl)-N-methylimidazo[1,5-a]pyrazin-1-amine | 18 | 7% | LCMS (ES+) m/z = 317.1 (M + H)+. HPLC (method B): Rf 5.08 min, 99.9% purity. |
| 35 | 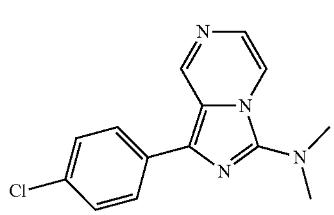 [SMILES: CN(C)c1nc(-c2ccc(Cl)cc2)c2cnccn12] | 3-(4-Chlorophenyl)-N,N-dimethylimidazo[1,5-a]pyrazin-1-amine | 19 | 59% | LCMS (ES+) m/z = 273.4 (M + H)+. HPLC (method B): Rf 4.95 min, 98.7% purity. |

TABLE 5-continued

POCl₃ cyclisations

| Ex | Structure | Name | Int | Yield | LCMS, HPLC |
|---|---|---|---|---|---|
| 36 | 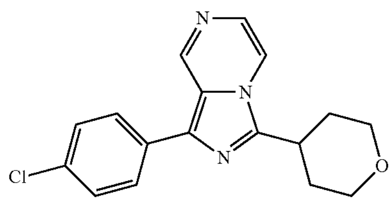 [SMILES: Clc1ccc(-c2nc(C3CCOCC3)n3ccncc23)cc1] | 3-(4-Chlorophenyl)-1-(oxan-4-yl)imidazo[1,5-a]pyrazine | 20 | 35% | LCMS (ES+) m/z = 314.4 (M + H)⁺. HPLC (method B): Rf 4.87 min, 98.9% purity. |
| 37 | 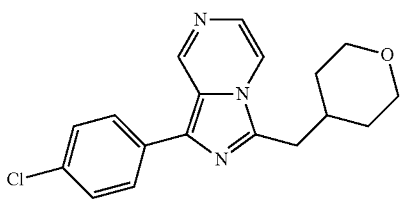 [SMILES: Clc1ccc(-c2nc(CC3CCOCC3)n3ccncc23)cc1] | 3-(4-Chlorophenyl)-1-(oxan-4-ylmethyl)imidazo[1,5-a]pyrazine | 21 | 23% | LCMS (ES+) m/z = 328.1 (M + H)⁺. HPLC (method B): Rf 4.88 min, 100% purity. |
| 38 | 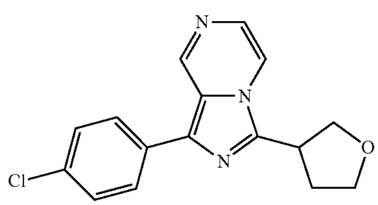 [SMILES: Clc1ccc(-c2nc(C3CCOC3)n3ccncc23)cc1] | 3-(4-Chlorophenyl)-1-(oxolan-3-yl)imidazo[1,5-a]pyrazine | 22 | 5.3% | LCMS (ES+) m/z = 300.1 (M + H)⁺. HPLC (method B): Rf 4.82 min, 100% purity. |
| 39 | 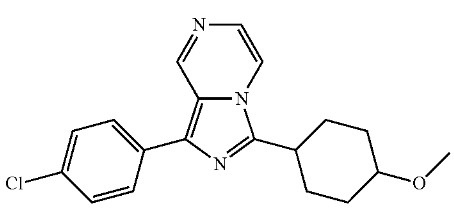 [SMILES: COC1CCC(c2nc(-c3ccc(Cl)cc3)c3cnccn23)CC1] | 3-(4-Chlorophenyl)-1-(4-methoxycyclohexyl)imidazo[1,5-a]pyrazine | 23 | 6% | LCMS (ES+) m/z = 342.1 (M + H)⁺. HPLC (method B): Rf 5.42 min, 98.2% purity. |

Example 40

3-(Oxan-4-yl)-1-phenyl-1H-pyrazolo[3,4-c]pyridine

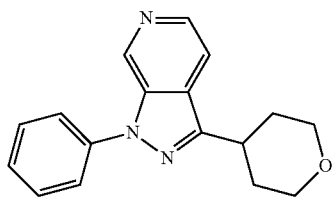 [SMILES: c1ccc(-n2nc(C3CCOCC3)c3ccncc32)cc1]

Intermediate 26 (245 mg, 1.21 mmol), Iodobenzene (162 µL, 1.45 mmol), copper (I) iodide (23.0 mg, 0.12 mmol), N,N'-dimethylethylenediamine (26.0 µL, 0.24 mmol) and potassium phosphate (537 mg, 2.53 mmol) were dissolved in DMF (5 mL) and heated in a microwave at 160° C. for 40 min. The reaction mixture was filtered through celite and concentrated in vacuo. The residue was dissolved in DCM (100 mL), washed with sat aq NaHCO₃ (100 mL), water (100 mL), dried (MgSO₄) and concentrated in vacuo. The residue was purified by reverse phase HPLC to give the title compound (20.5 mg, 6.1%) as a beige solid. HRMS (ESI+) calcd for C₁₇H₁₇N₃O, 280.1444. found 280.1442. HPLC (method B): Rf 4.64 min, 99% purity.

Examples 41-69

Examples 41-69 were prepared similarly to Example 40, by reacting Intermediates 26, 52-57 and 59-71 with the appropriate iodobenzene or bromobenzene; see Table 6 below.

TABLE 6

Aryl couplings

| Ex | Structure | Name | Int | Yield | HRMS (ES+)/LCMS, HPLC |
|---|---|---|---|---|---|
| 41 | 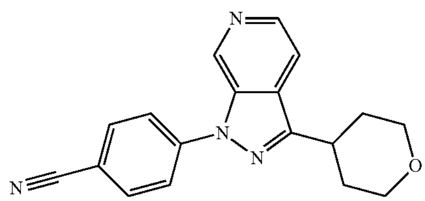 [SMILES: N#Cc1ccc(-n2nc(C3CCOCC3)c3ccncc32)cc1] | 4-[3-(Oxan-4-yl)-1H-pyrazolo[3,4-c]pyridin-1-yl]benzonitrile | 26 | 0.7% | Calcd for $C_{18}H_{16}N_4O$ 305.1397, found 305.1396. HPLC (method B): Rf 4.71 min, 100% purity. |
| 42 | 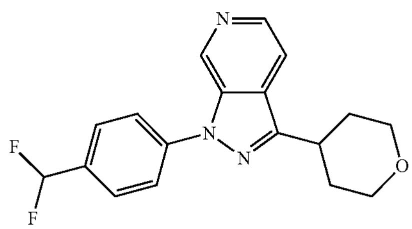 [SMILES: FC(F)c1ccc(-n2nc(C3CCOCC3)c3ccncc32)cc1] | 1-[4-(Difluoromethyl)phenyl]-3-(oxan-4-yl)-1H-pyrazolo[3,4-c]pyridine | 26 | 20% | Calcd for $C_{18}H_{17}F_2N_3O$ 330.1412, found 330.1416. HPLC (method B): Rf 5.00 min, 98.7% purity. |
| 43 | 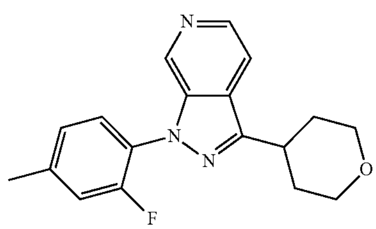 [SMILES: Cc1ccc(-n2nc(C3CCOCC3)c3ccncc32)c(F)c1] | 1-(2-Fluoro-4-methylphenyl)-3-(oxan-4-yl)-1H-pyrazolo[3,4-c]pyridine | 26 | 3.5% | Calcd for $C_{18}H_{18}FN_3O$ 312.1507, found 312.1510. HPLC (method B): Rf 4.96 min, 100% purity. |
| 44 | 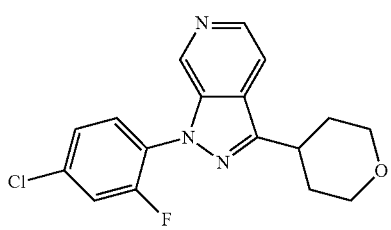 [SMILES: Fc1cc(Cl)ccc1-n1nc(C2CCOCC2)c2ccncc21] | 1-(4-Chloro-2-fluorophenyl)-3-(oxan-4-yl)-1H-pyrazolo[3,4-c]pyridine | 26 | 15% | Calcd for $C_{17}H_{15}ClFN_3O$ 332.0960, found 332.0964. HPLC (method B): Rf 5.32 min, 100% purity. |
| 45 | 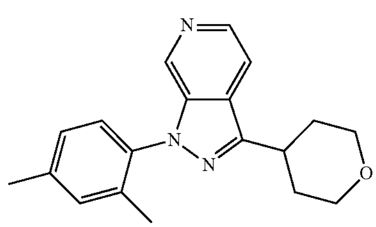 [SMILES: Cc1ccc(-n2nc(C3CCOCC3)c3ccncc32)c(C)c1] | 1-(2,4-Dimethylphenyl)-3-(oxan-4-yl)-1H-pyrazolo[3,4-c]pyridine | 26 | 8.9% | Calcd for $C_{19}H_{21}N_3O$ 308.1757, found 308.1760. HPLC (method B): Rf 5.18 min, 100% purity |
| 46 | 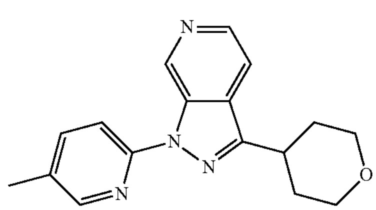 [SMILES: Cc1ccc(-n2nc(C3CCOCC3)c3ccncc32)nc1] | 5-Methyl-2-[3-(oxan-4-yl)-1H-pyrazolo[3,4-c]pyridin-1-yl]pyridine | 26 | 6.5% | Calcd for $C_{17}H_{18}N_4O$ 295.1553, found 295.1556. HPLC: Rf 5.02 min, 100% purity. |

TABLE 6-continued

Aryl couplings

| Ex | Structure | Name | Int | Yield | HRMS (ES+)/LCMS, HPLC |
|---|---|---|---|---|---|
| 47 | 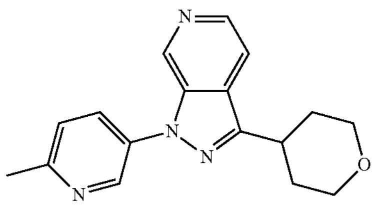 [SMILES: Cc1ccc(-n2nc(C3CCOCC3)c3ccncc32)cn1] | 2-Methyl-5-[3-(oxan-4-yl)-1H-pyrazolo[3,4-c]pyridin-1-yl]pyridine | 26 | 6.4% | Calcd for $C_{17}H_{18}N_4O$ 295.1553, found 295.1556. HPLC (method B): Rf 3.64 min, 100% purity. |
| 48 | 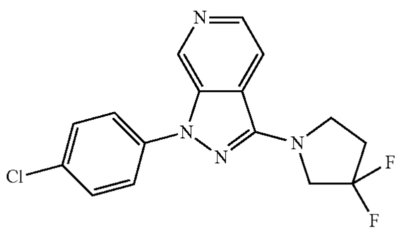 [SMILES: FC1(F)CCN(c2nn(-c3ccc(Cl)cc3)c3cnccc23)C1] | 1-[1-(4-Chlorophenyl)-1H-pyrazolo[3,4-c]pyridin-3-yl]-3,3-difluoropyrrolidine | 52 | 0.7% | Calcd for $C_{16}H_{13}ClF_2N_4$ 335.0873, found 335.0870. HPLC (method B): Rf 5.72 min, 96% purity. |
| 49 | 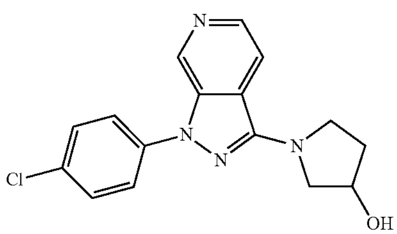 [SMILES: OC1CCN(c2nn(-c3ccc(Cl)cc3)c3cnccc23)C1] | 1-[1-(4-Chlorophenyl)-1H-pyrazolo[3,4-c]pyridin-3-yl]pyrrolidin-3-ol | 53 | 1.9% | Calcd for $C_{16}H_{15}ClN_4O$ 315.1007, found 315.1011. HPLC (method B): Rf 4.67 min, 100%. |
| 50 | 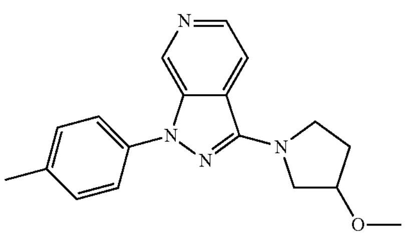 | 3-Methoxy-1-[1-(4-methylphenyl)-1H-pyrazolo[3,4-c]pyridin-3-yl]pyrrolidine | 54 | 17% | Calcd for $C_{18}H_{20}N_4O$ 309.1710, found 309.1712. HPLC (method B): Rf 5.16 min, 97% purity. |
| 51 | 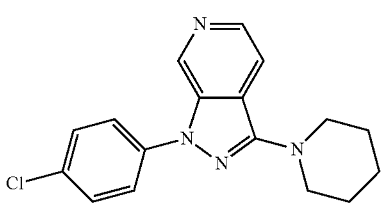 [SMILES: Clc1ccc(-n2nc(N3CCCCC3)c3ccncc32)cc1] | 1-[1-(4-Chlorophenyl)-1H-pyrazolo[3,4-c]pyridin-3-yl]piperidine | 55 | 5.0% | Calcd for $C_{17}H_{17}ClN_4$ 313.1215, found 313.1218. HPLC (method B): Rf 6.29 min, 100% purity. |
| 52 | 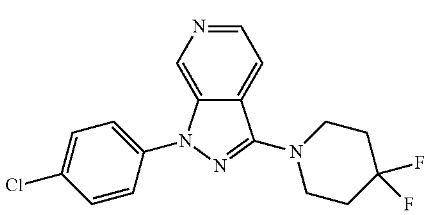 [SMILES: FC1(F)CCN(c2nn(-c3ccc(Cl)cc3)c3cnccc23)CC1] | 1-[1-(4-Chlorophenyl)-1H-pyrazolo[3,4-c]pyridin-3-yl]-4,4-difluoropiperidine | 56 | 3.9% | Calcd for $C_{17}H_{15}ClF_2N_4$ 349.1026, found 349.1029. HPLC (method B): Rf 5.94 min, 99% purity. |

TABLE 6-continued

Aryl couplings

| Ex | Structure | Name | Int | Yield | HRMS (ES+)/LCMS, HPLC |
|---|---|---|---|---|---|
| 53 | 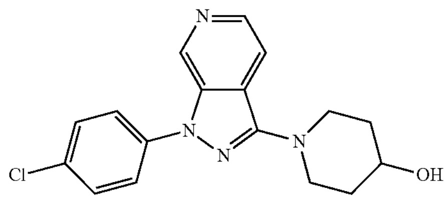 [SMILES: OC1CCN(c2nn(-c3ccc(Cl)cc3)c3cnccc23)CC1] | 1-[1-(4-Chlorophenyl)-1H-pyrazolo[3,4-c]pyridin-3-yl]piperidin-4-ol | 57 | 5.0% | Calcd for $C_{17}H_{17}ClN_4O$ 329.1164, found 329.1162. HPLC (method B): Rf 4.67 min, 100% purity. |
| 54 | 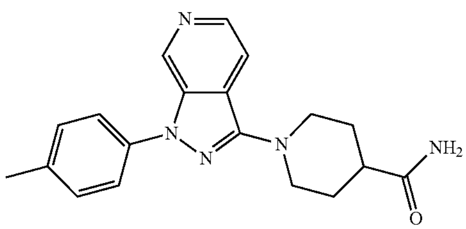 [SMILES: Cc1ccc(-n2nc(N3CCC(C(N)=O)CC3)c3ccncc32)cc1] | 1-[1-(4-Methylphenyl)-1H-pyrazolo[3,4-c]pyridin-3-yl]piperidine-4-carboxamide | 59 | 2.5% | Calcd for $C_{19}H_{21}N_5O$ 336.1827, found 336.1819. HPLC (method B): Rf 4.21 min, 100% purity. |
| 55 | 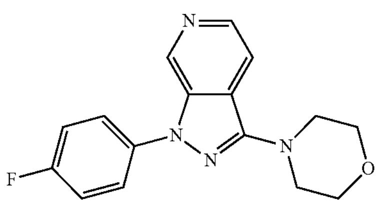 [SMILES: Fc1ccc(-n2nc(N3CCOCC3)c3ccncc32)cc1] | 4-[1-(4-Fluorophenyl)-1H-pyrazolo[3,4-c]pyridin-3-yl]morpholine | 60 | 2.7% | Calcd for $C_{16}H_{15}FN_4O$ 299.1303, found 299.1306. HPLC (method B): Rf 4.63 min, 100% purity. |
| 56 | 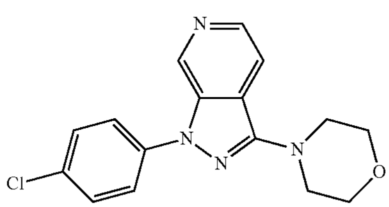 | 4-[1-(4-Chlorophenyl)-1H-pyrazolo[3,4-c]pyridin-3-yl]morpholine | 60 | 15% | Calcd for $C_{16}H_{15}ClN_4O$ 315.1007, found 315.1011. 100%, HPLC (method B): Rf 5.16 min, 100% purity. |
| 57 | 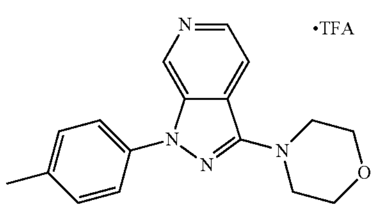 [SMILES: Cc1ccc(-n2nc(N3CCOCC3)c3ccncc32)cc1] | 2,2,2-Trifluoroacetic acid; 4-[1-(4-methylphenyl)-1H-pyrazolo[3,4-c]pyridin-3-yl]morpholine | 60 | 0.9% | LCMS (ES+): 295.0 (M + H)+. HPLC (method B): Rf 5.30 min, 99% purity. |
| 58 | 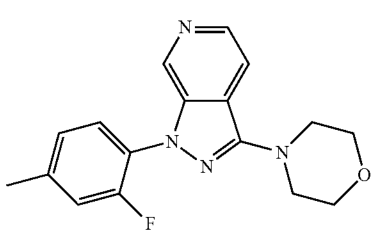 [SMILES: Cc1ccc(-n2nc(N3CCOCC3)c3ccncc32)c(F)c1] | 4-[1-(2-Fluoro-4-methylphenyl)-1H-pyrazolo[3,4-c]pyridin-3-yl]morpholine | 60 | 5.5% | Calcd for $C_{17}H_{17}FN_4O$ 313.1459, found 313.1463. HPLC (method B): Rf 4.85 min, 99% purity. |

TABLE 6-continued

Aryl couplings

| Ex | Structure | Name | Int | Yield | HRMS (ES+)/LCMS, HPLC |
|---|---|---|---|---|---|
| 59 | | 4-[1-(4-Chlorophenyl)-1H-pyrazolo[3,4-c]pyridin-3-yl]-2-methylmorpholine | 61 | 2.1% | Calcd for $C_{17}H_{17}ClN_4O$ 329.1164, found 329.1163. HPLC (method B): Rf 5.49 min, 98% purity. |
| 60 | | 4-[1-(4-Chlorophenyl)-1H-pyrazolo[3,4-c]pyridin-3-yl]-3-methylmorpholine | 62 | 8.8% | Calcd for $C_{17}H_{17}ClN_4O$ 329.1164, found 329.1167. HPLC (method B): Rf 5.39 min, 99% purity. |
| 61 | | 4-[1-(4-Methylphenyl)-1H-pyrazolo[3,4-c]pyridin-3-yl]-2-(2-methylpropyl)morpholine | 63 | 15% | Calcd for $C_{21}H_{26}N_4O$ 351.2179, found 351.2182. HPLC (method B): Rf 6.45 min, 100% purity. |
| 62 | | (2S,6R)-4-[1-(4-Chlorophenyl)-1H-pyrazolo[3,4-c]pyridin-3-yl]-2,6-dimethylmorpholine | 64 | 3.9% | Calcd for $C_{18}H_{19}ClN_4O$ 343.1320, found 343.1324. HPLC (method B): Rf 5.74 min, 99% purity. |
| 63 | | 3-[1-(4-Methylphenyl)-1H-pyrazolo[3,4-c]pyridin-3-yl]-8-oxa-3-azabicyclo[3.2.1]octane | 65 | 6.6% | Calcd for $C_{19}H_{20}N_4O$ 321.1710, found 321.1706. HPLC (method B): Rf 5.23 min, 99.6% purity. |
| 64 | | 2,2-Dimethyl-4-[1-(4-methylphenyl)-1H-pyrazolo[3,4-c]pyridin-3-yl]morpholine | 66 | 16% | Calcd for $C_{19}H_{22}N_4O$ 323.1866, found 323.1871. HPLC (method B): Rf 5.47 min, 99% purity. |

TABLE 6-continued

Aryl couplings

| Ex | Structure | Name | Int | Yield | HRMS (ES⁺)/LCMS, HPLC |
|---|---|---|---|---|---|
| 65 | 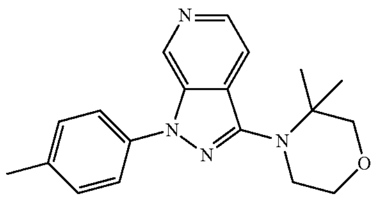 [SMILES: Cc1ccc(-n2nc(N3CCOCC3(C)C)c3ccncc32)cc1] | 3,3-Dimethyl-4-[1-(4-methylphenyl)-1H-pyrazolo[3,4-c]pyridin-3-yl]morpholine | 67 | 8.1% | Calcd for $C_{19}H_{22}N_4O$ 323.1866, found 323.1870. HPLC (method B): Rf 5.42 min, 100% purity. |
| 66 | 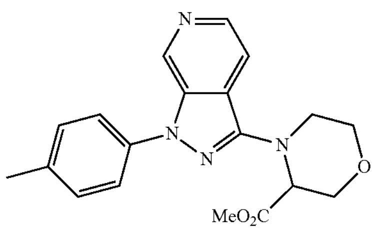 [SMILES: COC(=O)C1COCCN1c1nn(-c2ccc(C)cc2)c2cnccc12] | Methyl 4-[1-(4-methylphenyl)-1H-pyrazolo[3,4-c]pyridin-3-yl]morpholine-3-carboxylate | 68 | 44% | Calcd for $C_{19}H_{20}N_4O_3$ 353.1608, found 353.1611. HPLC (method B): Rf 4.98 min, 100% purity. |
| 67 | 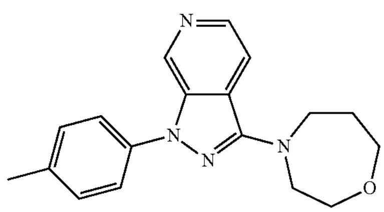 [SMILES: Cc1ccc(-n2nc(N3CCCOCC3)c3ccncc32)cc1] | 4-[1-(4-Methylphenyl)-1H-pyrazolo[3,4-c]pyridin-3-yl]-1,4-oxazepane | 69 | 23% | Calcd for $C_{18}H_{20}N_4O$ 309.1710, found 309.1713. HPLC (method B): Rf 4.96 min, 99% purity. |
| 68 | 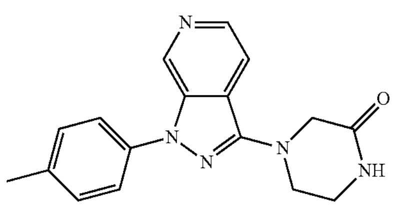 [SMILES: Cc1ccc(-n2nc(N3CCNC(=O)C3)c3ccncc32)cc1] | 4-[1-(4-Methylphenyl)-1H-pyrazolo[3,4-c]pyridin-3-yl]piperazin-2-one | 70 | 0.4% | LCMS (ES⁺): 308.0 (M + H)⁺. HPLC (method B): Rf 4.05 min, 99% purity. |
| 69 | 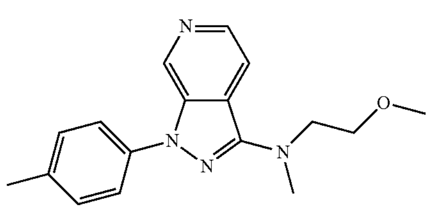 | N-(2-Methoxyethyl)-N-methyl-1-(4-methylphenyl)-1H-pyrazolo[3,4-c]pyridin-3-amine | 71 | 11% | Calcd for $C_{17}H_{20}N_4O$ 297.1710, found 297.1711. HPLC (method B): Rf 5.18 min, 100% purity. |

Example 70

1-[1-(4-Chlorophenyl)-1H-pyrazolo[3,4-c]pyridin-3-yl]piperazine

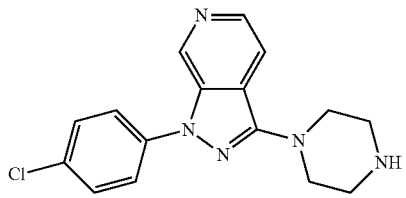

Intermediate 76 (140 mg, 0.34 mmol) was dissolved in 1.25M HCl in EtOH (5 mL) and stirred overnight. The solvents were removed in vacuo to give a yellow gum (141 mg). 47 ing of this material was dissolved in water (10 mL) and washed with DCM (2×10 mL). The aqueous phase was concentrated in vacuo, de-salted ($K_2CO_3$ in DCM) and purified by reverse phase HPLC to give the title compound as a light yellow solid (6.42 mg, 17%). HRMS (ESI+) calcd for $C_{16}H_{16}ClN_5$ 314.1167. found 314.1171. HPLC (method B): Rf 3.81 min, 99% purity.

Example 71

1-[1-(4-Chlorophenyl)-1H-pyrazolo[3,4-c]pyridin-3-yl]piperidin-4-amine

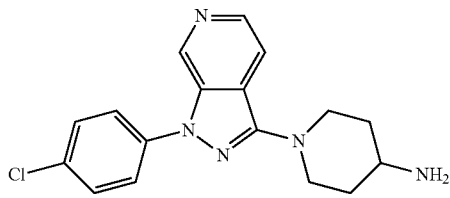 [SMILES: NC1CCN(c2nn(-c3ccc(Cl)cc3)c3cnccc23)CC1]

Example 71 was prepared similarly to Example 70, using Intermediate 77 instead of Intermediate 76, to give the title compound as a yellow solid (88%). HRMS (ESI+) calcd for $C_{17}H_{18}ClN_5$ 328.1323. found 328.1326. HPLC (method B): Rf 3.92 min, 97% purity.

Example 72

{4-[1-(4-Methylphenyl)-1H-pyrazolo[3,4-c]pyridin-3-yl]morpholin-2-yl}methanamine

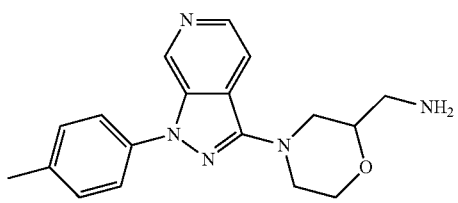 [SMILES: Cc1ccc(-n2nc(N3CCOC(CN)C3)c3ccncc32)cc1]

Example 72 was prepared similarly to Example 70, using Intermediate 78 instead of Intermediate 76, to give the title compound as a yellow solid (38%). HRMS (ESI+) calcd for $C_{18}H_{21}N_5O$, 324.1819. found 324.1823. HPLC (method B): Rf 3.71 min, 98% purity.

Example 73 tert-Butyl N-(2-methoxyethyl)-N-[1-(4-methylphenyl)-1H-pyrazolo[3,4-c]pyridin-3-yl]carbamate

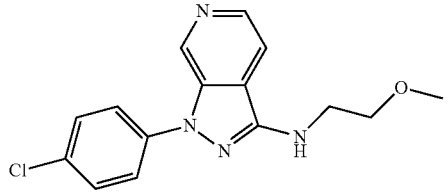 [SMILES: COCCNc1nn(-c2ccc(Cl)cc2)c2cnccc12]

Example 73 was prepared similarly to Example 70, using Intermediate 79 instead of Intermediate 76, to give the title compound as a yellow solid (5.4%). HRMS (ESI+) calcd for $C_{16}H_{18}N_4O$, 283.1553. found 283.1556. HPLC (method B): Rf 4.88 min, 99% purity.

Example 74

1-[1-(4-Methylphenyl)-1H-pyrazolo[3,4-c]pyridin-3-yl]piperidin-4-ol

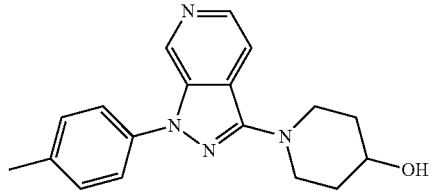 [SMILES: Cc1ccc(-n2nc(N3CCC(O)CC3)c3ccncc32)cc1]

Intermediate 80 (200 mg, 0.57 mmol) was dissolved in MeOH (4 mL), $K_2CO_3$ (315 mg, 2.28 mmol) was added and the reaction mixture was stirred for 3 h. The reaction mixture was concentrated in vacuo and partitioned between DCM (20 mL) and water (10 mL). The aqueous phase was extracted with DCM (3×50 mL) and the combined organic fractions were dried ($MgSO_4$) and concentrated in vacuo to yield the title compound as an off white solid (168 mg, 95%). HRMS (ESI+) calcd for $C_{18}H_{20}N_4O$, 309.1710. found 309.1713. HPLC: Rf 4.40 min, 100% purity.

Example 75

1-[1-(4-Chlorophenyl)-1H-pyrazolo[3,4-c]pyridin-3-yl]-4-(1H-pyrazol-3-ylmethyl)piperazine

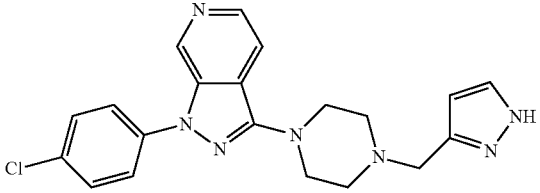 [SMILES: Clc1ccc(-n2nc(N3CCN(Cc4cc[nH]n4)CC3)c3ccncc32)cc1]

Example 70 (48.0 mg, 0.12 mmol) was dissolved in DCM (3 mL) and 1H-pyrazole-3-carbaldehyde (14.3 mg, 0.15 mmol) and NaBH(OAc)$_3$ (31.6 mg, 0.15 mmol) were added. The reaction mixture was stirred for 2 days. DIPEA (43.2 µL, 0.25 mmol), 1H-pyrazole-3-carbaldehyde (14.3 mg, 0.15 mmol) and NaBH(OAc)$_3$ (31.6 mg, 0.15 mmol) were added and the reaction mixture was stirred overnight. The reaction mixture was diluted with DCM (10 mL) and quenched with water (5 mL). The organic fraction was washed with sat aq Na₂CO₃ (10 mL), dried (MgSO₄) and concentrated in vacuo. The residue was purified by reverse phase HPLC to give the title compound as a yellow solid (13.9 mg, 28%). HRMS (ESI+) calcd for C₂₀H₂₀ClN₇ 394.1541. found 394.1543. HPLC (method B): Rf 3.99 min, 97% purity.

Example 76 tert-Butyl N-(3-{4-[1-(4-chlorophenyl)-1H-pyrazolo[3,4-c]pyridin-3-yl]piperazin-1-yl}-3-oxopropyl)carbamate

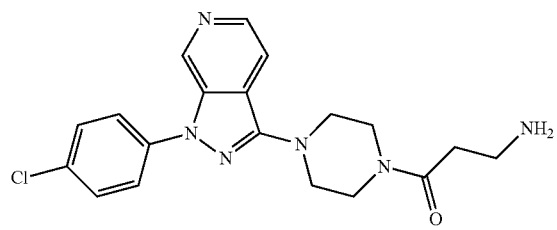 [SMILES: NCCC(=O)N1CCN(c2nn(-c3ccc(Cl)cc3)c3cnccc23)CC1]

3-tert-Butoxycarbonylaminopropionic acid (29.2 mg, 0.15 mmol) was dissolved in DMF (2 mL) and HBTU (55.3 mg, 0.15 mmol) was added. The reaction mixture was stirred for 1 h and then Example 70 (47.0 mg, 0.12 mmol) and DIPEA (25.4 µL, 0.15 mmol) were added. The reaction mixture was stirred for 2 h and concentrated in vacuo. The residue was diluted with DCM (10 mL) and washed with sat aq NH₄Cl (5 mL) and sat aq Na₂CO₃ (5 mL), dried (MgSO₄) and concentrated in vacuo. The residue was purified by column chromatography to give a yellow foam (48.0 mg) which was dissolved in 1.25 M HCl in EtOH (5 mL). The reaction mixture was stirred overnight and concentrated in vacuo. The residue was dissolved in water (10 mL), washed with DCM (2×10 mL) and the solvents were removed in vacuo. The residue was de-salted (K₂CO₃ in DCM) and purified by reverse phase HPLC to give the title compound as a yellow gum (8.71 mg, 19%). HRMS (ESI+) calcd for C₁₉H₂₁ClN₆O, 385.1538. found 385.1542. HPLC (method B): Rf 3.98 min, 97% purity.

Example 77

4-[1-(4-Methylphenyl)-1H-pyrazolo[3,4-c]pyridin-3-yl]morpholine-3-carboxamide

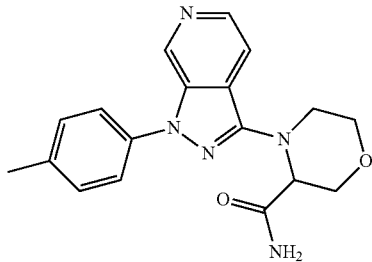 [SMILES: Cc1ccc(-n2nc(N3CCOCC3C(N)=O)c3ccncc32)cc1]

Intermediate 81 (345 mg, 0.92 mmol) was dissolved in DMF (4.4 mL), HBTU (419 mg, 1.10 mmol) was added and the reaction mixture was stirred for 1 h. NH₄Cl (59.1 mg, 1.10 mmol) and DIPEA (401 µL, 2.76 mmol) were added and the reaction mixture was stirred overnight. The reaction mixture was concentrated in vacuo and the residue was diluted with DCM (20 mL), washed with sat aq NH₄Cl (5 mL) and sat aq Na₂CO₃ (5 mL), dried (MgSO₄) and concentrated in vacuo. The residue was purified by column chromatography to yield the title compound as an orange solid (1.98 mg, 0.6%). HRMS (ESI+) calcd for C₁₈H₁₉N₅O₂ 338.1612. found 338.1614. HPLC (method B): Rf 4.02 min, 97% purity.

Example 78

4-[1-(4-Methylphenyl)-1H-pyrazolo[3,4-c]pyridin-3-yl]-3-[(morpholin-4-yl)carbonyl]morpholine

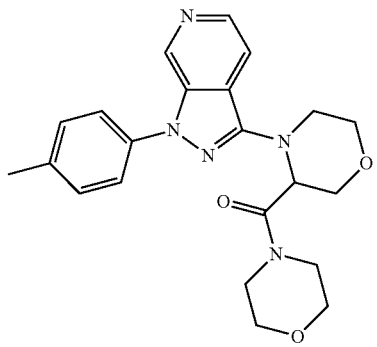 [SMILES: Cc1ccc(-n2nc(N3CCOCC3C(=O)N3CCOCC3)c3ccncc32)cc1]

Intermediate 81 (345 mg, 0.92 mmol) was dissolved in DMF (4.4 mL), HBTU (419 mg, 1.10 mmol) was added and the reaction mixture was stirred for 1 h. Morpholine (96.6 µL, 1.10 mmol) and DIPEA (401 µL, 2.76 mmol) were added and the reaction mixture was stirred overnight. The reaction mixture was concentrated in vacuo and the residue was diluted with DCM (20 mL), washed with sat aq NH₄Cl (5 mL) and sat aq Na₂CO₃ (5 mL), dried (MgSO₄) and concentrated in vacuo. The residue was purified by column chromatography to yield the title compound as a light yellow gum (1.02 mg, 0.3%). HRMS (ESI+) calcd for C₂₂H₂₅N₅O₃ 408.2029. found 408.2030. HPLC (method B): Rf 4.27 min, 98% purity.

Example 79

N-(2-Aminoethyl)-4-[1-(4-methylphenyl)-1H-pyrazolo[3,4-c]pyridin-3-yl]morpholine-3-carboxamide dihydrochloride

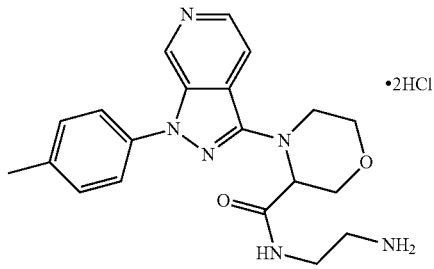 [SMILES: Cc1ccc(-n2nc(N3CCOCC3C(=O)NCCN)c3ccncc32)cc1]

Intermediate 81 (345 mg, 0.92 mmol) was dissolved in DMF (4.4 mL), HBTU (419 mg, 1.10 mmol) was added and the reaction mixture was stirred for 1 h. tert-Butyl N-(2-aminoethyl)carbamate (177 mg, 1.10 mmol) and DIPEA (401 µL, 2.76 mmol) were added and the reaction mixture was stirred overnight. The reaction mixture was concentrated in vacuo and the residue was diluted with DCM (20 mL), washed with sat aq NH₄Cl (5 mL) and sat aq Na₂CO₃ (5 mL), dried (MgSO₄) and concentrated in vacuo. The residue was purified by column chromatography and dissolved in 1.25 M HCl in EtOH (4 mL). The reaction mixture was stirred for 1 h and the solvents were removed in vacuo to yield the title compound as an orange solid (2.12 mg, 56%). HRMS (ESI+)

calcd for $C_{20}H_{24}N_6O_2$ 381.2034. found 381.2038. HPLC (method B): Rf 3.57 min, 100% purity.

Example 80

1-(4-Chlorophenyl)-3-(oxan-4-yl)-1H-pyrazolo[3,4-c]pyridine

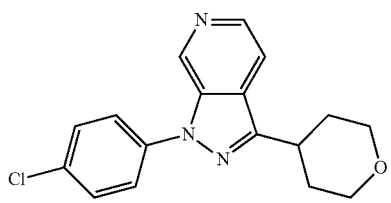 [SMILES: Clc1ccc(-n2nc(C3CCOCC3)c3ccncc32)cc1]

Intermediate 87 (98.0 mg, 0.43 mmol) and (4-chloro-phenyl)-hydrazine (171 mg, 0.96 mmol) were dissolved in NMP (1 mL) and heated in a microwave at 160° C. for 20 min. $K_2CO_3$ (120 mg, 0.87 mmol), CuI (4.10 mg, 0.02 mmol) and N,N-dimethylethylenediamine (4.67 mL, 0.04 mmol) were added and the reaction mixture was heated in a microwave at 160° C. for 1 h. The residue was purified using an Isolute MP-TsOH cartridge, by normal phase column chromatography and by reverse phase column chromatography to give the title compound as an off white solid (23.0 mg, 17%). HRMS (ESI+) calcd for $C_{17}H_{16}ClN_3O$, 314.1055. found 314.1059. HPLC (method B): Rf 4.88 min, 99% purity.

Examples 81-88

Examples 81-88 were prepared similarly to Example 80, by reacting 3-halo-4-[(pyridin-4-yl)carbonyl]intermediates with the appropriate arylhydrazine; see Table 7 below.

TABLE 7

Condensation of arylhydrazines with 3-halo-4-[(pyridin-4-yl)carbonyl] intermediates

| Ex | Structure | Name | Int | Yield | HRMS (ESI+)/LCMS, HPLC |
|---|---|---|---|---|---|
| 81 | 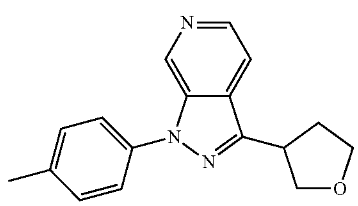 [SMILES: Cc1ccc(-n2nc(C3CCOC3)c3ccncc32)cc1] | 1-(4-Methylphenyl)-3-(oxolan-3-yl)-1H-pyrazolo[3,4-c]pyridine | 88 | 14% | Calcd for $C_{17}H_{17}N_3O$ 280.1444, found 280.1447. HPLC (method B): Rf 4.76 min, 100% purity. |
| 82 | 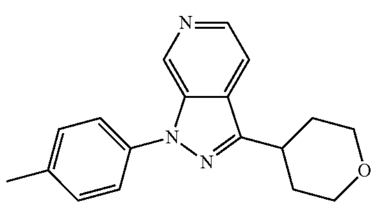 [SMILES: Cc1ccc(-n2nc(C3CCOCC3)c3ccncc32)cc1] | 1-(4-Methylphenyl)-3-(oxan-4-yl)-1H-pyrazolo[3,4-c]pyridine | 25 | 12% | Calcd for $C_{18}H_{19}N_3O$ 294.1604, found 294.1601. HPLC (method B): Rf 5.03 min, 100% purity. |
| 83 | 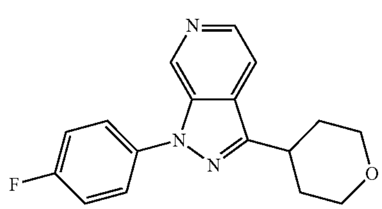 | 1-(4-Fluorophenyl)-3-(oxan-4-yl)-1H-pyrazolo[3,4-c]pyridine | 25 | 13% | Calcd for $C_{17}H_{16}FN_3O$ 298.1353, found 298.1350. HPLC (method B): Rf 4.76 min, 100% purity. |
| 84 | 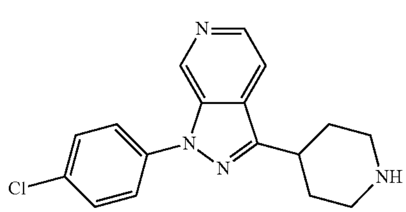 [SMILES: Clc1ccc(-n2nc(C3CCNCC3)c3ccncc32)cc1] | 4-[1-(4-Chlorophenyl)-1H-pyrazolo[3,4-c]pyridin-3-yl]piperidine | 95 | 2.2%* | LCMS (ES+): 313.0 (M + H)+. HPLC (method B): Rf 3.73 min, 100% purity. |

TABLE 7-continued

Condensation of arylhydrazines with 3-halo-4-[(pyridin-4-yl)carbonyl] intermediates

| Ex | Structure | Name | Int | Yield | HRMS (ESI⁺)/LCMS, HPLC |
|----|-----------|------|-----|-------|------------------------|
| 85 | 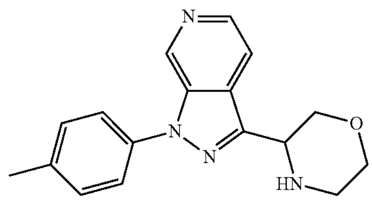 [SMILES: Cc1ccc(-n2nc(C3COCCN3)c3ccncc32)cc1] | 3-[1-(4-Methylphenyl)-1H-pyrazolo[3,4-c]pyridin-3-yl]morpholine | 89 | 0.4% | Calcd for $C_{17}H_{18}N_4O$ 295.1553, found 295.1556. HPLC (method B): Rf 3.51 min, 97.6% purity. |
| 86 | 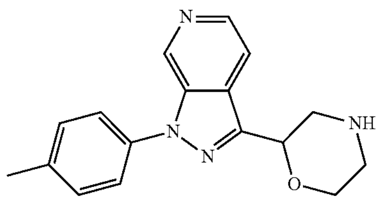 [SMILES: Cc1ccc(-n2nc(C3CNCCO3)c3ccncc32)cc1] | 2-[1-(4-Methylphenyl)-1H-pyrazolo[3,4-c]pyridin-3-yl]morpholine | 90 | 2.6% | Calcd for $C_{17}H_{18}N_4O$ 295.1553, found 295.1556. HPLC (method B): Rf 3.54 min, 99% purity. |
| 87 | 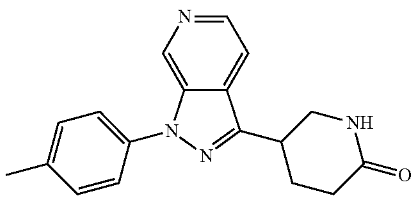 [SMILES: Cc1ccc(-n2nc(C3CCC(=O)NC3)c3ccncc32)cc1] | 5-[1-(4-Methylphenyl)-1H-pyrazolo[3,4-c]pyridin-3-yl]piperidin-2-one | 91 | 21% | LCMS (ES⁺): 307.1 (M + H)+. HPLC (method B): Rf 4.03 min, 97.6% purity. |
| 88 | 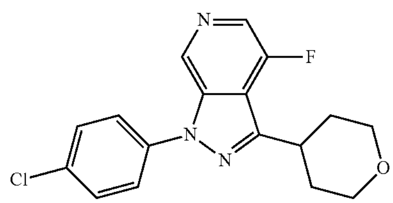 [SMILES: Fc1cncc2c1c(C1CCOCC1)nn2-c1ccc(Cl)cc1] | 1-(4-Chlorophenyl)-4-fluoro-3-(oxan-4-yl)-1H-pyrazolo[3,4-c]pyridine | 92 | 14% | Calcd for $C_{17}H_{15}ClFN_3O$ 332.0960, found 332.0964. HPLC (method B): Rf 7.17 min, 99% purity. |

*Following Boc deprotection with TFA

Example 89

4-[1-(4-Chlorophenyl)-1H-pyrazolo[3,4-c]pyridin-3-yl]-1-(1H-pyrazol-3-ylmethyl)piperidine

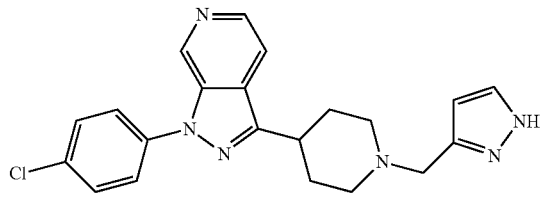 [SMILES: Clc1ccc(-n2nc(C3CCN(Cc4cc[nH]n4)CC3)c3ccncc32)cc1]

Example 84 (75.0 mg, 0.24 mmol) was dissolved in DCM (10 mL) and 1H-pyrazole-3-carbaldehyde (55.3 mg, 0.58 mmol), AcOH (14.4 µL, 0.25 mmol) and NaBH(OAc)₃ (152 mg, 0.72 mmol) were added. The reaction mixture stirred for 18 h, diluted with DCM (20 mL) and quenched with water (10 mL). The organic fraction was washed with sat aq $Na_2CO_3$ (10 mL), dried (MgSO₄) and concentrated in vacuo. The residue was purified by reverse phase chromatography to give the title compound as a white solid (8.14 mg, 8.6%). HRMS (ESI+) calcd for $C_{21}H_{21}ClN_6$ 393.1589. found 393.1589. HPLC (method B): Rf 3.90 min, 99% purity.

Example 90

1-Butyl-4-[1-(4-chlorophenyl)-1H-pyrazolo[3,4-c]pyridin-3-yl]piperidine

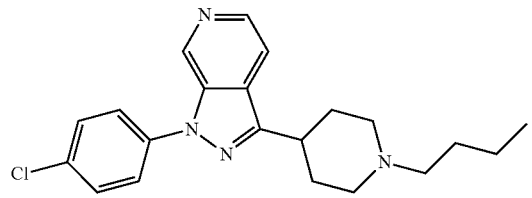 [SMILES: CCCCN1CCC(c2nn(-c3ccc(Cl)cc3)c3cnccc23)CC1]

Example 90 was prepared similarly to Example 89, using butanal instead of 1H-pyrazole-3-carbaldehyde, to give the title compound as a colourless gum (6.8%). HRMS (ESI+) calcd for $C_{21}H_{25}ClN_4$ 369.1841. found 369.1845. HPLC (method B): Rf 4.35 min, 99% purity.

Example 91

4-[1-(4-Chlorophenyl)-1H-pyrazolo[3,4-c]pyridin-3-yl]-N,N-dimethylpiperidine-1-carboxamide

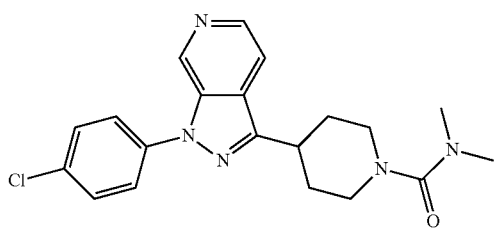 [SMILES: CN(C)C(=O)N1CCC(c2nn(-c3ccc(Cl)cc3)c3cnccc23)CC1]

Example 84 (75.0 mg, 0.24 mmol) was dissolved in DCM (10 mL), N,N-dimethylcarbamoyl chloride (26.4 µL, 0.26 mmol) and triethylamine (100 µL, 0.72 mmol) were added and the reaction mixture was stirred for 18 h. The reaction mixture was diluted with DCM (20 mL) and quenched with water (10 mL). The organic fraction was washed with sat aq $Na_2CO_3$ (10 mL), dried ($MgSO_4$) and concentrated in vacuo. The residue was purified by reverse phase chromatography to give the title compound as a white solid (8.17 mg, 8.9%). HRMS (ESI+) calcd for $C_{20}H_{22}ClN_5O$, 384.1586. found 384.1589. HPLC (method B): Rf 5.17 min, 100% purity.

Example 92

Ethyl 4-[1-(4-chlorophenyl)-1H-pyrazolo[3,4-c]pyridin-3-yl]piperidine-1-carboxylate

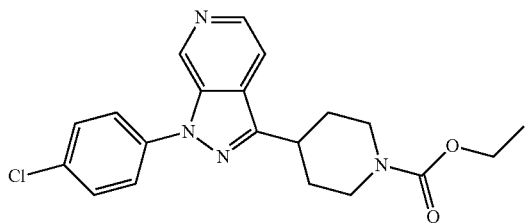 [SMILES: CCOC(=O)N1CCC(c2nn(-c3ccc(Cl)cc3)c3cnccc23)CC1]

Example 84 (75.0 mg, 0.24 mmol) was dissolved in DCM (10 mL), chloro(ethoxy)methanone (27.5 µL, 0.29 mmol) and triethylamine (100 µL, 0.72 mmol) were added and the reaction mixture was stirred for 18 h. The reaction mixture was diluted with DCM (20 mL) and quenched with water (10 mL). The organic fraction was washed with sat aq $Na_2CO_3$ (10 mL), dried ($MgSO_4$) and concentrated in vacuo. The residue was purified by reverse phase column chromatography to give the title compound as a white solid (12.1 mg, 13%). HRMS (ESI+) calcd for $C_{20}H_{21}ClN_4O_2$ 385.1426. found 385.1428. HPLC (method B): Rf 5.61 min, 100% purity.

Example 93

3-Amino-1-{4-[1-(4-chlorophenyl)-1H-pyrazolo[3,4-c]pyridin-3-yl]piperidin-1-yl}propan-1-one dihydrochloride

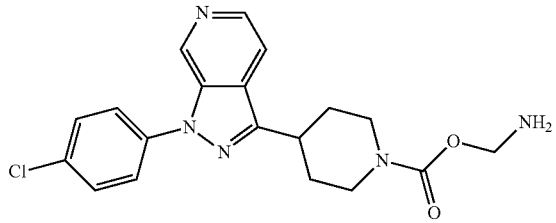

Example 93 was prepared similarly to Example 76, using Example 84 instead of Example 70, to give the title compound as a yellow solid (24%). HRMS (ESI+) calcd for $C_{20}H_{22}ClN_5O$, 384.1586. found 384.1591. HPLC (method B): Rf 3.91 min, 99% purity.

Example 94

1-(4-Chlorophenyl)-4-methoxy-3-(oxan-4-yl)-1H-pyrazolo[3,4-c]pyridine

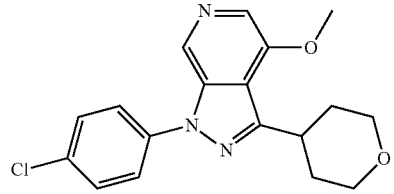

Example 88 (110 mg, 0.33 mmol) was dissolved in MeOH (5 mL), NaOMe (125 mg, 2.32 mmol) was added and the reaction mixture was heated using a microwave at 150° C. for 50 min. Further NaOMe (125 mg, 2.32 mmol) was added and the reaction mixture was heated using a microwave at 150° C. for 30 min, then poured into 10% aq citric acid (50 mL) and extracted with EtOAc (2×50 mL). The combined organic fractions were dried ($MgSO_4$) and concentrated in vacuo. The residue was purified by normal phase column chromatography and trituration with MeOH to give the title compound as a light yellow solid (29.0 mg, 25%). HRMS (ESI+) calcd for $C_{18}H_{18}ClN_3O_2$ 344.1160. found 344.1164. HPLC (method B): Rf 5.45 min, 99% purity.

Example 95

1-(4-Chlorophenyl)-3-(oxan-4-yl)-1H-pyrazolo[3,4-c]pyridin-4-ol

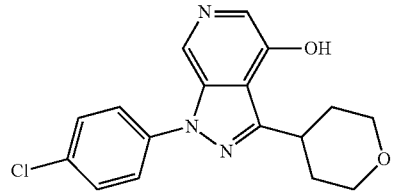 [SMILES: Oc1cncc2c1c(C1CCOCC1)nn2-c1ccc(Cl)cc1]

Example 88 (105 mg, 0.32 mmol) was suspended in water (5 mL) and KOH (177 mg, 3.16 mmol) was added. The reaction mixture was heated using a microwave at 200° C. for min then poured into 10% aq citric acid (50 mL) and extracted with EtOAc (2×100 mL). The combined organic fractions were dried (MgSO$_4$) and concentrated in vacuo. The residue was purified by reverse phase HPLC to give the title compound as a white solid (20.2 mg, 19%). HRMS (ESI+) calcd for C$_{17}$H$_{16}$ClN$_3$O$_2$ 330.1004. found 330.1001. HPLC (method B): Rf 5.06 min, 100% purity.

Example 96

1-(4-Chlorophenyl)-5-methoxy-3-(oxan-4-yl)-H-pyrazolo[3,4-c]pyridine

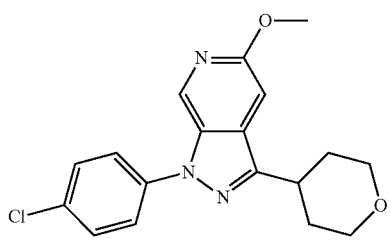 [SMILES: COc1cc2c(C3CCOCC3)nn(-c3ccc(Cl)cc3)c2cn1]

Intermediate 96 (110 mg, 0.33 mmol) was dissolved in MeOH (2.5 mL), NaOMe (125 mg, 2.32 mmol) was added and the reaction mixture was heated using a microwave at 150° C. for 2.5 h, then poured into 10% citric acid solution (50 mL). The precipitate was collected by filtration and purified by normal phase column chromatography and recrystallisation from MeOH to give the title compound as a white solid (36.2 mg, 32%). HRMS (ESI+) calcd for C$_{18}$H$_{18}$ClN$_3$O$_2$ 344.1160. found 344.1164. HPLC (method B): Rf 7.52 min, 99% purity.

Example 97

1-(4-Chlorophenyl)-3-(oxan-4-yl)-1H,5H,6H-pyrazolo[3,4-c]pyridin-5-one

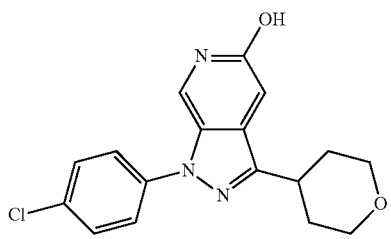

Intermediate 96 (100 ing, 0.30 mmol) was suspended in water (5 mL), KOH (169 mg, 3.01 mmol) was added and the reaction mixture was heated using a microwave at 100° C. for 1 h, at 150° C. for 30 min and at 200° C. for 30 min. The reaction mixture was poured into 10% aq citric acid (50 mL) and the precipitate was collected by filtration, washed with water and recrystallised twice from EtOH to give the title compound as a light yellow solid (15.6 mg, 16%). HRMS (ESI+) calcd for C$_{17}$H$_{16}$ClN$_3$O$_2$ 330.1004. found 330.1000. HPLC (method B): Rf 5.74 min, 99% purity.

Example 98

5-(4-Chlorophenyl)-7-(oxan-4-yl)-5H-pyrrolo[3,2-d]pyrimidine

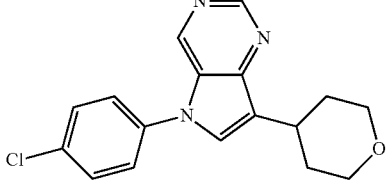

Intermediate 101 (52.0 mg, 0.26 mmol), 4-chloro-iodo-benzene (73.2 mg, 0.31 mmol), CuI (14.6 mg, 0.08 mmol), N,N'-dimethylethylenediamine (8.27 µL, 0.08 mmol) and potassium phosphate (92.3 mg, 0.43 mmol) were suspended in DMF (1.5 mL) and heated under reflux at 110° C. for 18 h. The reaction mixture was cooled to room temperature and concentrated in vacuo. The residue was purified by normal phase column chromatography and reverse phase column chromatography to give the title compound as a white solid (16.1 mg, 20%). HRMS (ESI+) calcd for C$_{17}$H$_{16}$ClN$_3$O, 314.1055. found 314.1058. HPLC (method B): Rf 5.22 min, 99% purity.

Example 99

1-(4-Chlorophenyl)-3-(oxan-4-yl)-1H-pyrazolo[4,3-d]pyrimidine

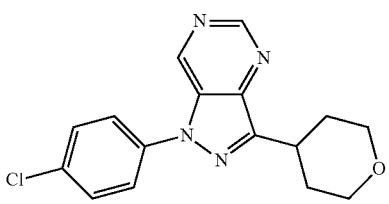

Intermediate 102 (500 mg, 2.21 mmol) and (4-chlorophenyl)hydrazine hydrochloride (434 mg, 2.43 mmol) were dissolved in EtOH (10 mL) and AcOH (2 mL), and stirred for 18 h. The solvents were removed in vacuo and the residue was dissolved in DCM (50 mL) and washed with sat aq Na$_2$CO$_3$ (50 mL). The aqueous layer was extracted with DCM (50 mL) and the combined organic fractions were dried (MgSO$_4$) and concentrated in vacuo. The residue was dissolved in DMF (10 mL) and Et$_3$N (922 µL, 6.62 mmol) was added. The reaction mixture was heated using a microwave at 150° C. for 30 min. The solvents were removed in vacuo and the residue was purified by normal phase column chromatography to give the title compound as a white solid (137 mg, 20%). HRMS Intermediate 103 (156 mg, 0.77 mmol), 1-fluoro-4-iodo-benzene (206 mg, 0.93 mmol), CuI (14.7 mg, 0.08 mmol), N,N'-dimethylethylenediamine (16.6 µL, 0.15 mmol) and potassium phosphate (344 mg, 1.62 mmol) were dissolved in DMF (5 mL) and heated in a microwave at 160° C. for 40 min. The reaction mixture was cooled to room temperature, filtered through celite and concentrated in vacuo. The residue was dissolved in DCM (100 mL), washed with sat aq NaHCO3 (100 mL), water (100 mL), dried (MgSO4) and concentrated in vacuo. The residue was purified by reverse phase HPLC to give the title compound as a red gum (4.34 mg, 1.9%). HRMS (ESI+) calcd for C$_{18}$H$_{17}$FN$_2$O, 297.1398. found 297.1401. HPLC (method B): Rf 4.74 min, 100% purity. (ESI+) calcd for C$_{16}$H$_{15}$ClN$_4$O, 315.1007. found 315.1011. HPLC (method B): Rf 4.45 min, 100% purity.

Example 100

1-(4-Fluorophenyl)-3-(oxan-4-yl)-1H-pyrrolo[2,3-c]pyridine

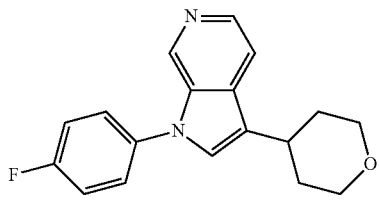 [SMILES: Fc1ccc(-n2cc(C3CCOCC3)c3ccncc32)cc1]

Examples 101-103

Examples 101-103 were prepared similarly to Example 100, by reacting Intermediate 103 with the appropriate iodobenzene or bromobenzene; see Table 8 below.

Example 104

4-[1-(4-Chlorophenyl)-1H-pyrrolo[2,3-c]pyridin-3-yl]morpholine 2,2,2-trifluoroacetic acid

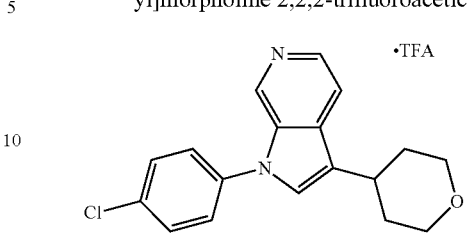

Intermediate 105 (156 mg, 0.64 mmol) was dissolved in MeCN (3 mL) and KI (21.3 mg, 0.13 mmol) and dichlorodiethyl ether (75.0 μL, 0.64 mmol) were added. The reaction mixture was heated using a microwave at 150° C. for 30 min.

TABLE 8

Aryl couplings

| Ex | Structure | Name | Yield | HRMS (ES+), HPLC |
|---|---|---|---|---|
| 101 | 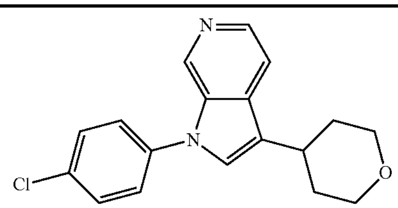 | 1-(4-Chlorophenyl)-3-(oxan-4-yl)-1H-pyrrolo[2,3-c]pyridine | 6% | Calcd for $C_{18}H_{17}ClN_2O$ 313.1102, found 313.1105. HPLC (method B): Rf 4.67 min, 99.8% purity. |
| 102 | 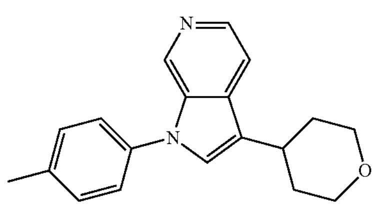 [SMILES: Cc1ccc(-n2cc(C3CCOCC3)c3ccncc32)cc1] | 1-(4-Methylphenyl)-3-(oxan-4-yl)-1H-pyrrolo[2,3-c]pyridine | 15% | Calcd for $C_{19}H_{20}N_2O$ 293.1648, found 293.1652. HPLC (method B): Rf 5.05 min, 98% purity. |
| 103 | 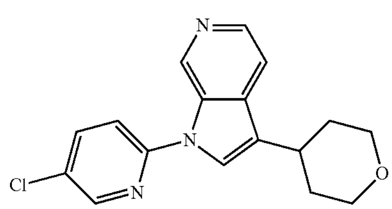 [SMILES: Clc1ccc(-n2cc(C3CCOCC3)c3ccncc32)nc1] | 5-Chloro-2-[3-(oxan-4-yl)-1H-pyrrolo[2,3-c]pyridin-1-yl]pyridine | 0.8% | Calcd for $C_{17}H_{16}ClN_3O$ 314.1055, found 314.1055. HPLC (method B): Rf 4.92 min, 100% purity. |

NaH (76.8 mg, 60% in mineral oil, 1.92 mmol) was added and the reaction mixture was heated using a microwave at 150° C. for 15 min. The solvents were removed in vacuo and the residue was purified by reverse phase HPLC to give the title compound as a brown solid (5.10 mg, 1.9%). HRMS (ESI+) calcd for $C_{17}H_{16}ClN_3O$, 314.1055. found 314.1057. HPLC (method B): Rf 4.55 min, 97% purity.

Example 105

2,2,2-Trifluoroacetic acid; 4-amino-1-{4-[1-(4-chlorophenyl)-1H-pyrrolo[2,3-c]pyridin-3-yl]piperidin-1-yl}butan-1-one

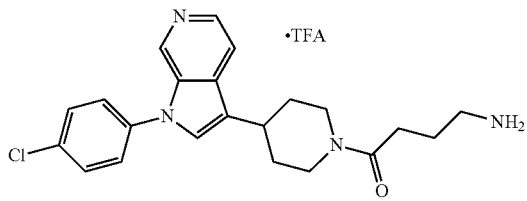 [SMILES: NCCCC(=O)N1CCC(c2cn(-c3ccc(Cl)cc3)c3cnccc23)CC1]

Example 105 was prepared similarly to Example 17, from Example 10, using 4-{[(tert-butoxy)carbonyl]amino}butanoic acid instead of N-(tert-butoxycarbonyl)-(3-alanine prior to the Boc deprotection step to give the title compound as a yellow gum (12%). HRMS (ESI+) calcd for $C_{22}H_{25}ClN_4O$, 397.1783. found 397.1790. HPLC (method B): Rf 3.84 min, 99% purity.

Example 106

2-Aminoethyl 4-[1-(4-chlorophenyl)-1H-pyrrolo[2,3-c]pyridin-3-yl]piperidine-1-carboxylate

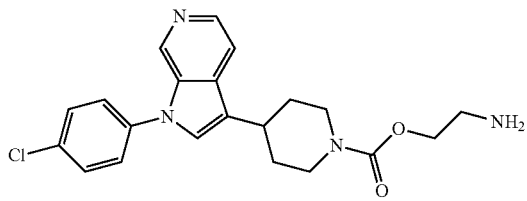 [SMILES: NCCOC(=O)N1CCC(c2cn(-c3ccc(Cl)cc3)c3cnccc23)CC1]

Triphosgene (95.2 mg, 0.32 mmol) was dissolved in DCM (5 mL) and a solution of N-Boc-ethanolamine (155 mg, 0.96 mmol) and DIPEA (167 µL, 0.96 mmol) in DCM (1 mL) was added. The reaction mixture was stirred for 18 h and a solution of Example 10 (free base, 200 mg, 0.64 mmol) and DIPEA (167 µL, 0.96 mmol) in DCM (1 mL) was added. The reaction mixture was stirred for 1 h, diluted with EtOAc (50 mL), washed with 10% aq citric acid (50 mL) and 1 M aq $Na_2CO_3$ (50 mL), dried ($MgSO_4$) and concentrated in vacuo. The residue was dissolved in DCM (5 mL), TFA (1 mL) was added and the reaction mixture was stirred for 1 h. The reaction mixture was concentrated in vacuo and purified by reverse phase HPLC. The residue was dissolved in 1 M aq $Na_2CO_3$ (20 mL) and extracted with DCM (3×20 mL). The combined organic fractions were dried ($MgSO_4$) and concentrated in vacuo to give the title compound as a colourless gum (10.0 mg, 3.9%). HRMS (ESI+) calcd for $C_{21}H_{23}ClN_4O_2$ 399.1582. found 399.1585. HPLC (method B): Rf 3.92 min, 99% purity.

Example 107

3-(3,6-Dihydro-2H-pyran-4-yl)-2-methyl-1-(4-methylphenyl)-1H-pyrrolo[2,3-c]pyridine

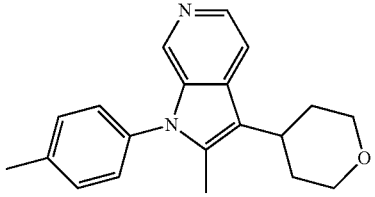 [SMILES: Cc1ccc(-n2c(C)c(C3CCOCC3)c3ccncc32)cc1]

Intermediate 108 (59.0 mg, 0.28 mmol), 4-iodotoluene (72.0 mg, 0.33 mmol), N,N-dimethylethylenediamine (5.93 µL, 0.06 mmol) and $K_3PO_4$ (123 mg, 0.58 mmol) were suspended in DMF (1 mL) under nitrogen and CuI (5.24 mg, 0.03 mmol) was added. The reaction mixture was heated in a microwave at 170° C. for 9 h and concentrated in vacuo. The residue was purified by column chromatography to give the title compound as a brown gum (10.3 mg, 12%). LCMS (ES$^+$): 305.0 (M+H)$^+$. HPLC (method B): Rf 5.01 min, 98.5% purity.

Biological Tests

Biological Assays of the SSAO Enzyme Inhibitors

All primary assays were performed at r.t. with purified recombinantly expressed human SSAO. Enzyme was prepared essentially as described in Öhman et al. (Protein Expression and Purification 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}C$-labeled substrate, or by utilizing the production of hydrogen peroxide in a horseradish peroxidise (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidise (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidise Assay kit, Invitrogen A22188). Enzyme and compounds in 50 mM sodium phosphate, pH 7.4 were set to pre-incubate in flat-bottomed microtiter plates for approximately 15 minutes before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 hours, exciting at 544 nm n and reading the emission at 590 nm. For the human SSAO assay final concentrations of the reagents in the assay wells were: SSAO enzyme 1 µg/ml, benzylamine 100 µM, Amplex reagent 20 µM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and $IC_{50}$ values were calculated using the GraphPad Prism 4 or XLfit 4 programs.

Aldehyde Detection:

SSAO activity was assayed using 14C-labeled benzylamine and analysed by measuring radioactive benzaldehyde. In a white 96-well optiplate (Packard), 20 µL of diluted test compound was pre-incubated at r.t. with 20 µL SSAO enzyme for approximately 15 minutes with continuous agitation. All dilutions were made with PBS. The reaction was initiated by adding 20 µL of the benzylamine substrate solution containing [7-14C] Benzylamine hydrochloride (CFA589, GE Healthcare). The plate was incubated for 1 hour as above after which the reaction was stopped by acidification (10 µL 1 M HCl). Then 90 µL Micro Scint-E solution (Perkin-Elmer) was added to each well and the plate was continuously mixed for 15 minutes. Phase separation occurred instantly and activity was read in a Topcount scintillation counter (Perkin-Elmer). In the final reaction well, human recombinant SSAO concentration was 10 µg/ml. In order to optimize sensitivity, the substrate concentration was decreased as compared to the HRP coupled assay in order to get a higher fraction of radioactive product. In the human SSAO assay, benzylamine concentration was 40 µM (0.2 µCi/mL). Data was analysed as above.

All of the exemplified compounds of the invention had an $IC_{50}$ value of 1-2500 nM at SSAO (See Table 9).

TABLE 9

| SSAO inhibitory activity | |
|---|---|
| Compound | $IC_{50}$ (nM) |
| 1 | C |
| 2 | C |
| 3 | B |
| 4 | B |
| 5 | B |
| 6 | C |
| 7 | C |
| 8 | B |
| 9 | C |
| 10 | B |
| 11 | B |
| 12 | A |
| 13 | B |
| 14 | B |
| 15 | A |
| 16 | A |
| 17 | A |
| 18 | B |
| 19 | B |
| 20 | B |
| 21 | B |
| 22 | B |
| 23 | C |
| 24 | C |
| 25 | C |
| 26 | C |
| 27 | C |
| 28 | B |
| 29 | C |
| 30 | B |
| 31 | C |
| 32 | A |
| 33 | A |
| 34 | B |
| 35 | B |

TABLE 9-continued

| SSAO inhibitory activity | |
|---|---|
| Compound | $IC_{50}$ (nM) |
| 36 | A |
| 37 | C |
| 38 | C |
| 39 | C |
| 40 | C |
| 41 | C |
| 42 | B |
| 43 | B |
| 44 | A |
| 45 | C |
| 46 | C |
| 47 | C |
| 48 | B |
| 49 | A |
| 50 | A |
| 51 | C |
| 52 | B |
| 53 | A |
| 54 | A |
| 55 | B |
| 56 | A |
| 57 | A |
| 58 | A |
| 59 | A |
| 60 | A |
| 61 | B |
| 62 | B |
| 63 | A |
| 64 | A |
| 65 | B |
| 66 | A |
| 67 | A |
| 68 | A |
| 69 | B |
| 70 | C |
| 71 | B |
| 72 | B |
| 73 | B |
| 74 | A |
| 75 | B |
| 76 | B |
| 77 | C |
| 78 | C |
| 79 | B |
| 80 | B |
| 81 | B |
| 82 | B |
| 83 | B |
| 84 | B |
| 85 | C |
| 86 | C |
| 87 | B |
| 88 | C |
| 89 | B |
| 90 | C |
| 91 | B |
| 92 | B |
| 93 | B |
| 94 | C |
| 95 | B |
| 96 | C |
| 97 | B |
| 98 | B |
| 99 | C |
| 100 | B |
| 101 | A |
| 102 | A |
| 103 | B |
| 104 | A |
| 105 | A |
| 106 | A |
| 107 | A |

(A: <100 nM, B: 100-500 nM, C: 500-2500 nM)

The invention claimed is:

1. A compound of formula (I) or a pharmaceutically acceptable salt, or N-oxide thereof:

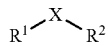
(I)

wherein

R$^1$ is phenyl or 6-membered heteroaryl, optionally substituted with one or more substituents selected from halogen, cyano, C$_{1-4}$-alkyl, and halo-C$_{1-4}$-alkyl;

R$^2$ is —B-Q-[R$^3$]$_n$ or —B—R$^3$, wherein n=1, 2, 3, or 4;

B is a bond or C$_{1-3}$-alkylene;

Q is saturated or partially unsaturated monocyclic 5-7 membered heterocyclic or C$_{5-7}$-cycloalkyl ring, either of which optionally comprises a bridge formed by an ethylene or propylene radical;

when R$^2$ is —B-Q-[R$^3$]$_n$, R$^3$ is individually selected from hydrogen, halogen, hydroxyl, oxo, C$_{1-4}$-alkyl, C$_{1-4}$-alkoxy, hydroxy-C$_{1-4}$-alkyl, cyano-C$_{1-4}$-alkyl, amino-C$_{1-4}$-alkyl, —NR$^{4A}$R$^{4B}$, —NR$^6$C(O)OR$^5$, —NR$^6$C(O)NR$^{4A}$R$^{4B}$, —C(O)NR$^{4A}$R$^{4B}$, —C(O)R$^5$, —C(O)OR$^5$, and heteroaryl-C$_{1-4}$-alkyl, and wherein any heteroaryl residue is optionally substituted with C$_{1-4}$-alkyl;

when R$^2$ is —B—R$^3$, R$^3$ is selected from hydroxy-C$_{1-4}$-alkyl; and

R$^{4A}$, R$^{4B}$ and R$^5$ are each independently selected from hydrogen, C$_{1-4}$-alkyl, hydroxy-C$_{1-4}$-alkyl, halo-C$_{1-4}$-alkyl, cyano-C$_{1-4}$-alkyl, amino-C$_{1-4}$-alkyl, C$_{1-4}$-alkylamino-C$_{1-4}$-alkyl, di(C$_{1-4}$-alkyl)-amino-C$_{1-4}$-alkyl and C$_{1-4}$alkoxy-C$_{1-4}$alkyl; or R$^{4A}$ and R$^{4B}$ together with the nitrogen to which they are attached form a cyclic amino group;

R$^6$ is hydrogen or C$_{1-4}$-alkyl; and

X is selected from the radicals of formulae (1-6) wherein the bond marked * is attached to R$^1$— and the bond marked ** is attached to —R$^2$:

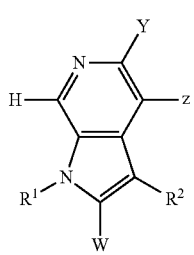
1

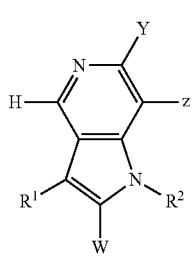
2

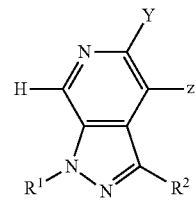
3

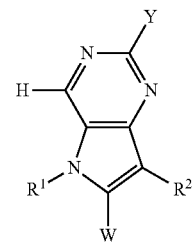
4

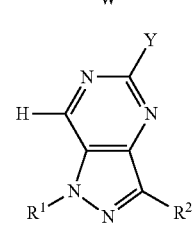
5

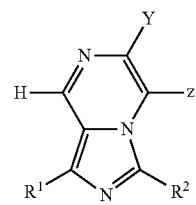
6 wherein Y is selected from hydrogen, hydroxyl, and —OCH$_3$;

Z is selected from hydrogen, fluorine, hydroxyl, and C$_{1-4}$-alkoxy; and

W is selected from hydrogen, and C$_{1-4}$-alkyl.

2. A compound as claimed in claim 1 in which X has the formula 1 and wherein R$^1$, R$^2$, Y, Z and W are as defined in claim 1.

3. A compound as claimed in claim 1 in which X has the formula 2 and wherein R$^1$, R$^2$, Y, Z and W are as defined in claim 1.

4. A compound as claimed in claim 1 in which X has the formula 3 and wherein R$^1$, R$^2$, Y, and Z are as defined in claim 1.

5. A compound as claimed in claim 1 in which X has the formula 4 and wherein R$^1$, R$^2$, Y, and W are as defined in claim 1.

6. A compound as claimed in claim 1 in which X has the formula 5 and wherein R$^1$, R$^2$, and Y are as defined in claim 1.

7. A compound as claimed in claim 1 in which X has the formula 6 and wherein R$^1$, R$^2$, Y, and Z are as defined in claim 1.

8. A compound as claimed in claim 1 wherein R$^2$ is —B-Q-[R$^3$]$_n$.

9. A compound as claimed in claim 1 wherein R$^2$ is —B—R$^3$.

10. A compound as claimed in claim 1 wherein B is a bond, or methylene.

11. A compound as claimed in claim 1 wherein B is a bond.

12. A compound as claimed in claim 1 wherein W is hydrogen.

13. A compound as claimed in claim 1 wherein Y is H, or OH.

14. A compound as claimed in claim 1 wherein Y is hydrogen.

15. A compound as claimed in claim 1 wherein $R^1$ is heteroaryl optionally substituted with one or more substituents selected from fluoro, chloro, and $C_{1-4}$-alkyl.

16. A compound as claimed in claim 15 wherein $R^1$ is pyridine-2-yl, pyridine-3-yl or pyridine-4-yl optionally substituted with one or more substituents selected from fluoro, chloro, and $C_{1-4}$-alkyl.

17. A compound as claimed in claim 1 wherein $R^1$ is phenyl, optionally substituted at the para, meta and ortho positions by one or more substituents selected from hydrogen, fluoro, chloro, cyano, $C_{1-4}$-alkyl, fluoromethyl, difluoromethyl, and trifluoromethyl.

18. A compound as claimed in claim 17 where $R^1$ is phenyl substituted at the para position by a substituent selected from, fluoro, chloro, cyano, $C_{1-4}$-alkyl, fluoromethyl, difluoromethyl, and trifluoromethyl.

19. A compound as claimed in claim 17 wherein the para substituent is selected from fluoro, chloro and methyl.

20. A compound as claimed in claim 17 wherein $R^1$ is phenyl substituted at the meta position by hydrogen.

21. A compound as claimed in claim 17 wherein $R^1$ is phenyl substituted at the ortho position by a substituent selected from hydrogen, fluoro, methyl, fluoromethyl, difluoromethyl, and trifluoromethyl.

22. A compound as claimed in claim 17 wherein $R^1$ is phenyl substituted at the ortho position by hydrogen, fluoro or methyl.

23. A compound as claimed in claim 1 wherein $R^2$ is —B-Q-[$R^3$]$_n$, and Q is a 7-membered saturated or partially unsaturated 7-membered heterocyclic or cycloalkyl ring.

24. A compound as claimed in claim 23 wherein Q is a homomorpholine ring, or a bridged homomorpholine ring wherein the bridge is formed by an ethylene or propylene radical.

25. A compound as claimed in claim 1 wherein $R^2$ is —B-Q-[$R^3$]$_n$, and Q is a 5- or 6-membered saturated or partially unsaturated 5 or 6 membered heterocyclic or cycloalkyl ring.

26. A compound as claimed in claim 25 wherein Q is selected from tetrahydrofuranyl, tetrahydropyranyl, piperidinyl, piperazinyl, morpholinyl, cyclohexyl, and any of the foregoing rings comprising a bridge formed by an ethylene or propylene radical.

27. A compound as claimed in claim 1 wherein $R^2$ is morpholin-4-yl, morpholin-4-yl-methyl, oxolan-3-yl, oxolan-3-yl-methyl, oxan-4-ylmethyl, oxan-4-yl, or tetrahydropyridinyl.

28. A compound as claimed in claim 1 wherein $R^2$ is piperidin-4-yl, piperazin-1-yl, piperidin-4-yl-methyl, oxopiperazine, or piperazin-1-yl methyl, any of which being optionally substituted by $R^3$ on the ring, or on the ring nitrogen in the 1-position.

29. A compound as claimed in claim 1 wherein $R^2$ is piperidin-1-yl or pyrrolidin-1-yl.

30. A compound as claimed in claim 1 wherein $R^2$ is morpholine.

31. A compound as claimed in claim 1 wherein $R^2$ is cyclopentyl, or cyclohexyl.

32. A compound as claimed in claim 9 wherein $R^2$ is an mono- or disubstituted amino group, the substituents being selected from $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, hydroxy-$C_{1-4}$-alkylamino-$C_{1-4}$-alkyl, di($C_{1-4}$-alkyl)amino-$C_{1-4}$-alkyl and $C_{1-4}$alkoxy-$C_{1-4}$alkyl.

33. A compound as claimed in claim 9 wherein $R^2$ is an $C_{1-4}$alkoxy-$C_{1-4}$alkyl, hydroxy-$C_{1-4}$-alkyl, cyano-$C_{1-4}$-alkyl, amino-$C_{1-4}$-alkyl, $C_{1-4}$-alkylamino-$C_{1-4}$-alkyl or di($C_{1-4}$-alkyl)amino-$C_{1-4}$-alkyl group.

34. A compound as claimed in claim 1 wherein $R^2$ is selected from: morpholin-4-yl, morpholin-4-yl-methyl, 4-methoxycyclohexyl, 4-aminocyclohexyl, 4-tertbutoxycarbonylamino-cyclohexyl, oxolan-3-yl, oxolan-3-ylmethyl, oxan-4-ylmethyl, oxan-4-yl, 3,6-dihydrooxan-4-yl, dimethylamino, N-(2-methoxyethyl)-N-methyl-amino, 1-hydroxyethylaminomethyl, piperidin-4-yl, 1-hydroxypiperidin-4-yl, 1-hydroxypiperidin-4-ylmethyl, 1-hydroxymethylpiperidin-4-yl, 1-hydroxyethylpiperidin-4-yl, 1-(3-cyanopropyl) piperidin-4-yl, 1-(3-cyanoethyl) piperidin-4-yl, 1-(1H-pyrazol-4-yl)methyl-piperidin-4-yl, 1-(1-methyl-1H-pyrazol-4-yl)methyl-piperidin-4-yl, 1-(3-aminopropan-1-one-1-yl) piperidin-4-yl, 1-(2-aminoethan-1-one-1-yl)piperidin-4-yl, 1-(2-dimethylaminoethan-1-one-1-yl)piperidin-4-yl, 1-(2-hydroxyethan-1-one-1-yl)piperidin-4-yl, 1-(3-(tertbutoxycarbonylamino)propan-1-one-1-yl)-piperidin-4-yl, 1-(2-(tertbutoxycarbonylamino)ethan-1-one-1-yl)-piperidin-4-yl, piperazin-1-yl, 4-methylpiperazin-1-yl, piperazin-1-yl-methyl, 4-methylpiperazin-1-yl-methyl, 4-methoxycarbonyl-piperazin-1-yl-methyl, hydroxymethyl, 2-hydroxyethyl, 1,2,3,6-tetrahydropyridin-4-yl, homomorpholin-4-yl, 2,2-dimethyl-morpholin-4-yl, 3,3-dimethyl-morpholin-4-yl, piperazin-2-one-4-yl, piperazine-2-one-5-yl, 8-oxa-3-azabicyclo[3.2.1]octane, 4-tertbutoxycarbonylpiperazin-1-yl-methyl, 3,3-difluoropyrrolidin-1-yl, 3-hydroxypyrrolidin-1-yl, 3-methoxypyrrolidin-1-yl, piperidine-1-yl, 4,4-difluoropiperidin-1-yl, 4-hydroxypiperidin-1-yl, 4-aminocarboxypiperidin-1-yl, 3-methylmorpholine-4-yl, 2-secbutylmorpholin4-yl, (2S,6R)-dimethyl morpholine-4-yl, 3-methyloxycarbonylmorpholin-4-yl, 1-methoxyethylaminomethyl, 2-aminomethylmorpholin-4-yl, 1-methoxyethylamino, 1-(3-aminoethylpropan-1-one)-piperazin-4-yl, 3-aminocarboxylmorpholin-4-yl, 3-(morpholine-4-carboxy)-morpholin-4-yl, 3-(1-aminoethyl-2-aminocarboxy)-morpholin-4-yl, morpholine-3-yl, morpholine-2-yl, 1-butylpiperidin-4-yl, 1-dimethylaminocarboxypiperidin-4-yl, 1-ethoxycarboxypiperidin-4-yl, 1-(4-aminobutan-1-one)piperidin-4-yl, 1-(2-aminoethoxycarboxy)piperidine-4-yl, and 1-tertbutoxycarbonyl-lpiperidin-4-yl.

35. A compound of formula (I) or a pharmaceutically acceptable salt, or N-oxide thereof:

$$R^1 \diagdown X \diagdown R^2 \quad (I)$$

wherein
$R^1$ is phenyl or 6-membered heteroaryl, optionally substituted with one or more substituents selected from halogen, cyano, $C_{1-4}$-alkyl, and halo-$C_{1-4}$-alkyl;
$R^2$ is —B-Q-[$R^3$]$_n$ or —B—$R^3$, wherein n=1, 2, 3, or 4;
B is a bond or $C_{1-3}$-alkylene;
Q is saturated or partially unsaturated monocyclic 5-7 membered heterocyclic or $C_{5-7}$-cycloalkyl ring, either of which optionally comprises a bridge formed by an ethylene or propylene radical:
when $R^2$ is —B-Q-[$R^3$]$_n$, $R^3$ is individually selected from hydrogen, halogen, hydroxyl, oxo, $C_{1-4}$-alkyl, $C_{1-4}$-alkoxy, hydroxy-$C_{1-4}$-alkyl, cyano- $C_{1-4}$-alkyl, amino-$C_{1-4}$-alkyl, —$NR^{4A}R^{4B}$, —$NR^6C(O)OR^5$, —$NR^6C(O)NR^{4A}R^{4B}$, —$C(O)NR^{4A}R^{4B}$, —$C(O)R^5$, —$C(O)OR^5$, and heteroaryl-$C_{1-4}$-alkyl, and wherein any heteroaryl residue is optionally substituted with $C_{1-4}$-alkyl;

when $R^2$ is —B—$R^3$, $R^3$ is selected from hydroxy-$C_{1-4}$-alkyl; and $R^{4A}$, $R^{4B}$ and $R^5$ are each independently selected from hydrogen, $C_{1-4}$-alkyl, hydroxy-$C_{1-4}$-alkyl, halo-$C_{1-4}$-alkyl, cyano-$C_{1-4}$-alkyl, amino-$C_{1-4}$-alkyl, $C_{1-4}$-alkylamino-$C_{1-4}$-alkyl, di($C_{1-4}$-alkyl)amino-$C_{1-4}$-alkyl and $C_{1-4}$alkoxy-$C_{1-4}$alkyl; or $R^{4A}$ and $R^{4B}$ together with the nitrogen to which they are attached form a cyclic amino group;

$R^6$ is hydrogen or $C_{1-4}$-alkyl; and

X is selected from the radicals of formulae (1-6) wherein the bond marked * is attached to $R^1$— and the bond marked ** is attached to —$R^2$:

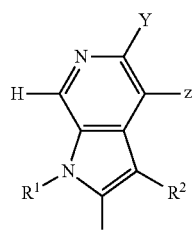

1

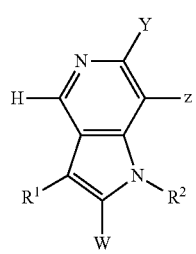

2

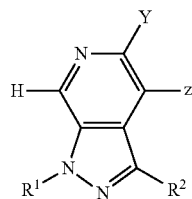

3

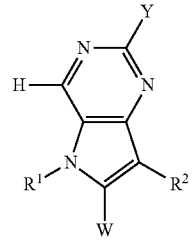

4

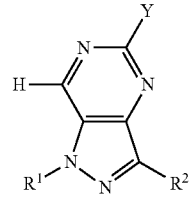

5

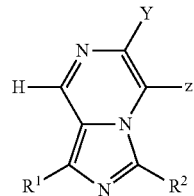

6 wherein Y is selected from hydrogen, hydroxyl, and —$OCH_3$;

Z is selected from hydrogen, fluorine, hydroxyl, and $C_{1-4}$-alkoxy; and

W is selected from hydrogen, and $C_{1-4}$-alkyl, which is:

3-(4-Chlorophenyl)-1-(oxolan-3-ylmethyl)-1H-pyrrolo[3,2-c]pyridine;

tert-Butyl 4-[3-(4-chlorophenyl)-1H-pyrrolo[3,2-c]pyridin-1-yl]piperidine-1-carboxylate;

3-(4-Chlorophenyl)-1-(oxolan-3-yl)-1H-pyrrolo[3,2-c]pyridine;

3-(4-Chlorophenyl)-1-(oxan-4-yl)-1H-pyrrolo[3,2-c]pyridine;

4-[3-(4-chlorophenyl)-1H-pyrrolo[3,2-c]pyridin-1-yl]piperidine;

4-[3-(3,4-Dichlorophenyl)-1H-pyrrolo[3,2-c]pyridin-1-yl]piperidine;

1-{4-[3-(3,4-Dichlorophenyl)-1H-pyrrolo[3,2-c]pyridin-1-yl]piperidin-1-yl}-2-hydroxyethan-1-one;

4-[1-(4-Chlorophenyl)-1H-pyrrolo[2,3-c]pyridin-3-yl];

tert-Butyl 4-[1-(4-chlorophenyl)-1H-pyrrolo[2,3-c]pyridin-3-yl]piperidine-1-carboxylate;

1-(4-Chlorophenyl)-3-piperidin-4-yl-1H-pyrrolo[2,3-c]pyridine;

tert-Butyl N-{1-[1-(4-chlorophenyl)-1H-pyrrolo[2,3-c]pyridin-3-yl]cyclohexyl}carbamate;

4-[1-(4-Chlorophenyl)-1H-pyrrolo[2,3-c]pyridin-3-yl]cyclohexan-1-amine;

4-[1-(4-Chloro-2-methylphenyl)-1H-pyrrolo[2,3-c]pyridin-3-yl]cyclohexan-1-amine;

1-{4-[1-(4-Chlorophenyl)-1H-pyrrolo[2,3-c]pyridin-3-yl]piperidin-1-yl}-2-(dimethyl-amino)ethan-1-one;

1-{4-[1-(4-Chlorophenyl)-1H-pyrrolo[2,3-c]pyridine-3-yl]piperidin-1-yl}-2-hydroxyethan-1-one;

2-Amino-1-{4-[1-(4-chlorophenyl)-1H-pyrrolo[2,3-c]pyridin-3-yl]piperidin-1-yl}ethan-1-one;

3-Amino-1-{4-[1-(4-chlorophenyl)-1H-pyrrolo[2,3-c]pyridin-3-yl]piperidin-1-yl}propan-1-one;

2-{4-[1-(4-Chlorophenyl)-1H-pyrrolo[2,3-c]pyridin-3-yl]piperidin-1-yl}ethan-1-ol;

4-[1-(4-Chlorophenyl)-1H-pyrrolo[2,3-c]pyridin-3-yl]-1-(1H-pyrazol-3-ylmethyl)piperidine;

4-[1-(4-Chlorophenyl)-1H-pyrrolo[2,3-c]pyridin-3-yl]-1-[(1-methyl-1H-pyrazol-4-yl)-methyl]piperidine;

3-{4-[1-(4-Chlorophenyl)-1H-pyrrolo[2,3-c]pyridine-3-yl]piperidin-1-yl}propanenitrile;

4-{4-[1-(4-Chlorophenyl)-1H-pyrrolo[2,3-c]pyridin-3-yl]piperidin-1-yl}butanenitrile;

[1-(4-Chlorophenyl)-1H-pyrrolo[2,3-c]pyridin-3-yl]methanol;

1-{[1-(4-Chlorophenyl)-1H-pyrrolo[2,3-c]pyridin-3-yl]methyl}-4-methylpiperazine;

tert-Butyl 4-{[1-(4-chlorophenyl)-1H-pyrrolo[2,3-c]pyridin-3-yl];

1-{[1-(4-Chlorophenyl)-1H-pyrrolo[2,3-c]pyridin-3-yl]methyl}piperazine;

2-(1-{[1-(4-Chlorophenyl)-1H-pyrrolo[2,3-c]pyridin-3-yl]methyl}piperidin-4-yl)ethan-1-ol;
(1-{[1-(4-Chlorophenyl)-1H-pyrrolo[2,3-c]pyridin-3-yl]methyl}piperidin-4-yl)methanol;
4-{[1-(4-Chlorophenyl)-1H-pyrrolo[2,3-c]pyridin-3-yl]methyl}morpholine;
1-{[1-(4-Chlorophenyl)-1H-pyrrolo[2,3-c]pyridin-3-yl]methyl}piperidin-4-ol;
2-({[1-(4-Chlorophenyl)-1H-pyrrolo[2,3-c]pyridin-3-yl]methyl}amino)ethan-1-ol;
4-[3-(4-Methylphenyl)imidazo[1,5-a]pyrazin-1-yl]morpholine;
4-[3-(4-Chlorophenyl)imidazo[1,5-a]pyrazin-1-yl]morpholine;
3-(4-Chlorophenyl)-N-(2-methoxyethyl)-N-methylimidazo[1,5-a]pyrazin-1-amine;
3-(4-Chlorophenyl)-N,N-dimethylimidazo[1,5-a]pyrazin-1-amine;
3-(4-Chlorophenyl)-1-(oxan-4-yl)imidazo[1,5-a]pyrazine;
3-(4-Chlorophenyl)-1-(oxan-4-ylmethyl)imidazo[1,5-a]pyrazine;
3-(4-Chlorophenyl)-1-(oxolan-3-yl)imidazo[1,5-a]pyrazine;
3-(4-Chlorophenyl)-1-(4-methoxycyclohexyl)imidazo[1,5-a]pyrazine;
3-(Oxan-4-yl)-1-phenyl-1H-pyrazolo[3,4-c]pyridine;
4-[3-(Oxan-4-yl)-1H-pyrazolo[3,4-c]pyridin-1-yl]benzonitrile;
1-[4-(Difluoromethyl)phenyl]-3-(oxan-4-yl)-1H-pyrazolo[3,4-c]pyridine;
1-(2-Fluoro-4-methylphenyl)-3-(oxan-4-yl)-1H-pyrazolo[3,4-c]pyridine;
1-(4-Chloro-2-fluorophenyl)-3-(oxan-4-yl)-1H-pyrazolo[3,4-c]pyridine;
1-(2,4-Dimethylphenyl)-3-(oxan-4-yl)-1H-pyrazolo[3,4-c]pyridine;
5-Methyl-2-[3-(oxan-4-yl)-1H-pyrazolo[3,4-c]pyridin-1-yl]pyridine;
2-Methyl-5-[3-(oxan-4-yl)-1H-pyrazolo[3,4-c]pyridin-1-yl]pyridine;
1-[1-(4-Chlorophenyl)-1H-pyrazolo[3,4-c]pyridin-3-yl]-3,3-difluoropyrrolidine;
1-[1-(4-Chlorophenyl)-1H-pyrazolo[3,4-c]pyridin-3-yl]pyrrolidin-3-ol;
3-Methoxy-1-[1-(4-methylphenyl)-1H-pyrazolo[3,4-c]pyridin-3-yl]pyrrolidine;
1-[1-(4-Chlorophenyl)-1H-pyrazolo[3,4-c]pyridin-3-yl]piperidine;
1-[1-(4-Chlorophenyl)-1H-pyrazolo[3,4-c]pyridin-3-yl]-4,4-difluoropiperidine;
1-[1-(4-Chlorophenyl)-1H-pyrazolo[3,4-c]pyridin-3-yl]piperidin-4-ol;
1-[1-(4-Methylphenyl)-1H-pyrazolo[3,4-c]pyridin-3-yl]piperidine-4-carboxamide;
4-[1-(4-Fluorophenyl)-1H-pyrazolo[3,4-c]pyridin-3-yl]morpholine;
4-[1-(4-Chlorophenyl)-1H-pyrazolo[3,4-c]pyridin-3-yl]morpholine;
2,2,2-Trifluoroacetic acid; 4-[1-(4-methylphenyl)-1H-pyrazolo[3,4-c]pyridin-3-yl]morpholine;
4-[1-(2-Fluoro-4-methylphenyl)-1H-pyrazolo[3,4-c]pyridin-3-yl]morpholine;
4-[1-(4-Chlorophenyl)-1H-pyrazolo[3,4-c]pyridin-3-yl]-2-methylmorpholine;
4-[1-(4-Chlorophenyl)-1H-pyrazolo[3,4-c]pyridin-3-yl]-3-methylmorpholine;
4-[1-(4-Methylphenyl)-1H-pyrazolo[3,4-c]pyridin-3-yl]-2-(2-methylpropyl)morpholine;
(2S,6R)-4-[1-(4-Chlorophenyl)-1H-pyrazolo[3,4-c]pyridin-3-yl]-2,6-dimethylmorpholine;
3-[1-(4-Methylphenyl)-1H-pyrazolo[3,4-c]pyridin-3-yl]-8-oxa-3-azabicyclo[3.2.1]octane;
2,2-Dimethyl-4-[1-(4-methylphenyl)-1H-pyrazolo[3,4-c]pyridin-3-yl]morpholine;
3,3-Dimethyl-4-[1-(4-methylphenyl)-1H-pyrazolo[3,4-c]pyridin-3-yl]morpholine;
Methyl 4-[1-(4-methylphenyl)-1H-pyrazolo[3,4-c]pyridin-3-yl]morpholine-3-carboxylate;
4-[1-(4-Methylphenyl)-1H-pyrazolo[3,4-c]pyridin-3-yl]-1,4-oxazepane;
4-[1-(4-Methylphenyl)-1H-pyrazolo[3,4-c]pyridin-3-yl]piperazin-2-one;
N-(2-Methoxyethyl)-N-methyl-1-(4-methylphenyl)-1H-pyrazolo[3,4-c]pyridin-3-amine;
1-[1-(4-Chlorophenyl)-1H-pyrazolo[3,4-c]pyridin-3-yl]piperazine;
1-[1-(4-Chlorophenyl)-1H-pyrazolo[3,4-c]pyridin-3-yl]piperidin-4-amine;
{4-[1-(4-Methylphenyl)-1H-pyrazolo[3,4-c]pyridin-3-yl]morpholin-2-yl}methanamine;
tert-Butyl N-(2-methoxyethyl)-N-[1-(4-methylphenyl)-1H-pyrazolo[3,4-c]pyridin-3-yl]carbamate;
1-[1-(4-Methylphenyl)-1H-pyrazolo[3,4-c]pyridin-3-yl]piperidin-4-ol;
1-[1-(4-Chlorophenyl)-1H-pyrazolo[3,4-c]pyridin-3-yl]-4-(1H-pyrazol-3-ylmethyl)piperazine;
tert-Butyl N-(3-{4-[1-(4-chlorophenyl)-1H-pyrazolo[3,4-c]pyridin-3-yl]piperazin-1-yl}-3-oxopropyl)carbamate;
4-[1-(4-Methylphenyl)-1H-pyrazolo[3,4-c]pyridin-3-yl]morpholine-3-carboxamide;
4-[1-(4-Methylphenyl)-1H-pyrazolo[3,4-c]pyridin-3-yl]-3-[(morpholin-4-yl)carbonyl]morpholine;
N-(2-Aminoethyl)-4-[1-(4-methylphenyl)-1H-pyrazolo[3,4-c]pyridin-3-yl]morpholine-3-carboxamide;
1-(4-Chlorophenyl)-3-(oxan-4-yl)-1H-pyrazolo[3,4-c]pyridine;
1-(4-Methylphenyl)-3-(oxolan-3-yl)-1H-pyrazolo[3,4-c]pyridine;
1-(4-Methylphenyl)-3-(oxan-4-yl)-1H-pyrazolo[3,4-c]pyridine;
1-(4-Fluorophenyl)-3-(oxan-4-yl)-1H-pyrazolo[3,4-c]pyridine;
4-[1-(4-Chlorophenyl)-1H-pyrazolo[3,4-c]pyridin-3-yl]piperidine;
3-[1-(4-Methylphenyl)-1H-pyrazolo[3,4-c]pyridin-3-yl]morpholine;
2-[1-(4-Methylphenyl)-1H-pyrazolo[3,4-c]pyridin-3-yl]morpholine;
5-[1-(4-Methylphenyl)-1H-pyrazolo[3,4-c]pyridin-3-yl]piperidin-2-one;
1-(4-Chlorophenyl)-4-fluoro-3-(oxan-4-yl)-1H-pyrazolo[3,4-c]pyridine;
4-[1-(4-Chlorophenyl)-1H-pyrazolo[3,4-c]pyridin-3-yl]-1-(1H-pyrazol-3-ylmethyl)piperidine;
1-Butyl-4-[1-(4-chlorophenyl)-1H-pyrazolo[3,4-c]pyridin-3-yl]piperidine;
4-[1-(4-Chlorophenyl)-1H-pyrazolo[3,4-c]pyridin-3-yl]-N,N-dimethylpiperidine-1-carboxamide;
Ethyl 4-[1-(4-chlorophenyl)-1H-pyrazolo[3,4-c]pyridin-3-yl]piperidine-1-carboxylate;
3-Amino-1-{4-[1-(4-chlorophenyl)-1H-pyrazolo[3,4-c]pyridin-3-yl]piperidin-1-yl}propan-1-one;

1-(4-Chlorophenyl)-4-methoxy-3-(oxan-4-yl)-1H-pyrazolo[3,4-c]pyridine;
1-(4-Chlorophenyl)-3-(oxan-4-yl)-1H-pyrazolo[3,4-c]pyridin-4-ol;
1-(4-Chlorophenyl)-5-methoxy-3-(oxan-4-yl)-1H-pyrazolo[3,4-c]pyridine;
1-(4-Chlorophenyl)-3-(oxan-4-yl)-1H,5H,6H-pyrazolo[3,4-c]pyridin-5-one;
5-(4-Chlorophenyl)-7-(oxan-4-yl)-5H-pyrrolo[3,2-d]pyrimidine;
1-(4-Chlorophenyl)-3-(oxan-4-yl)-1H-pyrazolo[4,3-d]pyrimidine;
1-(4-Fluorophenyl)-3-(oxan-4-yl)-1H-pyrrolo[2,3-c]pyridine;
1-(4-Chlorophenyl)-3-(oxan-4-yl)-1H-pyrrolo[2,3-c]pyridine;
1-(4-Methylphenyl)-3-(oxan-4-yl)-1H-pyrrolo[2,3-c]pyridine;
5-Chloro-2-[3-(oxan-4-yl)-1H-pyrrolo[2,3-c]pyridin-1-yl]pyridine;
4-[1-(4-Chlorophenyl)-1H-pyrrolo[2,3-c]pyridin-3-yl]morpholine;
4-amino-1-{4-[1-(4-chlorophenyl)-1H-pyrrolo[2,3-c]pyridin-3-yl]piperidin-1-yl}butan-1-one;
2-Aminoethyl 4-[1-(4-chlorophenyl)-1H-pyrrolo[2,3-c]pyridin-3-yl]piperidine-1-carboxylate; and
3-(3,6-Dihydro-2H-pyran-4-yl)-2-methyl-1-(4-methylphenyl)-1H-pyrrolo[2,3-c]pyridine;

or a pharmaceutically acceptable salt, or N-oxide thereof.

36. A pharmaceutical composition comprising a compound as claimed in claim 1, together with one or more pharmaceutically acceptable carriers and/or excipients.

37. A compound according to claim 1 wherein $R^{4A}$ and $R^{4B}$ together with the nitrogen to which they are attached form a cyclic amino group selected from piperidinyl, piperazinyl, morpholinyl and homopiperidinyl.

* * * * *